United States Patent [19]
Cantley et al.

[11] Patent Number: 6,004,757
[45] Date of Patent: *Dec. 21, 1999

[54] SUBSTRATE SPECIFICITY OF A PROTEIN KINASES

[75] Inventors: Lewis C. Cantley, Cambridge; Zhou Songyang, Brookline, both of Mass.

[73] Assignee: Beth Israel Hospital, Boston, Mass.

[ * ] Notice: This patent is subject to a terminal disclaimer.

[21] Appl. No.: 08/369,643

[22] Filed: Jan. 6, 1995

Related U.S. Application Data

[63] Continuation-in-part of application No. 08/178,570, Jan. 7, 1994, Pat. No. 5,532,167.

[51] Int. Cl.$^6$ .............................. G01N 33/53; C07K 7/00
[52] U.S. Cl. ........................... 435/7.1; 435/331; 436/86; 436/518; 530/328; 530/329; 530/330; 530/331; 514/15; 514/16; 514/17; 514/18
[58] Field of Search .................................. 514/15, 16, 17, 514/18; 436/518, 86; 530/328, 329, 330, 331; 435/7.1

[56] References Cited

U.S. PATENT DOCUMENTS 5,532,167  7/1996  Cantley et al. ........................... 436/89

FOREIGN PATENT DOCUMENTS

WO 93/07169  4/1993  WIPO .

OTHER PUBLICATIONS

Abastado, J.–P. et al. (1993) "A Soluble, Single–Chain $K^d$ Molecule Produced By Yeast Selects A Peptide Repertoire Indistinguishable From That Of That Of Cell–Surface–Associated $K^d$" *Eur. J. Immunol.* 23:1776–1783.

Burke, Jr., T.R. (1992) "Protein–Tyrosine Kinase Inhibitors" *Drugs Fut.* 17(2):119–131.

Cheng, H–C. et al. (1985) "An Active Twenty–Amino–Acid–Residue Peptide Derived From the Inhibitor Protein of the Cyclic AMP–Dependent Protein Kinase" *Biochem. J.* 231:655–661.

Cheng, H–C. et al. (1986) "A Potent Synthetic Peptide Inhibitor of the cAMP–Dependent Protein Kinase" *Journal of Biological Chemistry* 261(3):989–992.

Flynn, G.C. et al. (1991) "Peptide–binding Specificity of the Molecular Chaperone BiP" *Nature* 353:726–730.

Graff, J.M. et al. (1991) "Protein Kinase C Substrate and Inhibitor Characteristics of Peptides Derived From the Myristoylated Alanine–Rich C Kinade Substrate (MARCKS) Protein Phosphorylation Site Domain" *Journal of Biological Chemistry* 266(22):14390–14398.

Hanks, S.K. (1988) "The Protein Kinase Family: Conserved Features and Deduced Phylogeny of the Catalytic Domains" *Science* 241:42–52.

Heidaran, M.A. et al. (1993) "Differences in Substrates Specificities of α and β Platelet–derived Growth Factor (PDGF) Receptors" *Journal of Biological Chemistry* 268(13):9287–9295.

Hortin, G.L. et al. (1992) "Preparation of Soluble Peptide Libraries: Application To Studies of Platelet Adhesion Sequences" *Biochemistry International* 26(4): 731–738.

Houghten, R.A. (1993) "Peptide Libraries: Criteria and Trends" *TIG* 9(7):235–239.

Houghten, R.A. et al. (1991) "Generation and Use of Synthetic Peptide Combinatorial Libraries for Basic Research and Drug Discovery" *Nature* 354:84–86.

Houghten, R.A. et al. (1992) "The Use of Synthetic Peptide Combinatorial Libraries for the Identification of Bioactive Peptides" *Bio Techniques* 13(3):412–421.

Keane, N.E. et al. (1993) "Substrate Specificity of the Insulin Receptor Tyrosine Kinase Domain" *Biochemical Society Transactions* 21:266S–267S.

Kemp, B.E. et al. (1976)"Synthetic Hexapeptide Substrates and Inhibitors of 3':5'–Cyclic AMP–Dependent Protein Kinase" *Proc. Nat. Acad. Sci. USA* 73(4):1038–1042.

Lam, K.S. et al. (1991) "A New Type of Synthetic Peptide Library For Identifying Ligand–Binding Activity" *Nature* 354:82–84.

Lorenz, U. et al. (1994) "Lck–Dependent Tyrosol Phosphorylation of the Phosphotyrosine Phosphatase SH–PTP1 in Murine T Cells" *Mollecular and Cellular Biology* 14:1824–1834.

Muszynska, G. et al. (1992) "Model Studies on Iron (III) Ion Affinity Chromatography" *Journal of Chromatography* 604:19–28.

Muszynska, G. et al. (1986) "Selective Adsorption of Phosphoproteins on Gel–Immobilized Ferric Chelate" *Biochemistry* 25(22):6850–6853.

O'Neil, K.T. et al. (1992) "Identification of Novel Peptide Antagonists for GPllb/llla From a Conformationally Constrained Phage Peptide Library" *Proteins: Structure, Function, and Genetics* 14:509–515.

(List continued on next page.)

*Primary Examiner*—Bennett Celsa
*Attorney, Agent, or Firm*—Testa, Hurwitz & Thibeault, LLP

[57] ABSTRACT

The invention provides a method for determining an amino acid sequence motif for a phosphorylation site of a protein kinase. In the method of the invention, a protein kinase is contacted with an oriented degenerate peptide library, peptides within the library which are substrates for the kinase are converted to phosphopeptides and the phosphopeptides are separated from non-phosphorylated peptides. The isolated phosphopeptides are sequenced and an amino acid sequence motif for the phosphorylation site is determined based upon the relative abundance of different amino acids residues at each degenerate position. The invention also provides peptide substrates for protein kinase A, cell cycle control kinases (including cyclin B/p33$^{cdc2}$ and cyclin A/p33$^{CDK2}$), src family kinases (including pp60$^{c-src}$ and pp60$^{v-src}$), EGF receptor, p92$^{c-fps/fes}$, lck, c-abl, PDGF receptor, FGF receptor, insulin receptor, casein kinase II, NIMA kinase, phosphorylase kinase, Cam kinase II and Erk1 based upon amino acid sequence motifs for the phosphorylation sites of these kinases.

6 Claims, 16 Drawing Sheets

OTHER PUBLICATIONS

Peter, M. et al. (1990) "Identification of Major Nucleolar Proteins As Candidate Mitotic Substrates of cdc2 Kinase" *Cell* 60:791–801.

Pinilla, C. et al. (1992) "Rapid Identification of High Affinity Peptide Ligands Using Positional Scanning Synthetic Peptide Combinatorial Libraries" *Bio Techniques* 13(6):901–905.

Schumacher, T.N.M. et al. (1992) "Synthetic Peptide Libraries in the Determination of T Cell Epitopes and Peptide Binding Specificity of Class I Molecules" *Eur. J. Immunol.* 22:1405–1412.

Shoelson, S.E. et al. (1992) "YMXM motifs of IRS–1 define substrate specificity of the insulin receptor kinase" *Proc. Natl. Acad. Sci. USA* 89:2027–2031.

Songyang, Z. et al. (1993) "SH2 Domains Recognize Specific Phosphopeptide Sequences" *Cell* 72:767–778.

Walker, D.H. et al. (1987) "Substrate Specificity and Kinetic Mechanism of Human Placental Insulin Receptor/Kinase" *Biochemistry* 26:1428–1433.

Songyang, Z. et al. (1994) "Use of an Oriented Peptide Library to Determine the Optimal Substrates of Protein Kinases" *Current Biology*, vol. 4, No. 11, pp. 973–982.

Till, J.H. et al. (1994) "Use of Synthetic Peptide Libraries and Phosphopeptide Selective Mass Spectrometry to Probe Protein Kinase Substrate Specificity" *J. Biol. Chem.* vol. 269, No. 10, pp. 7423–7428.

Wu, J. et al. (1994) "Identifying Substrate Motifs of Protein Kinases by Random Library Approach", *Biochemistry*, vol. 33, No. 49, pp. 14825–14833.

Marin, O. et al. (1990) "Synthetic Peptides including Acidic Clusters as Subtrates of Yeast Casein Kinase–2", *Int. J. Protein Res.* vol. 36, pp. 374–380.

Meggio, F. et al. (1984) "Synthetic Peptides including Acidic Clusters as Substrates and Inhibitors of Rat Liver Casein Kinase TS (Type–2)", *J. Biol. Chem.* vol. 259, No. 23, pp. 14576–14579.

Hortin, G.L. et al. (1990) "Inhibition of Thrombin's Clotting Activity by Synthetic Peptide Segments of its Inhibitors and Substrates", *Biochem. Biophys. Res. Commun.*, vol. 169, No. 2, pp. 437–442.

Caplus 121: 198763, Garnier et al. J. Biomol. Struct. DYM 11(5) 983–1002 (1994).

Titanji et al. J. Biol. Chem. vol. 255 No. 23 (Dec. 1980) pp. 11339–11343.

SUBSTRATE SPECIFICITY OF A PROTEIN KINASES

RELATED APPLICATIONS

This application is a continuation-in-part of U.S. patent application Ser. No. 08/178,570, filed Jan. 7, 1994 now U.S. Pat. No. 5,532,167 issued Jul. 2, 1996, the contents of which are hereby incorporated by reference.

BACKGROUND OF THE INVENTION

The activity of cells is regulated by external signals that stimulate or inhibit intracellular events. The process by which stimulatory or inhibitory signals are transmitted into and within a cell to elicit an intracellular response is referred to as signal transduction. Proper signal transduction is essential for proper cellular function. Defects in various components of signal transduction pathways, from cell surface receptors to activators of gene transcription, account for a vast number of diseases, including numerous forms of cancer, vascular diseases and neuronal diseases.

Protein kinases are enzymes involved in signal transduction which phosphorylate other proteins and/or themselves (autophosphorylation). Protein kinases involved in signal transduction in eukaryotic cells can be divided into three major groups based upon their substrate utilization: protein-tyrosine specific kinases (which phosphorylate substrates on tyrosine residues), protein-serine/threonine specific kinases (which phosphorylate substrates on serine and/or threonine residues) and dual-specificity kinases (which phosphorylate substrates on tyrosine, serine and/or threonine residues). Well over a hundred protein kinases have been identified to date and more are being identified at a very fast rate (about 10 to 30 new kinases per year) through genetic and molecular biological approaches. There are conserved regions among all protein kinases, suggesting evolution from a common ancestor. For reviews on protein kinases see Kemp, B. E. (ed.), (1990) *Peptides and Protein Phosphorylation.* CRC Press Inc. and Hanks et al. (1988) Science 241:42–52.

In order to insure fidelity in intracellular signal transduction cascades it is essential that each protein kinase have exquisite specificity in downstream targets. In some cases a kinase may have only a single substrate in a cell, but in general kinases appear to have a collection of targets that allow branching of an initial signal delivered to a cell in multiple directions in order to coordinate a set of events that occur in parallel for a given cellular response (see Roach, P. J. (1991) *J. Biol. Chem.* 266:14139–14142). The substrate specificity of a protein kinase can be influenced by at least three general mechanisms that depend on the overall structure of the enzyme: 1) specific domains in certain protein kinases target them to specific locations in the cell, thereby restricting their substrate availability; 2) other domains in the kinase, distinct from the catalytic domain, may provide high affinity association with either the substrate or an adapter molecule that presents the substrate to the kinase; and 3) specificity is ultimately provided by the structure of the catalytic site of the protein kinase.

Although the number of protein kinases that have been implicated in intracellular signaling is quite large, in only a few cases is there information about the sequence specificity of these kinases. This information has usually come from locating the phosphorylation sites on in vivo and/or in vitro substrates of the kinase. (For examples see Taylor et al., (1990) *Ann. Rev. Biochem.* 59:971–1005; Cheng, et al. (1991) *J. Biol. Chem.* 266:17919–17925; Walsh et al. (1990) in *Peptides and Protein Phosphorylation.* (B. E. Kemp, ed.) CRC Press Inc.pp. 43–84; Gaehlen and Harrison (1990) in *Peptides and Protein Phosphorylation.* (B. E. Kemp, ed.) CRC Press Inc.pp. 239–254). By comparing the sequences of several phosphorylation sites for a kinase a consensus sequence for substrates of that kinase can be determined. These types of studies have demonstrated the importance of the primary amino acid sequence around the site of phosphorylation in determining the in vivo specificity of protein kinases. Synthetic peptides can be constructed based upon the consensus sequence motif of a known phosphorylation site and individual amino acids can then be replaced one by one in order to determine the importance of particular amino acids on the $K_M$ or $V_{max}$ of the phosphorylation reaction.

However, there are severe limitations to this approach for determining the substrate specificity of a protein kinase. The procedure is quite expensive and laborious since each amino acid residue within a phosphorylation site must be altered individually to evaluate its importance. This approach does not necessarily identify all the residues critical for substrate specificity and, furthermore, an optimal substrate sequence is not likely to be determined unless each residue is changed to every other possible amino acid residue individually and then evaluated. For example, based upon an estimation of 9 to 12 amino acid residues of a substrate contacting the active site cleft of a kinase there would be approximately $1.024 \times 10^{13}$ ($20^{10}$) distinct peptides to consider. Moreover, in many cases this approach is not feasible because in vivo substrates for some kinase cannot be determined with certainty. For example, if an extracellular signal activates multiple kinases which phosphorylate multiple substrates or if a signal activates a cascade of kinases it is difficult to determine which kinase phosphorylates which substrate. An even more difficult problem in determining the substrate specificity of certain kinases is that their critical in vivo substrates are often proteins which are present in vivo in very low abundance and thus are not easily detectable by in vivo phosphorylation assays. Even relatively abundant substrates can be overlooked because of their high rates of dephosphorylation by closely-associated phosphatases.

Thus, there is a need for an alternative method to that of isolating and examining the sequences of native substrates for determining the substrate specificity of a protein kinase. Consensus sequence motifs for the phosphorylation sites of many known protein kinases have not yet been determined because of the limitations to current approaches discussed above. Information on the substrate specificity of each protein kinase involved in signal transduction would provide insight into signal transduction mechanisms and could allow for the design of novel therapeutic agents based on the substrate specificities of different protein kinases.

SUMMARY OF THE INVENTION

The invention provides a method for determining an amino acid sequence motif for a phosphorylation site of a protein kinase based upon selection of a subpopulation of peptides from a degenerate peptide library that are substrates for a protein kinase. In the method, peptides within an oriented degenerate peptide library that can be substrates for a protein kinase are phosphoryated by the kinase, converting them to phosphopeptides. The phosphopeptides are then separated from the remaining non-phosphorylated peptides in the library, thereby isolating the subpopulation of peptides that are substrates for the kinase. This subpopulation of peptides is then sequenced and the relative abundance of each amino acid residue at each degenerate position of the peptides is determined. An amino acid sequence motif for the phosphorylation site of a protein kinase can be determined from the most abundant amino acid residues at each degenerate position of the peptides within the library.

The peptides of the oriented degenerate peptide library can have the formula:

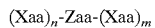

wherein Zaa is a non-degenerate phosphorylatable amino acid selected from the group consisting of Ser, Thr and Tyr, Xaa is any amino acid and n and m are integers from 1–10 inclusive. Alternatively, certain amino acids can be omitted from the degenerate positions of the peptides of the library such that Zaa is the only phosphorylatable amino acid in the peptides. Accordingly, in another embodiment, when Zaa is Ser or Thr, Xaa is any amino acid except Ser or Thr. Likewise, in another embodiment, when Zaa is Tyr, Xaa is any amino acid except Tyr. Additionally, non-degenerate amino acid residues can be added to the N-terminal and/or C-terminal ends of the peptides of the oriented degenerate peptide library.

In one embodiment of the method of the invention, the phosphorylated peptides are separated from the non-phosphorylated peptides by binding the phosphorylated peptides to a ferric column. Alternatively, the peptides in the library can be thio-phosphorylated and the thio-phosphorylated peptides can be separated from non-phosphorylated peptides by binding the thio-phosphorylated peptides to a mercury column.

The method of the invention can be used to determine an amino acid sequence motif for a phosphorylation site of any protein kinase, including protein-serine/threonine specific kinases, protein-tyrosine specific kinases and dual-specificity kinases. Preferred families of kinases include cyclic nucleotide-dependent kinases, cell cycle control kinases, src family kinases, epidermal growth factor receptor-like kinases and abl family kinases.

The amino acid sequence motif of a phosphorylation site of a kinase, determined by the method of the invention, can be used to make peptide substrates for the kinase. The peptide substrates comprise amino acid sequences corresponding to the amino acid sequence motif, which represents the preferred phosphorylation site for the kinase. Thus, these peptide substrates have a very high affinity for the kinase.

The peptide substrates of the invention can be incorporated into a larger protein to create a preferred phosphorylation site for a kinase within the protein.

The amino acid sequence motif of a phosphorylation site of a kinase, determined by the method of the invention, can also be used to make pseudosubstrates for the kinase. The pseudosubstrates comprise peptides having amino acid sequences corresponding to the amino acid sequence motif but in which the phosphorylatable amino acid residue is replaced by a non-phosphorylatable amino acid residue. Peptide analogs can also be designed based upon the amino acid sequence motifs provided by the invention.

The peptide substrates and pseudosubstrates of the invention can be used to inhibit the activity of a kinase. The phosphorylation of a substrate by a particular kinase can be inhibited by contacting the kinase with an inhibitory amount of a peptides substrate or pseudosubstrate for the kinase, as provided by the invention.

The invention provides the amino acid sequence motifs for the phosphorylation sites of protein kinase A, cell cycle control kinases (including cyclin B/p33cdc2 and cyclin A/p33CDK2), src family kinases (including pp60c-src and pp60v-src), epidermal growth factor receptor (EGFR), p92$^{c\text{-}fps/fes}$, lck, c-abl, platelet derived growth factor receptor (PDGFR), fibroblast growth factor receptor (FGFR), insulin receptor, casein kinase II, the cell-cycle regulated protein kinase NIMA, phosphorylase kinase, Cam kinase II and Erk 1. Peptide substrates and pseudosubstrates for these kinases, based upon the amino acid sequence motifs, are encompassed by the invention.

DETAILED DESCRIPTION OF THE INVENTION

Figure 1:
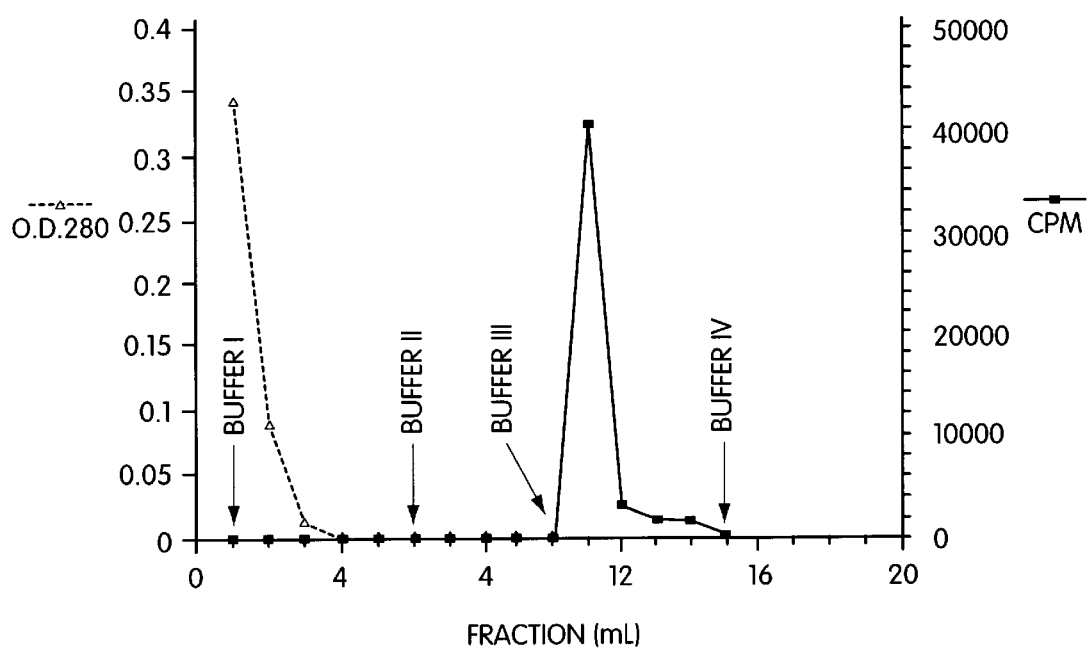
FIG. 1 is a graph depicting the elution profile of non-phosphorylated and phosphorylated peptides from a ferric column, demonstrating quantitative separation of non-phosphorylated peptides from phosphorylated peptides. The presence of non-phosphorylated peptides was determined by absorbance at 280 nm and the presence of phosphorylated peptides was determined by detection of an incorporated radiolabel. The phosphorylated peptides elute predominantly in fractions 11–14.
Figure 2A:
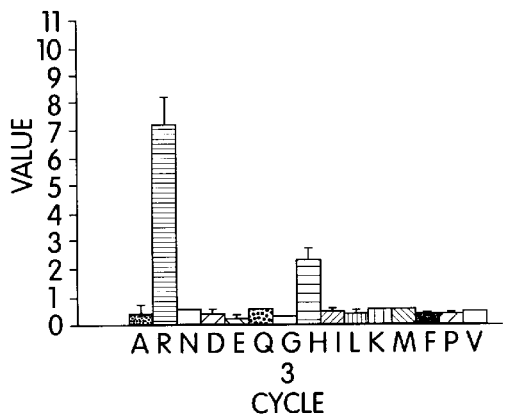
FIG. 2 is eight bar graphs depicting the relative abundance of each amino acid residue at each degenerate position of peptides from an oriented degenerate peptide library which are phosphorylated by protein kinase A. Each bar graph indicates the relative abundance of the 15 amino acid residues at a given cycle of sequencing. Cycle 7, the site of phosphorylation of the peptide, is not shown. Therefore, boxes A, B, C and D indicate amino acid preferences at −4, −3, −2 and −1 N-terminal of the phosphorylation site and boxes E, F, G and H indicate amino acid preferences at +1, +2, +3, and +4 C-terminal to the phosphorylation site. The amino acid residues are listed on the X-axis and relative abundance is on the Y-axis. The bars represent average values from two independent experiments.
Figure 2B:
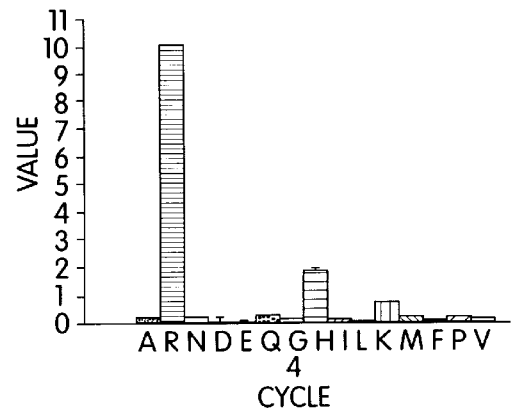
Figure 2C:
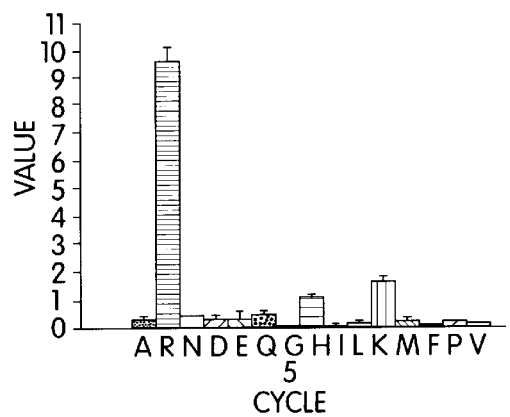
Figure 2D:
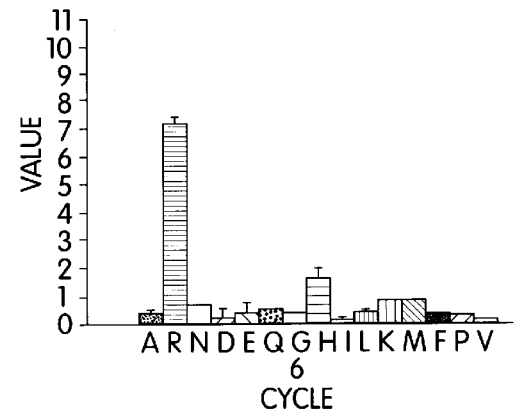
Figure 2E:
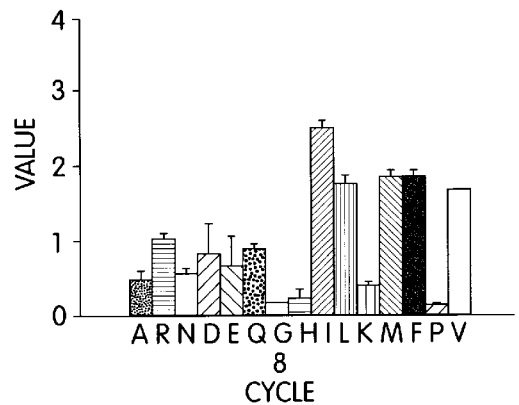
Figure 2F:
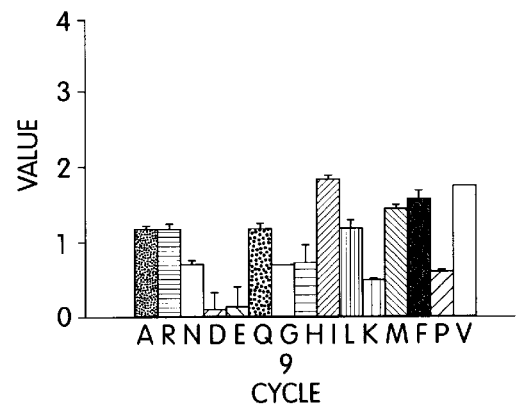
Figure 2G:
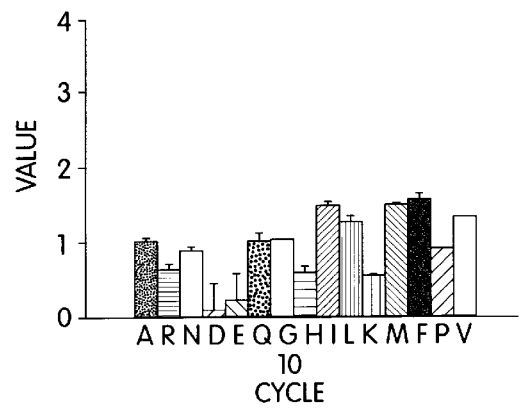
Figure 2H:
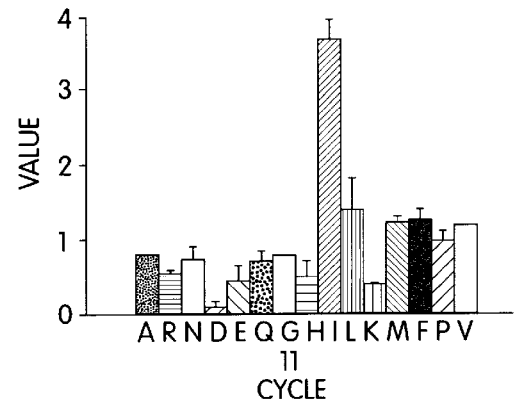
Figure 3A:
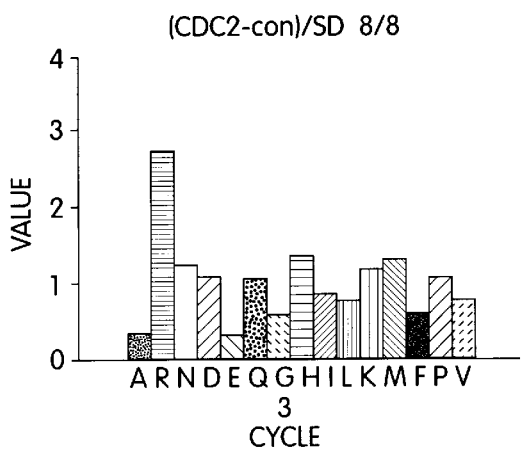
FIG. 3 is eight bar graphs depicting the relative abundance of each amino acid residue at each degenerate position of peptides phosphorylated by cyclin B/p33$^{cdc2}$. The data is plotted as described for FIG. 2.
Figure 3B:
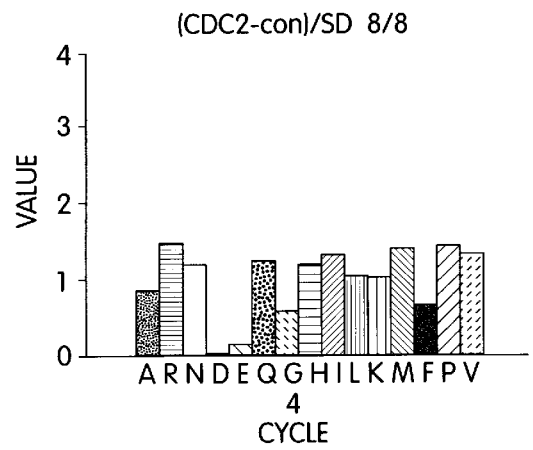
Figure 3C:
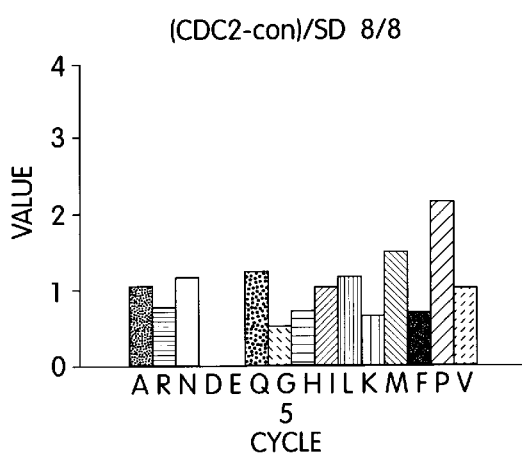
Figure 3D:
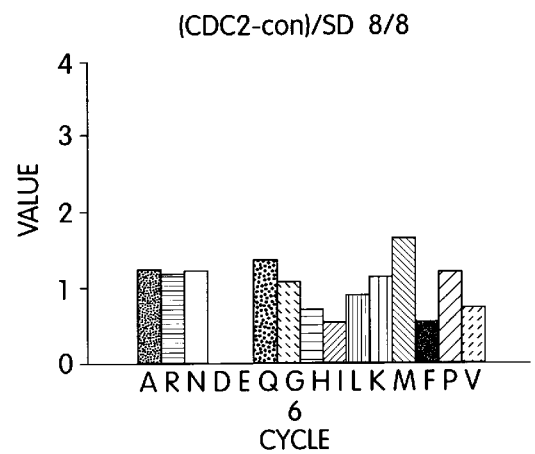
Figure 3E:
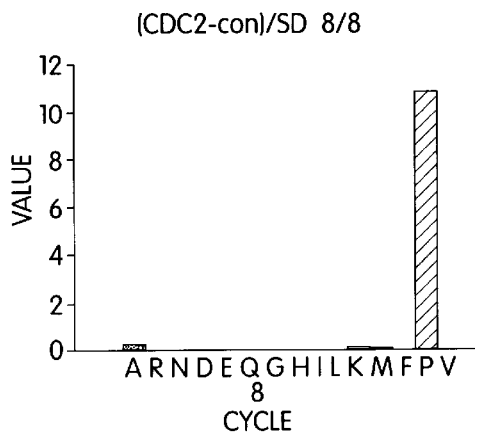
Figure 3F:
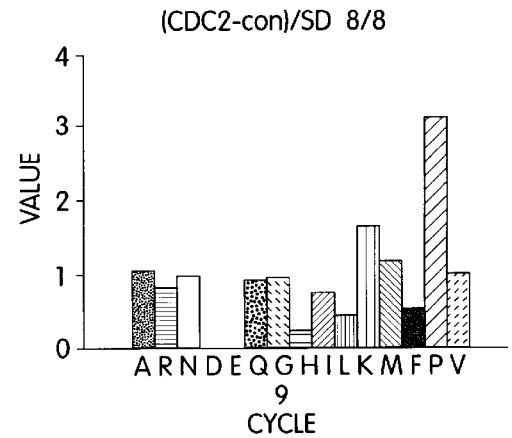
Figure 3G:
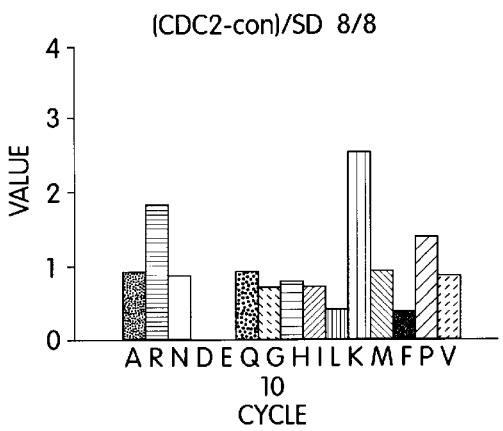
Figure 3H:
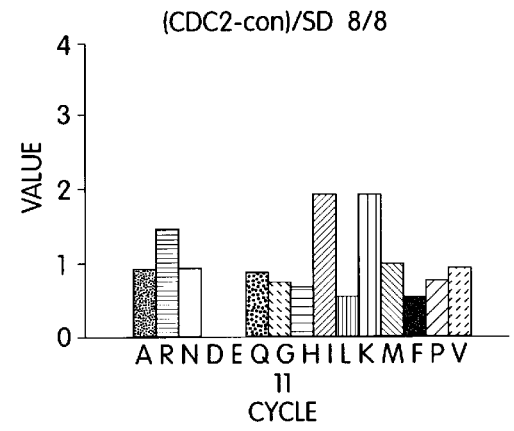
Figure 4A:
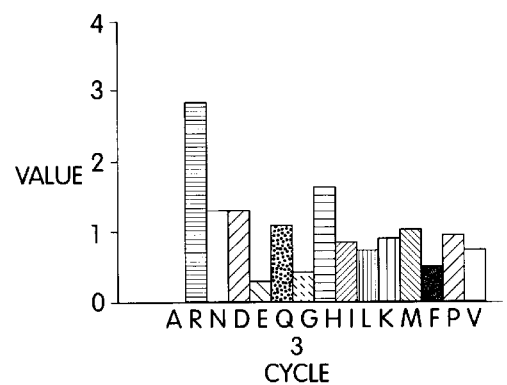
FIG. 4 is eight bar graphs depicting the relative abundance of each amino acid residue at each degenerate position of peptides phosphorylated by cyclin A/p33$^{CDK}$2. The data is plotted as described for FIG. 2.
Figure 4B:
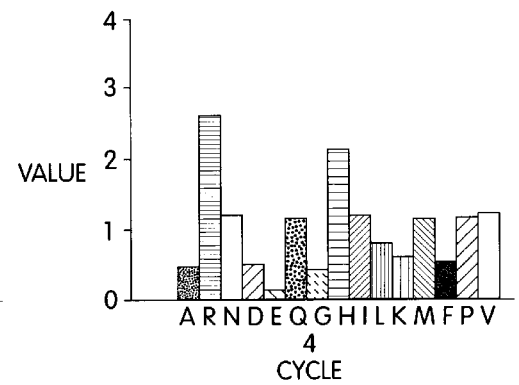
Figure 4C:
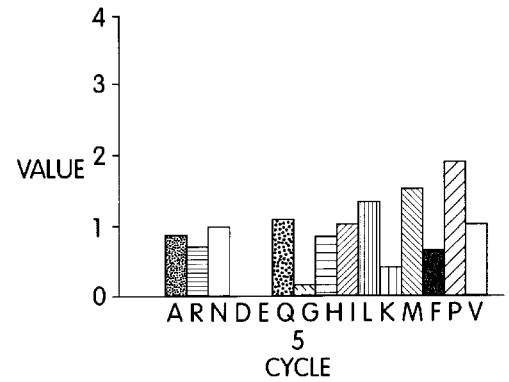
Figure 4D:
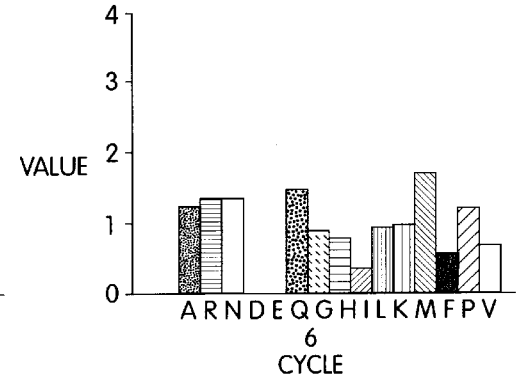
Figure 4E:
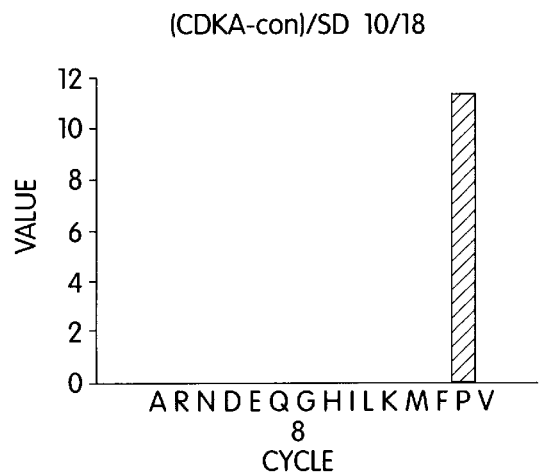
Figure 4F:
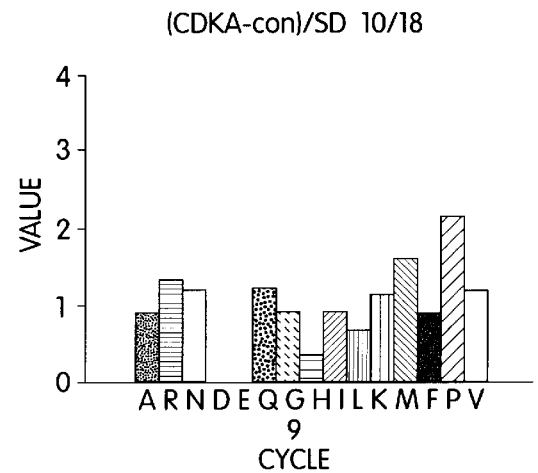
Figure 4G:
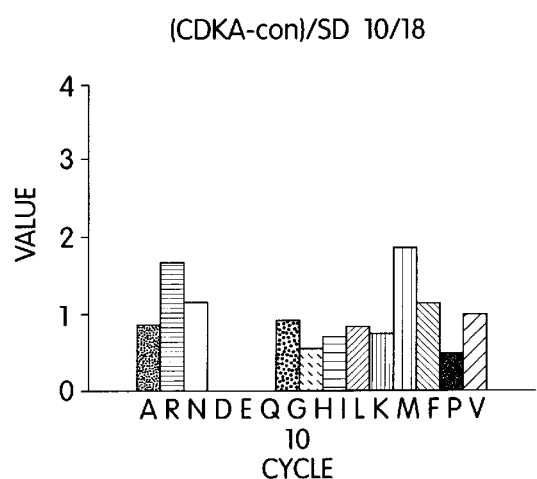
Figure 4H:
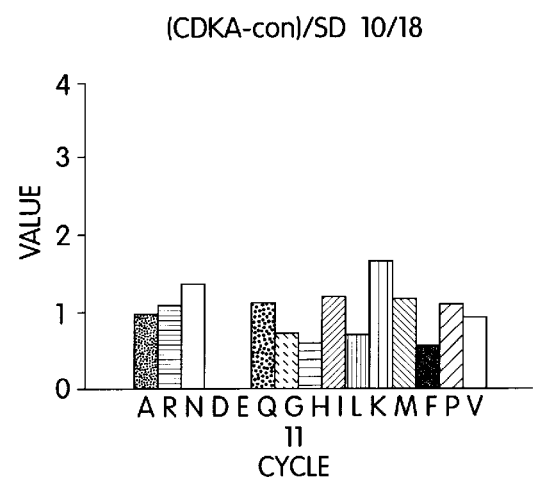
Figure 5A:
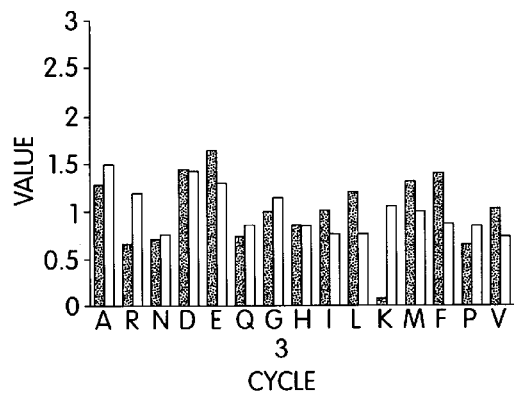
FIG. 5 is eight bar graphs depicting the relative abundance of each amino acid residue at each degenerate position of peptides phosphorylated by products of middle T/pp60$^{c\text{-}src}$ and pp60$^{v\text{-}src}$. The data is plotted as described for FIG. 2. The solid bars indicate the relative abundance of amino acids for products of pp60$^{v\text{-}src}$ and the stippled bars indicate the relative abundance of amino acids for products of middle T/pp60$^{c\text{-}src}$.
Figure 5B:
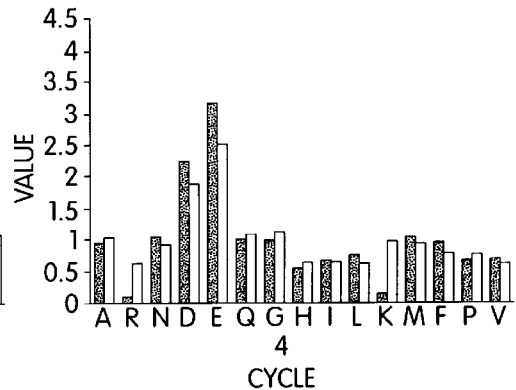
Figure 5C:
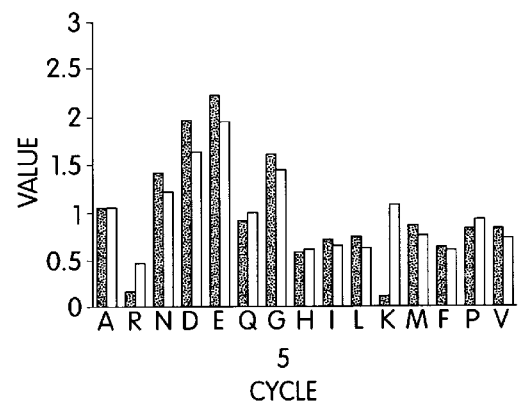
Figure 5D:
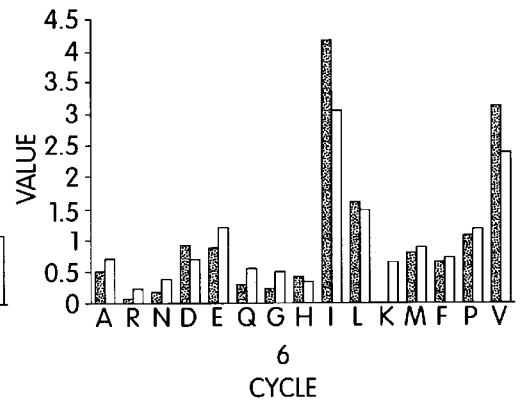
Figure 5E:
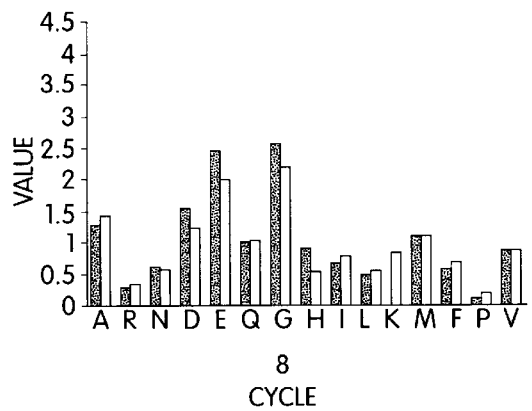
Figure 5F:
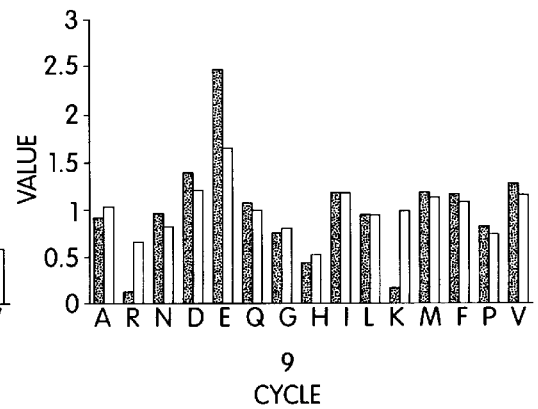
Figure 5G:
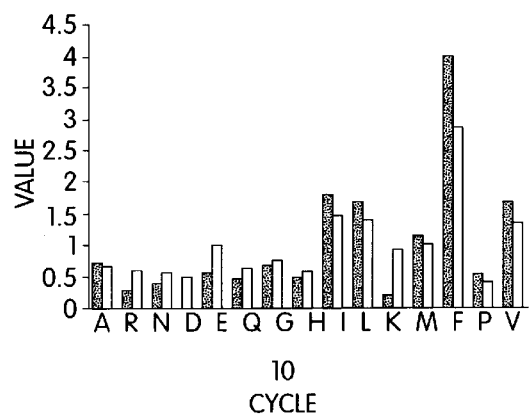
Figure 5H:
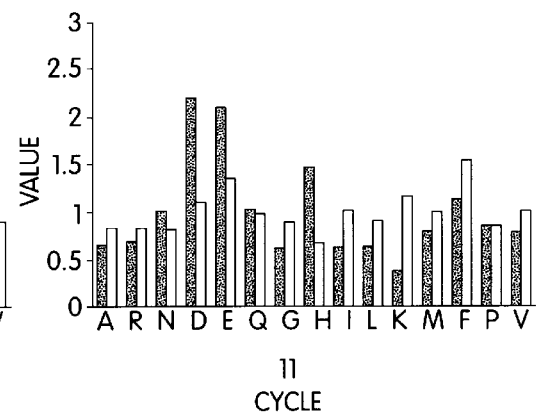
Figure 6A:
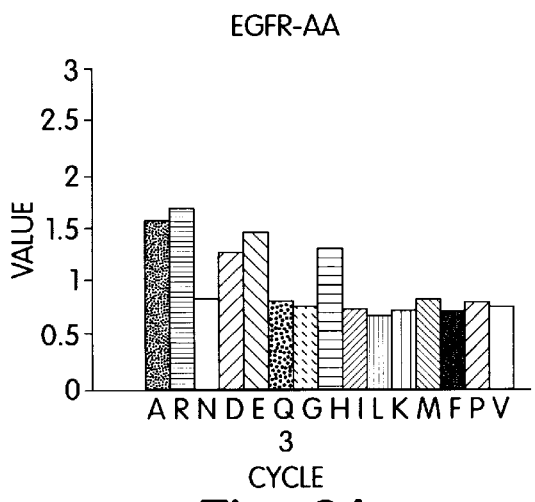
FIG. 6 is eight bar graphs depicting the relative abundance of each amino acid residue at each degenerate position of peptides phosphorylated by the epidermal growth factor receptor. The data is plotted as described for FIG. 2.
Figure 6B:
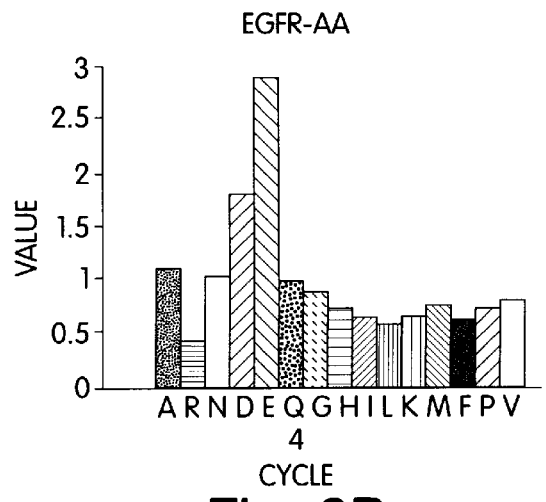
Figure 6C:
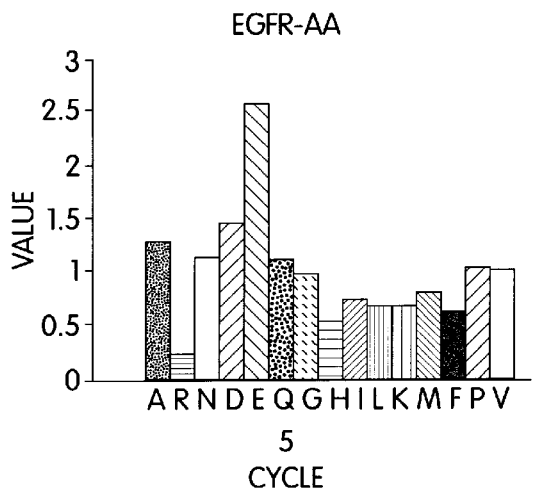
Figure 6D:
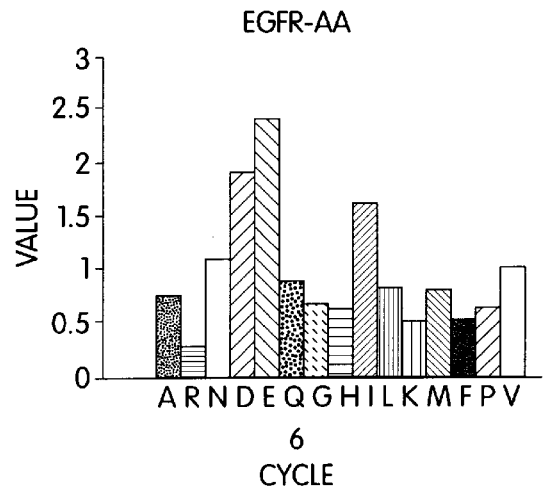
Figure 6E:
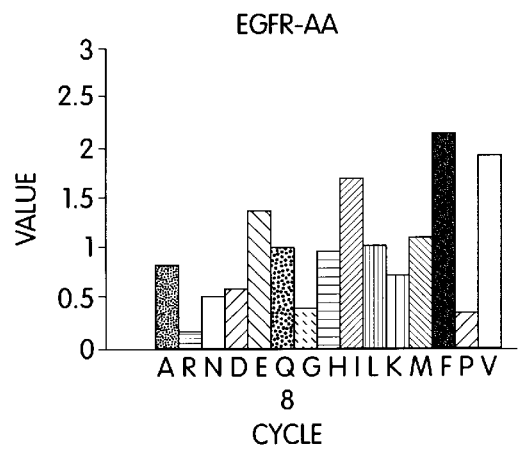
Figure 6F:
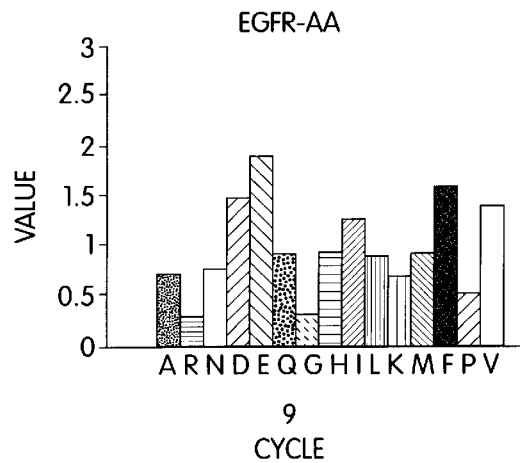
Figure 6G:
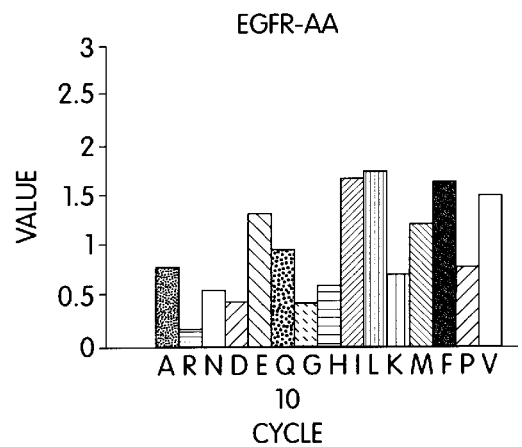
Figure 6H:
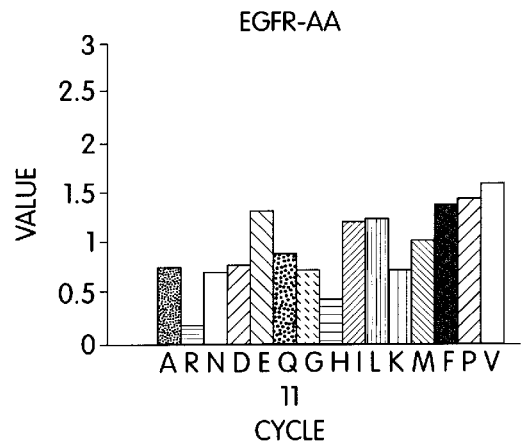
Figure 7A:
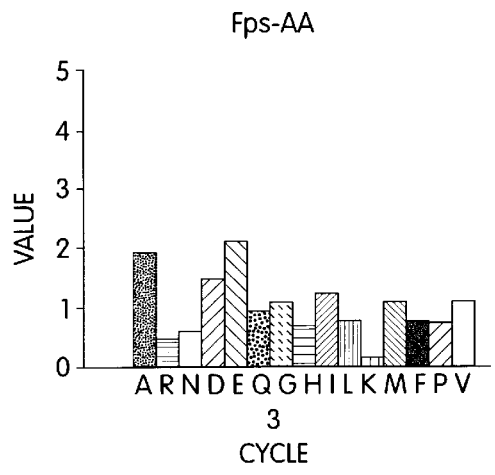
FIG. 7 is eight bar graphs depicting the relative abundance of each amino acid residue at each degenerate position of peptides phosphorylated by the pp95$^{c\text{-}fps/fes}$. The data is plotted as described for FIG. 2.
Figure 7B:
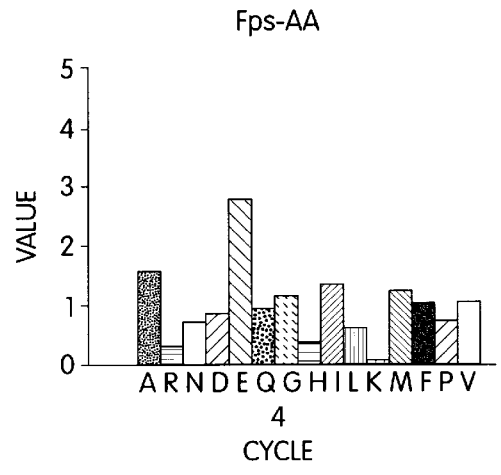
Figure 7C:
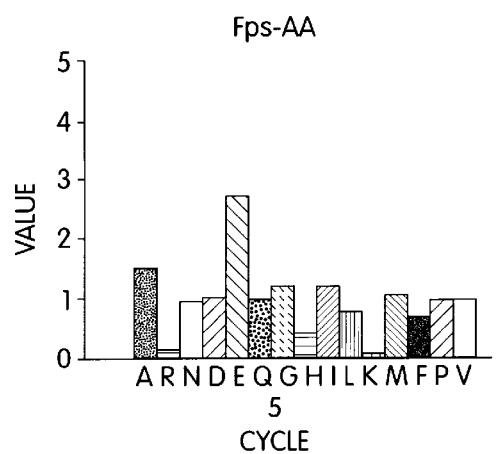
Figure 7D:
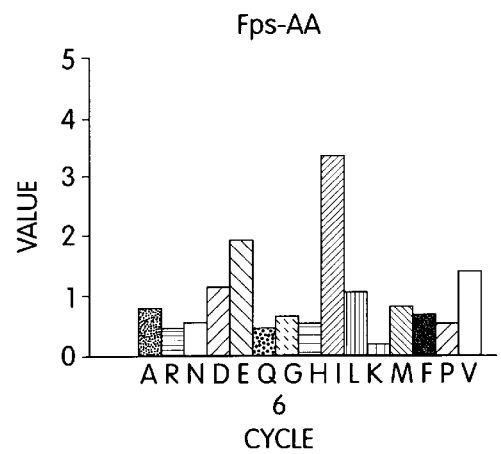
Figure 7E:
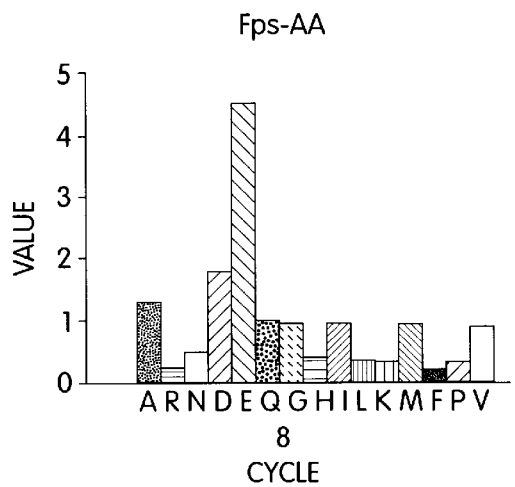
Figure 7F:
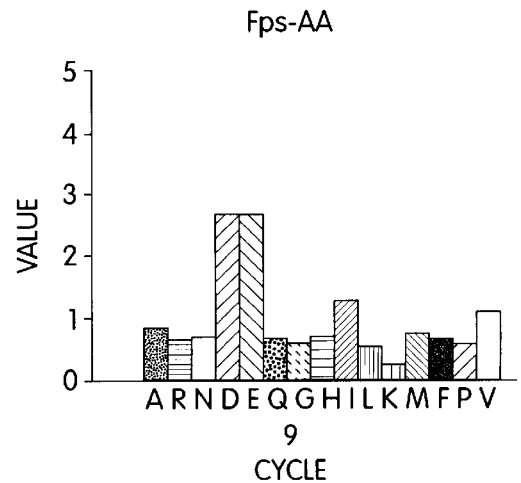
Figure 7G:
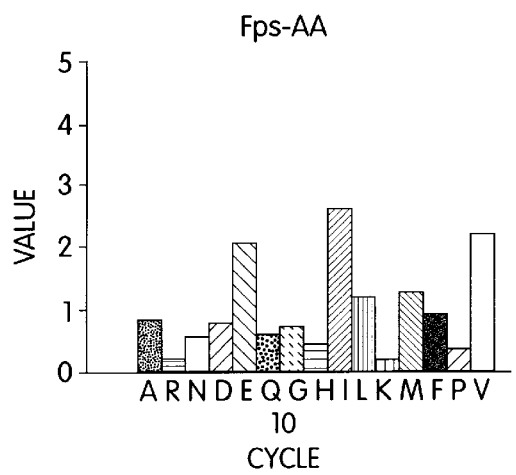
Figure 7H:
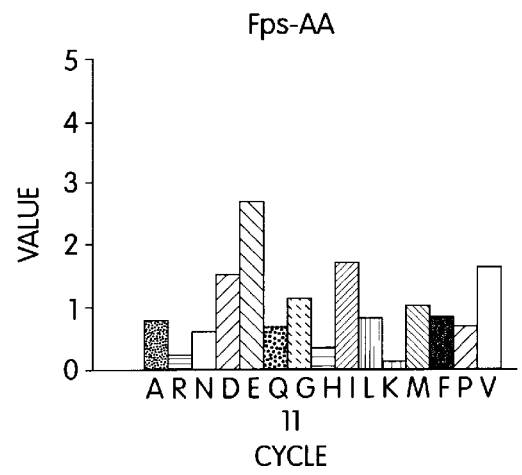

The following standard three-letter and one-letter abbreviations for amino acids are used throughout the application:

| | | |
|---|---|---|
| alanine | Ala | A |
| arginine | Arg | R |
| aspartic acid | Asp | D |
| asparagine | Asn | N |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrsine | Tyr | Y |
| valine | Val | V |

This invention pertains to the substrate specificity of protein kinases and to peptides which are substrates for protein kinases. The invention provides a method that allows for the identification of an amino acid sequence motif for the phosphorylation site of a specific protein kinase without having to identify, isolate and compare native substrates for the kinase. The method of the invention is based upon selection of a subpopulation of peptides from a degenerate peptide library that are substrates for a protein kinase. In the method, the peptides within a peptide library that can be substrates for a protein kinase are phosphoryated by the kinase, converting them to phosphopeptides. The phosphopeptides are then separated from the remaining non-phosphorylated peptides in the library, thereby isolating the subpopulation of peptides that are substrates for the kinase. This subpopulation of peptides is then sequenced and the relative abundance of each amino acid residue at each degenerate position of the peptides is determined. An amino acid sequence motif for the phosphorylation site of a protein kinase can be determined from the most abundant amino acid residues at each degenerate position of the peptides. This method has the advantage that it can be used to determine a phosphorylation site motif for any kinase, regardless of whether native substrates for that kinase have been identified. Furthermore, since the method involves selection of peptides which are phosphorylated most readily by a protein kinase, the determined amino acid sequence motif represents the optimal phosphorylation site for that kinase.

Based upon the amino acid sequence motif of the phosphorylation site of a kinase determined by the method of the invention, peptides can be made which are substrates for that particular protein kinase. Peptides comprising the most preferred amino acid residues of a sequence motif represent optimal substrates for the protein kinase. The peptide substrates of the invention can be used to detect and quantitate protein kinases. Furthermore, due to their high affinity for the catalytic site of a protein kinase, the peptide substrates of the invention can be used to competitively inhibit the activity of a protein kinase. Pseudosubstrates and peptide analogs can also be designed based upon the amino acid sequences of the peptide substrates of the invention.

The invention provides a method for determining an amino acid sequence motif for a phosphorylation site of a protein kinase. The phrase "an amino acid sequence motif for a phosphorylation site of a protein kinase" is intended to describe one or more amino acid sequences which represent a consensus sequence motif for the region including and surrounding an amino acid residue which is phosphorylated by a protein kinase. The method for determining an amino acid sequence motif for the phosphorylation site of a protein kinase first involves contacting a protein kinase to be examined with an oriented degenerate peptide library composed of non-phosphorylated peptides having a phosphorylatable amino acid residue at a fixed non-degenerate position. For a given kinase, only a small subset of the peptides have amino acids surrounding the phosphorylatable residue that create a preferred sequence for binding to the kinase and phosphorylation by the kinase. The protein kinase is allowed to phosphorylate the subset of peptides that are preferred substrates for the kinase, thereby converting this population of peptides to a population of phosphorylated peptides. Next, the population of phosphorylated peptides is separated from the remaining non-phosphorylated peptides. Finally, the mixture of phosphorylated peptides is subjected to sequencing (e.g., automated sequencing) and the abundance of each amino acid determined at each cycle of sequencing is compared to the abundance of each amino acid at the same cycle in the starting peptide library. Since the phosphorylated residue is at the same position in every peptide of the library (e.g., residue 7 from the N-terminus), the most abundant amino acid(s) at a particular cycle indicate the amino acid(s) preferred by the kinase at that position relative to the site of phosphorylation.

The term "protein kinase" as used herein is intended to include all enzymes which phosphorylate an amino acid residue within a protein or peptide. Preferred protein kinases for use in the method of the invention include protein-serine/threonine specific protein kinases, protein-tyrosine specific kinases and dual-specificity kinase. Other protein kinases which can be used in the method of the invention include protein-cysteine specific kinases, protein-histidine specific kinases, protein-lysine specific kinases, protein-aspartic acid specific kinases and protein-glutamic acid specific kinases. A protein kinase used in the method of the invention can be a purified native protein kinase, for example purified from a biological source. Some purified protein kinases are commercially available (e.g., protein kinase A from Sigma Chemical Co.). Alternatively, a protein kinase used in the method of the invention can be a recombinantly produced protein kinase. Many protein kinases have been molecularly cloned and characterized and thus can be expressed recombinantly by standard techniques. A recombinantly produced protein kinase which maintains proper kinase function can be used in the method of the invention. If the recombinant protein kinase to be examined is a eukaryotic protein kinase, it is preferable that the protein kinase be recombinantly expressed in a eukaryotic expression system to ensure proper post-translational modification of the protein kinase. Many eukaryotic expression systems (e.g., baculovirus and yeast expression systems) are known in the art and standard procedures can be used to express a protein kinase recombinantly. A recombinantly produced protein kinase can also be a fusion protein (i.e., composed of the protein kinase and a second protein or peptide, for example a protein kinase fused to glutathione-S-transferase (GST)) as long as the fusion protein retains the catalytic activity of the non-fused form of the protein kinase. Furthermore, the term "protein kinase" is intended to include portions of native protein kinases which retain catalytic activity. For example, a subunit of a multisubunit kinase which contains the catalytic domain of the protein kinase can be used in the method of the invention.

The term "degenerate peptide library" is intended to describe populations of peptides in which different amino acid residues are present at the same position in different peptides within the library. For example, a population of peptides of 10 amino acids in length in which the amino acid residue at position 5 of the peptides can be any one of the twenty amino acids would be a degenerate peptide library. A position within the peptides which is occupied by different amino acids in different peptides is referred to herein as a "degenerate position"; a position within the peptides which is occupied by the same amino acid in different peptides is referred to herein as a "non-degenerate position". The "oriented degenerate peptide library" used in the method of the invention is composed of non-phosphorylated peptides which have a phosphorylatable amino acid residue at a fixed, non-degenerate position. This means that the peptides contained within the library all have the same phosphorylatable amino acid residue at the same position within the peptides. The term "phosphorylatable amino acid residue" is intended to include those amino acid residues which can be phosphorylated by a protein kinase. Phosphorylatable amino acid residues include serine, threonine and tyrosine, or phosphorylatable analogs thereof.

In addition to the phosphorylatable non-degenerate amino acid residue, the peptides of the oriented degenerate peptide library have other amino acid residues which are degenerate. Preferably, the amino acid residues on either side of the phosphorylatable amino acid residue are degenerate (i.e, immediately N-terminal and C-terminal to the phosphorylated residue), thus enabling one to determine a phosphorylation site motif for the region surrounding the phosphorylated residue. For example, four amino acid residues located on each side of the phosphorylatable amino acid residue can be degenerate (e.g., at positions −4, −3, −2, −1, +1, +2, +3 and +4 relative to a phosphorylated amino acid residue at position 0 can be degenerate). The degenerate positions in the peptides of an oriented degenerate peptide library can be created such that any one of the twenty amino acids can occupy those positions. However, in order to reduce "background" phosphorylation events (i.e, phosphorylation events at a residue other than the fixed phosphorylatable residue) it is preferred that the degenerate positions not contain amino acid residues that can be phosphorylated by the particular protein kinase being examined. Thus, for protein-serine/threonine kinases it is preferred that the degenerate positions not contain serine or threonine. Likewise, for a protein-tyrosine specific kinase, it is preferred that the degenerate positions not contain tyrosine and for a dual-specificity kinase is it preferred that the degenerate positions not contain serine, threonine or tyrosine.

However, an oriented degenerate peptide library which contains additional phosphorylatable residues to the fixed residue can be used and it is possible to estimate the degree of background which will occur when using such a library and take this background into consideration when evaluating the results of the library screening. For example, consider the problem of including Tyr at the degenerate positions of a library having 8 degenerate positions that is to be used with a protein-Tyr kinase. The kinase may phosphorylate the tyrosine residues at the degenerate positions as well as the Tyr at the fixed position. The theoretical fraction of peptides with Tyr at one of the degenerate sites in addition to the fixed site (assuming a degeneracy of 20 at each residue) is $8 \times (1/20) = 0.4$. Thus, about 40% of the phosphopeptides purified are likely to be phosphorylated at the wrong residue. It is possible to get a good estimate of the extent of this problem since those peptides that are phosphorylated at sites other than the fixed residue will have detectable non-phosphorylated Tyr at the sequencing cycle corresponding to the fixed residue when the sequencing is performed on the mixture. Although these phosphopeptides will cause a background problem when the data are plotted, the problem is less serious than initially implicated from the 40% contamination assumed. For example, consider the case in which the protein-tyrosine kinase being evaluated phosphorylates the sequence Glu-Xxx-Tyr and the fixed Tyr is at position 7 in the peptides. Those peptides with Glu at position 5 will be preferentially phosphorylated. However, peptides with Glu at position 3 and Tyr at position 5 will also be phosphorylated and appear in the mixture. Similarly, those with Glu at 4 and Tyr at 6, Glu at 6 and Tyr at 8, Glu at 8 and Tyr at 10 and Glu at 9 and Tyr at 11 will also be selected. Each of these subfamilies of peptides is far less abundant than the group with Tyr fixed at position 7 (in theory, $1/20$th). Thus, the expected result is that Glu will be very abundant at cycle 5 but will also be somewhat elevated ($1/20$th as much as in cycle 5) at cycles 3, 4, 6, 8, and 9. In general this background is unlikely to be a problem. The importance of re-evaluating protein kinases with phosphorylatable residues at the degenerate positions is that Ser, Thr or Tyr residues upstream or downstream of the phosphorylated residue are already known to be important for some protein kinases.

Additionally, certain amino acid residues may be omitted from a degenerate position in a degenerate peptide library for practical reasons. For example, tryptophan and cysteine residues may be omitted from the degenerate positions because there can be problems with detecting these residues during amino acid sequencing and cysteine residues may cause peptide dimer formation. However, a peptide library containing Trp and Cys at a degenerate position can be used in the method of the invention. For example, a "second generation" library can be made based upon the amino acid sequence motif determined from initially screening a protein kinase with a peptide library which does not contain Trp or Cys at degenerate positions. At each degenerate position of this library, the peptides would have either the preferred amino acid residue determined from the initial screening or Cys or Trp. Thus, in this library, rather than being 1 of 20 possible residues at the degenerate position, Cys and Trp would be 1 of 3 possible residues at the degenerate position. Therefore, Trp and Cys will have a much stronger signal during amino acid sequencing of the peptides, thereby allowing for detection of these residues and for evaluation of their influence on the amino acid sequence motif of the phosphorylation site.

A preferred type of oriented degenerate peptide library for use in the method of the invention is a soluble synthetic peptide library. The term "soluble synthetic peptide library" is intended to mean a population of peptides which are constructed by in vitro chemical synthesis, for example using an automated peptide synthesizer, and which are not connected to a solid support such as a bead or a cell. For general descriptions of the construction of soluble synthetic peptide libraries see for example Houghten, R. A., et al., (1991) *Nature* 354:84–86 and Houghten, R. A., et al., (1992) *BioTechniques* 13:412–421. Standard techniques for in vitro chemical synthesis of peptides are known in the art. For example, peptides can be synthesized by (benzotriazolyloxy)tris(dimethylamino)-phosphonium hexafluorophosphate (BOP)/1-hydroxybenzotriazole coupling protocols. Automated peptide synthesizers are commercially available (e.g., Milligen/Biosearch 9600). To create degenerate positions within peptides of a soluble synthetic peptide library, two approaches can be used. A preferred approach is to divide the resin upon which the peptides are synthesized into equivalent portions and then couple each aliquot to a different amino acid residue to create a degenerate position. After this coupling, the resin aliquots are recombined and the procedure is repeated for each degenerate position. This approach results in approximately equivalent representation of each different amino acid residue at the degenerate position. Alternatively, a mixture of different amino acid residues can be added to a coupling step to create a degenerate position. However, different amino acid residues have different coupling efficiencies and therefore if equal amounts of each amino acid are used, each amino acid residue may not be equivalently represented at the degenerate position. The different coupling efficiencies of different amino acids can be compensated for by using a "weighted" mixture of amino acids at a coupling step, wherein amino acids with lower coupling efficiencies are present in greater abundance than amino acids with higher coupling efficiencies. A procedure for constructing a soluble synthetic degenerate peptide library which can be used in the method of the invention is described in detail in Example 1.

An alternative type of oriented degenerate peptide library which can be used in the method of the invention is a solid-support bound peptide library. The term "solid-support bound peptide library" is intended to mean a population of peptides which are connected to a solid support such as a bead or plastic pin. For general descriptions of the construction of solid-support bound peptide libraries see for example Geysen, H. M., et al. (1986) *Mol. Immunol.* 23:709–715; Lam, K. S., et al. (1991) *Nature* 354:82–84; and Pinilla, C., et al. (1992) *BioTechniques* 13:901–905. For this type of library, the peptides are synthesized attached to the solid support, such as a bead, and degenerate positions are created by splitting the population of beads, coupling different amino acids to different subpopulations and recombining the beads. The final product is a population of beads each carrying many copies of a single unique peptide. Thus, this approach has been termed "one bead/one peptide".

Another alternative type of oriented degenerate peptide library which can be used in the method of the invention is a phage expression library. The term "phage expression library" is intended to mean a population of filamentous bacteriophage particles which express a library of peptides on their surface wherein each phage particle expresses a different peptide. For general descriptions of the construction of phage expression libraries see for example Scott, J. K and Smith, G. P. (1990) *Science* 249:386–390; Cwirla, S. E., et al. (1990) *Proc. Natl. Acad. Sci. USA* 87:6378–6382; and Felicia, F., et al. (1991) *J. Mol Biol.* 222:301–310. A phage expression library is based upon the expression by the phage of peptides encoded by nucleic acid introduced into the phage. Degenerate positions in the peptides are created by inserting degenerate nucleic acid sequences, i.e., nucleic acids which have different nucleotides at the same position in different nucleic acid molecules. Degenerate nucleic acid sequences can be made by standard techniques known in the art. When using a phage expression library, the amino acid sequences of peptides selected during a screening process are determined by sequencing the inserted nucleic acid and thereby deducing the amino acid sequence of the encoded peptides.

A soluble synthetic peptide library is preferred for use in the method of the invention because the bulk population of isolated phosphorylated peptides can be sequenced simultaneously, thus directly providing information on the relative abundance of different amino acid residues at each degenerate position within the population of peptides. In contrast, if a solid-support bound library or a phage expression library is used, each isolate gives only the single amino acid sequence of that isolated peptide and therefore many isolated peptides must be individually sequenced before one can arrive at a consensus motif. Even then, it is not possible to predict the order of affinities of the various peptides isolated unless they are individually synthesized and compared in binding experiments. One cannot be certain that one has not missed the best possible motif because not enough isolated peptides were sequenced. In addition, while the soluble synthetic oriented peptide library provides predictions about substitutions that would severely reduce the affinity of the peptide, no such information can be obtained from a solid-support bound library or a phage expression library.

It has been estimated that approximately 9 to 12 amino acids of a substrate peptide are likely to contact the active site cleft of a kinase, based upon mutagenesis studies of known consensus motifs for phosphorylation sites of certain protein kinases and from X-ray crystallographic studies of peptides bound to protein kinases. Accordingly, an oriented degenerate peptide library can be used in which the degenerate residues encompass the region likely to contact the active site cleft of the kinase. The number of amino acids residues surrounding the phosphorylated residue of a substrate that influence the substrate specificity of a kinase is likely to differ for different kinases (again based upon mutagenesis studies of known consensus motifs for certain kinases). Thus, it is expected that oriented degenerate peptide libraries which will be useful in the method of the invention may have as few as one degenerate amino acid residue on either side of the phosphorylated residue or as many as ten degenerate amino acid residues on either side of the phosphorylated residue. A preferred number of degenerate residues on either side of the phosphorylation site is four (corresponding to positions −1, −2, −3 −4, +1, +2, +3 and +4 relative to the phosphorylated residue). Alternative to having an equal number of degenerate residues on either side of the phosphorylated residue, one can use a library which has unequal numbers of degenerate residues on either side of the phosphorylated residue (e.g., 2 on one side and 4 on the other, etc.). The diversity of the peptide library (i.e., the number of different peptides contained within the library) is a function of the number of degenerate residues: the greater the number of degenerate residues the greater the diversity. For example, a library in which only 2 positions are degenerate and any amino acid can be at these degenerate positions would represent 400 unique peptides ($20^2$) whereas a library in which 8 positions are degenerate and any amino acid can be at these positions would represent approximately $2.5 \times 10^{10}$ unique peptides ($20^8$).

In one embodiment of the invention, the oriented degenerate peptide library is composed of peptides having a formula:

$$(Xaa)_n\text{-Zaa-}(Xaa)_m \text{ (SEQ ID NO: 1)}$$

wherein Zaa is a non-degenerate phosphorylatable amino acid selected from Ser, Thr and Tyr, Xaa is any amino acid and n and m are integers from 1–10 inclusive. Thus, $(Xaa)_n$ and $(Xaa)_m$ can be degenerate residues and there are between 1 and 10 residues (not all of which are required to be degenerate) on either side of the non-degenerate phosphorylatable residue.

In a preferred embodiment of the invention, the phosphorylatable amino acid residue at the fixed non-degenerate position is the only phosphorylatable amino acid residue in the non-phosphorylated peptides comprising the peptide library. Peptide libraries can be constructed in which the type of amino acid residue(s) which a kinase phosphorylates is omitted at the degenerate position(s). Accordingly the invention provides oriented degenerate peptide libraries composed of peptides having a formula: $(Xaa)_n$-Zaa-$(Xaa)_m$ that have certain amino acids omitted from the degenerate position(s). In the case where the protein kinase is a protein-serine/threonine specific kinase, the library comprises peptides wherein Zaa is a non-degenerate phosphorylatable amino acid selected from Ser and Thr and Xaa is any amino acid except Ser and Thr. In the case where the protein kinase is a protein-tyrosine specific kinase, the library comprises peptides wherein Zaa is Tyr and Xaa is any amino acid except Tyr. In the case where the protein kinase is a dual-specificity kinase, a protein-serine/threonine specific kinase or a protein-tyrosine specific kinase, the library comprises peptides wherein Zaa is a non-degenerate phosphorylatable amino acid selected from Ser, Thr and Tyr, and Xaa is any amino acid except Ser, Thr and Tyr.

A peptide library comprising peptides comprising the formula $(Xaa)_n$-Zaa-$(Xaa)_m$, (wherein Zaa is a non-degenerate phosphorylatable amino acid, Xaa is any amino acid and n and m are integers from 1–10 inclusive), can be contained within a larger peptide or within a protein. For example, when a phage expression library is used, the peptide encompassing the phosphorylatable amino acid residue and the surrounding degenerate amino acid residues is contained within a phage protein expressed on the surface of the phage (i.e., the degenerate peptides are part of a fusion protein comprising the phage particle protein and the peptide inserts of the library). Additionally, for soluble synthetic peptide libraries, it may be desirable to add additional amino acid residues to one or both ends of the degenerate region of the peptides. Non-degenerate amino acids residues N-terminal to the degenerate region of the peptides can serve to verify that peptides from the peptide mixture are being sequenced properly and can be used to quantitate the amount of peptides present. Similarly, non-degenerate amino acid residues C-terminal to the degenerate region of the peptides can be used for quantification purposes. The addition of a poly-lysine tail to the C-terminal end of the peptides of the library can prevent wash-out of peptides during automated sequencing and improve the solubility of the peptide mixture.

Another embodiment of the peptide library of the invention specifically allows for the addition of non-degenerate amino acids at the N-terminal and/or C-terminal ends of the degenerate region of the peptides. In this embodiment, the oriented degenerate peptide library comprises non-phosphorylated peptides comprising a formula:

$Y_1$-$(Xaa)_n$-Zaa-$(Xaa)_m$-$Y_2$ (SEQ ID NO: 2)

wherein

Zaa is a non-degenerate phosphorylatable amino acid selected from the group consisting of Ser, Thr and Tyr, Xaa is any amino acid, n and m are integers from 1–10 inclusive, $Y_1$ is hydrogen or a peptide having a formula $(Xaa)_a$ wherein Xaa is any non-degenerate amino acid and a is an integer from 1–15 inclusive, and $Y_2$ is hydrogen or a peptide having a formula $(Xaa)_b$ wherein Xaa is any non-degenerate amino acid and b is an integer from 1–15 inclusive.

This library encompasses peptides up to a length of 51 amino acids. Alternatively, a and b can be integers from 1–10 inclusive. This library encompasses peptides up to a length of 41 amino acids. Alternatively, a and b can be integers from 1–5 inclusive. This library encompasses peptides up to a length of 31 amino acids.

In yet another embodiment, the invention provides an oriented degenerate peptide library comprising non-phosphorylated peptides comprising a formula (SEQ ID NO:3):

Met-Ala-Xaa1-Xaa2-Xaa3-Xaa4-Xaa5-Xaa6-Xaa7-Xaa8-Xaa9-Ala-Lys-Lys-Lys wherein Xaa1, Xaa2, Xaa3, Xaa4, Xaa6, Xaa7, Xaa8 and Xaa9 are any amino acid residue and Xaa5 is selected from Ser, Thr and Tyr.

An oriented degenerate peptide library provided by the invention is contacted with a protein kinase under conditions which allow for phosphorylation of a substrate by the protein kinase and the kinase is allowed to phosphorylate peptides within the oriented degenerate peptide library having a preferred sequence for phosphorylation by the protein kinase, thereby forming a population of phosphorylated peptides. The phrase "contacted under conditions which allow for phosphorylation of a substrate by the protein kinase" is intended to include any form of combining or incubating together of the kinase and the library under conditions which enable phosphorylation of substrate proteins or peptides by the kinase. Thus, these conditions will include the presence of ATP (or an ATP analogue) as a phosphate donor molecule (or analogue thereof). The phosphate of the phosphate donor molecule can be labeled, e.g., radiolabeled, to label peptides which become phosphorylated by the kinase (e.g., to allow for their detection by detecting the radiolabel). For example, $^{32}$P-γ-ATP can be used as the phosphate donor. Preferred conditions for contacting the kinase with the library are described in detail in Example 2.

Following phosphorylation of phosphorylatable peptides within the oriented degenerate peptide library, the phosphorylated peptides are separated from the remaining non-phosphorylated peptides of the library. A preferred method for separating phosphorylated peptides from non-phosphorylated peptides is by binding the phosphorylated peptides to a ferric column. This type of column has been used previously to separate tryptic phosphopeptide fragments of phosphorylated proteins from non-phosphorylated tryptic fragments (Muszynska et al., (1986) *Biochem.* 25: 6850–6853; Muszynska et al., (1992) *J. Chromatography* 604:19–28). However, previously described protocols could not be used because the phosphopeptide were eluted from the column in such a way that they could not then be sequenced, which is the necessary subsequent step in the procedure (i.e., the washing and elution buffers were incompatible with subsequent sequencing of the phosphopeptides). The column washing and elution conditions were modified to allow for subsequent sequencing of the eluted phosphopeptides. In the modified procedure, the peptide mixture is loaded onto the column in high salt buffer of about pH 5.5–6.0 (e.g., 50 mM MES, 1 M NaCl, pH 5.5). In this buffer, phosphorylated peptides bind to the column whereas non-phosphorylated peptides flow through the column. Next, the column is washed with a very low salt buffer of about pH 6.0 (e.g., 2 mM MES, pH 6.0) to remove contaminating non-phosphorylated peptides and excess salt from the column. Finally, the phosphopeptides are eluted from the column with a buffer of about pH 8.0 (e.g., 500 mM $NH_4CO_3$, pH 8.0). A procedure for quantitative separation of phosphorylated peptides from non-phosphorylated peptides using a ferric column is described in detail in Example 3.

Alternatively, since many protein kinases are known to be capable of using ATP-γ-S as a thio-phosphate donor to phosphorylate proteins and peptides, a mercury (Hg2+) column (pChloromercuribenzoate-Agarose: Pierce) could be used for separating thio-phosphorylated peptides from non-phosphorylated peptides. Such columns have been used in the past to bind thio-phosphorylated nucleotides and peptides (Sun, I. Y-C., and Allfrey, V. G. (1982) *J. Biol. Chem.* 257:1347–1353 and Sun et al., (1980) *J. Biol. Chem.* 255:742–747). Since any thiol group will bind to the mercury column, Cys cannot be present in the library if the mercury column is used. Also, the kinase reaction is typically about 5 fold slower with ATP-γ-S so more enzyme or a longer incubation time is likely to be necessary.

The use of a mercury column to separate thio-phosphorylated peptides from non-thio-phosphorylated peptides can allow for the inclusion of phosphotyrosine, phosphoserine or phosphothreonine at degenerate positions in the library. In this case, many peptides within the library would be phosphorylated during the synthesis of the library and the kinase reaction would then be performed with ATP-γ-S as a thio-phosphate donor to thiophosphorylate substrates of the kinase. The thiophosphorylated peptides would then be separated from the non-thio-phosphorylated peptides with a mercury column.

Another theoretical alternative approach to separating phosphorylated peptides from non-phosphorylated peptides is to use an antibody-affinity column. For example, an anti-phosphotyrosine antibody-column could be used to separate peptides phosphorylated on tyrosine from non-phosphorylated peptides. However, because anti-phosphotyrosine antibodies have some specificity for the amino acid residues surrounding the phosphorylated tyrosine, the antibody column would impose additional selection on the mixture of phosphorylated peptides. Thus, it is likely that some peptides which can be substrates for the kinase (i.e., a proportion of the phosphorylated peptide mixture) will be lost during the column separation step, thereby artifactually altering the mixture of peptides which is sequenced.

Prior to the step of separating the phosphorylated (or thio-phosphorylated) peptides from non-phosphorylated peptides, additional purification steps may be added to remove other components of the kinase reaction, such as the kinase itself and the free phosphate donor. For example, the kinase can be bound to a solid support, such as a bead, during the kinase reaction and then the supernatant, containing the phosphorylated and non-phosphorylated peptides can be removed, thereby separating the kinase from the peptide. Chromatography can be used to separate the free phosphate donor (e. g, ATP) from the peptides, for example a DEAE column can be used.

After the phosphorylated peptides are separated from non-phosphorylated peptides, the amino acid sequences of the phosphorylated peptides are determined. Preferably, the oriented degenerate peptide library used is a soluble synthetic peptide library and the phosphorylated peptides are sequenced as a bulk population using an automated peptide sequencer (alternatively, manual sequencing could be performed). This approach provides information on the abundance of each amino acid residue at a given cycle in the sequence of the phosphopeptide mixture, most importantly at the degenerate positions. For each degenerate position in the peptides of the library, a relative abundance value can then be calculated by dividing the abundance of a particular amino acid residue at that position after library screening (i.e., after peptide phosphorylation and separation) by the abundance of the same amino acid residue at that position in the starting library. Thus, the relative abundance (RA) of an amino acid residue Xaa at a degenerate position in a peptide can be defined as:

$$RA = \frac{\text{amount of Xaa in the population of phosphorylated peptides}}{\text{amount of Xaa in the oriented degenerate peptide library}}$$

The relative abundance value may be corrected for background contamination as described in Example 4. Amino acid residues which are neither enriched for nor selected against in the population of peptides which can serve as substrates for the kinase (i.e., the phosphorylated peptides) will have a relative abundance of 1.0. Those amino acid residues which are preferred at a particular degenerate position (i.e., residues which are enriched at that position in the phosphorylated peptides) will have a relative abundance greater than 1.0. Those amino acid residues which are not preferred (i.e., residues which are selected against at that position in the phosphorylated peptides) will have a relative abundance less than 1.0. Based upon the relative abundance values for each amino acid residue at a degenerate position, preferred amino acid residues, i.e., amino acid residues with a relative abundance greater than 1.0, can be identified at that position.

As discussed above, if a solid-support bound library or a phage expression library is used, each isolate must be sequenced individually (each individual isolated "bead" for the solid support bound library or each individual nucleic acid insert for each phage particle, wherein the peptide sequence is deduced from the amino acid sequence). This requires sequencing of large numbers of isolates and would likely provide only an estimation of the relative abundance of each amino acid residue at a degenerate position.

Based upon the relative abundance of different amino acid residues at each degenerate position within the population of phosphorylated peptides, an amino acid sequence motif for a phosphorylation site of the protein kinase can be determined. The amino acid sequence motif encompasses the degenerate region of the peptides. The particular amino acid residues chosen for the motif at each degenerate position are those which are most abundant at each position. Thus, an amino acid residue(s) with a relative abundance value greater than 1.0 at a particular position can be chosen as the amino acid residue(s) at that position within the amino acid sequence motif. Alternatively, a higher relative abundance value can be used as the basis for inclusion of an amino acid residue to create an even more preferred phosphorylation site for a kinase. For example, an amino acid residue(s) with a relative abundance value equal to or greater than 1.5 at a particular position can be chosen as the amino acid residue (s) at that position within the amino acid sequence motif.

The analysis of data obtained from sequenced phosphorylated peptides is described in more detail in Example 4 and determinations of amino acid sequence motifs for seventeen known protein kinases are described in detail in Examples 5–9 and 11–12.

The method of the invention can be used to determine an amino acid sequence motif for the phosphorylation site of any kinase. For example, the kinase can be a protein-serine/threonine specific kinase (in which case a library with a fixed non-degenerate serine or threonine is used), a protein-tyrosine specific kinase (in which case a library with a fixed non-degenerate tyrosine is used) or a dual-specificity kinase (in which case a library with either a fixed non-degenerate serine, threonine or tyrosine can be used). Examples of protein kinases which are encompassed by the invention can be found in Hanks et al. (1988) *Science* 241:42–52.

Protein-serine/threonine specific kinases encompassed by the invention include: 1) cyclic nucleotide-dependent kinases, such as cyclic-AMP-dependent protein kinases (e.g., protein kinase A) and cyclic-GMP-dependent protein kinases; 2) calcium-phospholipid-dependent kinases, such as protein kinase C; 3) calcium-calmodulin-dependent kinases, including CaMII, phosphorylase kinase (PhK), myosin light chain kinases (e.g., MLCK-K, MLCK-M), PSK-H1 and PSK-C3; 4) the SNF1 family of protein kinases (e.g., SNF 1, nim1, KIN1 and KIN2); 5) casein kinases (e.g., CKII); 6) the Raf-Mos proto-oncogene family of kinases, including Raf, A-Raf, PKS and Mos; and 7) the STE7 family of kinases (e.g. STE7 and PBS2). Additionally, the protein-serine/threonine specific kinase can be a kinase involved in cell cycle control. Many kinases involved in cell cycle control have been identified. Cell cycle control kinases include the cyclin dependent kinases, which are heterodimers of a cyclin and kinase (such as cyclin B/p33$^{cdc2}$, cyclin A/p33$^{CDK2}$, cyclin E/p33$^{CDK2}$ and cyclin D1/p33$^{CDK4}$). Other cell cycle control kinases include Wee1 kinase, Nim1/Cdr1 kinase, Wis1 kinase and NIMA kinase.

Protein-tyrosine specific kinases encompassed by the invention include: 1) members of the src family of kinases, including pp60$^{c-src}$, pp60$^{v-src}$, Yes, Fgr, FYN, LYN, LCK, HCK, Dsrc64 and Dsrc28; 2) members of the Abl family of kinases, including Abl, ARG, Dash, Nabl and Fes/Fps; 3) members of the epidermal growth factor receptor (EGFR) family of kinases, including EGFR, v-Erb-B, NEU and DER; 4) members of the insulin receptor (INS.R) family of growth factors, including INS.R, IGF1R, DILR, Ros, 7less, TRK and MET; 5) members of the platelet-derived growth factor receptor (PDGFR) family of kinases, including PDGFR, CSF1R, Kit and RET.

Other protein kinases which can be used in the method of the invention include syk, ZAP70, Focal Adhesion Kinase, erk1, erk2, erk3, MEK, CSK, BTK, ITK, TEC, TEC-2, JAK-1, JAK-2, LET23, c-fms, S6 kinases (including p70$^{S6}$ and RSKs), TGF-β/activin receptor family kinases and Clk.

The amino acid sequence motifs determined by the method of the invention are useful for predicting whether a protein is a substrate for a particular protein kinase. The primary amino acid sequence of a known protein can be examined for the presence of the determined amino acid sequence motif If the same or a very similar motif is present in the protein, it can be predicted that the protein could be a substrate for that protein kinase.

The amino acid sequence motifs determined by the method of the invention are also useful for designing peptide substrates for protein kinases. Accordingly, the invention also provides substrates for protein kinases. These substrates are peptides (or proteins containing these peptides) having an amino acid sequence corresponding to the amino acid sequence motif of the phosphorylation site of the kinase determined by the method of the invention. Theoretically, a substrate for any protein kinase can be determined by the invention. The invention provides for a peptide substrate for a protein kinase comprising an amino acid sequence of the formula (SEQ ID NO:4):

wherein Xaa5 is Ser, Thr or Tyr, and Xaa1, Xaa2, Xaa3, Xaa4, Xaa6, Xaa7, Xaa8 and Xaa9 are determined by the method of the invention. Thus, the protein kinase is contacted with an oriented degenerate peptide library comprising non-phosphorylated peptides comprising a formula (SEQ ID NO: 3):

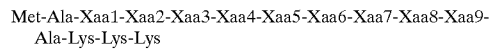

wherein Xaa1, Xaa2, Xaa3, Xaa4, Xaa6, Xaa7, Xaa8, and Xaa9 are any amino acid except an amino acid selected from the group consisting of Ser, Thr and Tyr and Xaa5 is selected from a group consisting of Ser, Thr and Tyr, under conditions which allow for phosphorylation of a substrate by the protein kinase. The protein kinase is allowed to phosphorylate peptides within the oriented degenerate peptide library having a phosphorylation site for the protein kinase to form a population of phosphorylated peptides. The population of phosphorylated peptides are separated from non-phosphorylated peptides by binding the population of phosphorylated peptides to a ferric column and the amino acid sequences of the population of phosphorylated peptides are determined. From the sequencing information, a relative abundance (RA) value for each amino acid residue at positions in the phosphorylated peptides corresponding to Xaa1, Xaa2, Xaa3, Xaa4, Xaa6, Xaa7, Xaa8, and Xaa9 is determined. The relative abundance value is determined by the formula:

$$RA = \frac{\text{amount of Xaa in the population of phosphorylated peptides}}{\text{amount of Xaa in the oriented degenerate peptide library}}$$

The amino acid sequences of Xaa1, Xaa2, Xaa3, Xaa4, Xaa6, Xaa7, Xaa8, and Xaa9 in the substrate for the protein kinase are determined by selecting amino acid residues that have a relative abundance value greater than 1.0 at positions in the phosphorylated peptides corresponding to Xaa1, Xaa2, Xaa3, Xaa4, Xaa6, Xaa7, Xaa8, and Xaa9. When the substrate is a substrate for a protein-serine/threonine kinase, Xaa5 is Ser or Thr, whereas when the substrate is a substrate for a protein-tyrosine kinase Xaa5 is Tyr.

The invention further provides substrates for protein kinase A, cell cycle control kinases, src family kinases, EGF receptor, pp92$^{c-fps/fes}$, lck, c-abl, PDGF receptor, FGF receptor, insulin receptor, casein kinase II, NIMA, phosphorylase kinase, Cam kinase II and Erk 1. These substrates are of the general formula (SEQ ID NO:5):

The length of a peptide which can be used as a substrate for a kinase is variable. For example, although the amino acid sequence motifs determined in this invention are 9 amino acids in length, a peptide which is shorter than 9 amino acids may be a substrate for a kinase. In certain cases, a peptide as short as 3 amino acids in length may be used as a substrate. Accordingly, Xaa1, Xaa1-Xaa2, Xaa1-Xaa2-Xaa3, Xaa9, Xaa8-Xaa9 and Xaa7-Xaa8-Xaa9 may or may not be present within the substrate. For example, the substrate may only be composed of Xaa2-Xaa3-Xaa4-Xaa5-Xaa6-Xaa7-Xaa8 or Xaa3-Xaa4-Xaa5-Xaa6-Xaa7 or Xaa4-Xaa5-Xaa6. If Xaa1, Xaa1-Xaa2 or Xaa1-Xaa2-Xaa3 are absent, then $Y_1$ is hydrogen or an amino-derivative group. Similarly, if Xaa9, Xaa8-Xaa9 or Xaa7-Xaa8-Xaa9 are absent, then $Y_2$ is hydrogen or a carboxy-derivative group.

Alternatively, the peptide substrate may be longer than 9 amino acids when Xaa1-Xaa2-Xaa3 and or Xaa7-Xaa8-Xaa9 are present. When Xaa1-Xaa2-Xaa3 are present, $Y_1$ can be hydrogen, an amino-derivative group or a peptide of the formula (Xaa)a, wherein a is an integer from 1–15 inclusive. Likewise, when Xaa7-Xaa8-Xaa9 are present, $Y_2$ can be hydrogen, a carboxy-derivative group or a peptide of the formula (Xaa)b, wherein b is an integer from 1–15 inclusive. When a and b are integers from 1–15, this encompasses peptides up to a length of 39 amino acids. Alternatively, a and b can be integers from 1–10 inclusive. This encompasses peptides up to a length of 29 amino acids. Alternatively, a and b can be integers from 1–5 inclusive. This encompasses peptides up to a length of 19 amino acids.

The sequences of Xaa1, Xaa2, Xaa3, Xaa4, Xaa6, Xaa7, Xaa8 and Xaa9 within the substrates of the invention are chosen from the amino acid sequence motif for the particular kinase.

Amino-derivative groups which can be present at the N-terminus of a peptide substrate (i.e., can be $Y_1$) include epoxysuccinyl, cholesteryl, aryl, aralkyl and acyl derivative. Carboxy-derivative groups which can be present at the C-terminus of a peptide substrate (i.e., can be $Y_2$) include alcohol, aldehyde, epoxysuccinate, acid halide, carbonyl, halomethane, and diazomethane derivatives.

Amino acid sequence motifs for protein kinase A, cell cycle control kinases (including cyclin B/p33$^{cdc2}$ and cyclin A/p33$^{CDK2}$), src family kinases (including pp60$^{c-src}$ and pp60$^{v-src}$), EGF receptor, pp92$^{c-fes/fps}$, lck, c-abl, PDGF receptor, FGF receptor, insulin receptor, casein kinase II, NIMA, phosphorylase kinase, Cam kinase II and Erk1 are provided by the invention. These motifs are described in detail in Examples 5–9 and 11–12.

Peptides composed of amino acid residues corresponding to one of the possible residues prescribed by the amino acid sequence motif of a kinase can be synthesized to create a peptide substrate for the kinase. Peptides composed of the most preferred amino acid residues of the motif (i.e, amino acid residues having the highest relative abundance at each degenerate position) can be synthesized as optimal peptide substrates for the kinase. The affinity of a peptide substrate for a kinase can be measured by standard techniques and the maximal rate of the kinase reaction (Vmax) and the concentration of peptide substrate at which the rate of the reaction is half maximal (Km) can be determined. For example, assays such as those described in Example 10 can be performed. As demonstrated in Example 10, optimal peptide substrates for cyclin B/p33$^{cdc2}$, cyclin A/p33$^{CDK2}$ and pp60$^{v-src}$, synthesized based upon the amino acid sequence motifs of the invention, have the highest affinities yet reported for these kinases.

It should be appreciated that it may be possible to make amino acid substitutions in a substrate peptide of the invention without substantially changing the affinity of the peptide for a kinase. For example, amino acid substitutions are likely to be possible at a position within the peptide which is relatively insensitive to variations in amino acid residues at that position. Similarly, amino acid substitutions are likely to be possible at a position which can broadly accommodate particular types of amino acids (e.g., hydrophobic or hydrophilic amino acids). The oriented degenerate peptide library used to determine an amino acid sequence motif of the invention represents peptides having every possible amino acid substitution at each degenerate position and the sequences determined from the library screening provide information regarding the effect of substituting a particular amino acid at each degenerate position surrounding a phosphorylation site. Thus, positions at which substitutions from the defined motif may be possible are readily identifiable from the data obtained from the sequenced phosphorylated peptides from the library (i.e, from the relative abundance values for each amino acid residue at each degenerate position). For example, a position which is relatively insensitive to variations in amino acid residues will have many amino acid residues at that position with relative abundance values around 1.0 (i.e, neither substantially selected for or against in the library screening). While one or more amino acid residues at that position may have an RA greater than 1.0 (the value set for inclusion in an amino acid sequence motif of the invention), it may be possible to substitute this residue with an amino acid residue having an RA of 1.0 or slightly less than one at that position without substantially affecting the affinity of the peptide substrate for the kinase. For example, for src family kinases, the position at −4 relative to the phosphorylated amino acid (at position 0) can displays many amino acids with relative abundance values around 1.0 (see FIG. 3, box A), indicating that this position can accommodate many different amino acids. Likewise, a position which can broadly accommodate, for example, a hydrophobic residue, will have many hydrophobic residues at that position with RA values around 1.0, although only one or a few residues may have the preferred RA value of greater than 1.0.

Accordingly, the invention encompasses a peptide substrate for a protein kinase having substantially equal affinity for the kinase as a peptide substrate comprising an amino acid sequence motif presented herein. The term "substantially equal affinity" is intended to mean that the peptide has an affinity for the kinase such that it can function in substantially the same way as a peptide having an amino acid sequence motif presented herein (e.g., the peptide can competitively inhibit the activity of a kinase against another substrate approximately equivalently to a peptide having an amino acid sequence motif presented herein). The affinity of a peptide for a kinase can be determined by standard techniques (such as described in Example 10) and can be quantitatively expressed as a Km value (i.e., the concentration of peptide at which the rate of the kinase reaction is half maximal). Preferably, a peptide having substantially equal affinity for a kinase as a peptide substrate comprising an amino acid sequence motif presented herein has a Km value no more than 2-fold greater than the Km of the peptide having the amino acid sequence motif. Alternatively, an affinity of a peptide for a kinase can be defined as a $K_I$ value (i.e., the concentration of peptide needed to inhibit kinase activity toward another substrate by 50%) by competition with other substrates. Preferably, a peptide having substantially equal affinity for a kinase as a peptide substrate comprising an amino acid sequence motif presented herein has a $K_I$ value no more than 2-fold greater than the $K_I$ of the peptide having the amino acid sequence motif. Km and $K_I$ values for some peptide substrates having an amino acid sequence motif of the invention are presented in Example 10.

The substrates of the invention can be contained within a larger protein by modifying a protein to contain the amino acid sequence of the phosphorylation site motif for a kinase. For example, a nucleotide sequence encoding a peptide corresponding in sequence to one of the possible amino acid sequences of the amino acid sequence motif can be deduced from the genetic code. (Because of the degeneracy of the genetic code, more than one nucleotide sequence may encode for the same peptide). A nucleic acid having this nucleotide sequence can be inserted into the coding sequence of a known protein by standard recombinant DNA technology. Alternatively, standard site-directed mutagenesis can be used to modify a protein to contain an amino acid sequence corresponding to a phosphorylation site for a kinase. Nucleotides within the coding region of a protein are mutated to nucleotides encoding a substrate of the invention. Alternatively, a fusion protein can be constructed, composed of a protein fused to a substrate of the invention, by standard recombinant DNA technology. Accordingly, the invention provides proteins modified to contain the substrates of the invention. Because such a modified protein contains a phosphorylation site for a particular protein kinase, the protein can serve as substrates for that protein kinase. For example, a protein may be modified to contain a phosphorylation site for a protein kinase in order to modulate a signal transduction pathway or to correct a defect in a mutant protein which normally is phosphorylated by the kinase but in which the mutation disrupts this phosphorylation.

The invention also provides pseudosubstrates for PKA, cell cycle control kinases (including cyclin B/p33$^{cdc2}$ and cyclin A/p33$^{CDK2}$), src family kinases (including pp60$^{c\text{-}src}$ and pp60$^{v\text{-}src}$), EGF receptor, p92$^{c\text{-}fps/fes}$, lck, c-abl, PDGF receptor, FGF receptor, insulin receptor, casein kinase II, NIMA, phosphorylase kinase, Cam kinase II and Erk1. The amino acid sequences of these pseudosubstrates are based upon the amino acid sequence motif for the phosphorylation sites of these kinases. In the pseudosubstrates, the amino acid residue which is normally phosphorylated by the kinase is changed to a non-phosphorylatable amino acid residue. For serine/threonine kinase substrates, the preferred pseudosubstrate peptides contain alanine at the position which is normally serine or threonine in the substrate peptide. The structure of the side chain of alanine is identical to that of serine except that serine has a phosphorylatable hydroxy group where alanine has hydrogen. Thus, this change in the substrate peptide to create a pseudosubstrate peptide does not dramatically alter the chemical structure of the peptide (which could disrupt its ability to bind to the catalytic site of the kinase) but destroys its ability to be phosphorylated by the kinase. A native inhibitor of protein kinase A is known to contain alanine (rather than serine or threonine) within a consensus motif for the PKA phosphorylation site (see Cheng, H-C., (1985) Biochem. J. 231:655–661 and Table 2 in Example 5). For the same reasons, the preferred pseudosubstrate peptides for protein-tyrosine kinases contain phenylalanine at the position normally occupied by tyrosine. The side chain of phenylalanine is identical to tyrosine except that tyrosine has a phosphorylatable hydroxy group where phenylalanine has hydrogen. Alternatively, for serine/threonine kinases, the phosphorylatable serine or threonine can be substituted with asparagine or glycine to mimic the serine or threonine residue, and for tyrosine kinases, the phosphorylatable tyrosine can be substituted with histidine to mimic the tyrosine residue.

It is possible that other amino acids can be substituted for the phosphorylatable residue in the peptide substrate (i.e., the serine/threonine or tyrosine residue) to create a pseudosubstrate. The requirements are that the substituted residue is not phosphorylatable by the particular kinase against which the pseudosubstrate is directed and that the pseudosubstrate can still bind to the catalytic site of the kinase. This can be determined by examining the ability of the pseudosubstrate to competitively inhibit the activity of the kinase. Standard techniques for assessing this are known in the art. For example, a kinase can be incubated with a native substrate or peptide substrate and [$\gamma$-$^{32}$P]-ATP in the presence or absence of the pseudosubstrate under conditions which normally allow phosphorylation of the substrate by the kinase. Phosphorylation of the native or peptide substrate is measured by determining the transfer of radiolabeled phosphate to the substrate (i.e, by detecting radiolabeled substrate) in the presence and absence of the pseudosubstrate. A pseudosubstrate which binds to the catalytic site of a protein kinase will block the catalytic site of the kinase and inhibit transfer of radiolabeled phosphate to the substrate. An example of a competitive inhibition assay which can be used to evaluate pseudosubstrates is described in detail in Example 10. Known substrates for particular kinases can be used as substrates in this type of assay. For example, acid-denatured enolase can be used as a substrate for pp60$^{v\text{-}src}$ (Kaplan, D., et al. (1986) Proc. Natl. Acad. Sci. USA 83:3624–3628) or histone H1 can be used as a substrate for p33$^{cdc2}$ (Atherton-Fessler, S., et al. (1993) Mol. Cell. Biol. 13:1675–1685).

A pseudosubstrate can be used to inhibit the activity of a kinase. It may be desirable to inhibit the activity of a kinase to modulate a signal transduction pathway. For example, certain oncogenic and/or viral forms of protein kinases have lost the ability to be down regulated and are therefore in a continually activated state. A pseudosubstrate could be used to downmodulate the activity of the kinase by blocking the catalytic site of the kinase, thereby preventing the kinase from phosphorylating native substrates.

The amino acid sequence motifs provided by the invention can also be used to design peptide analogs of the substrates of the invention. It has generally been found that when peptides are added to intact cells or administered in vivo their uptake is inefficient and/or they are degraded. Thus, in situations in which one wants to modulate a signal transduction pathway (for example, for therapeutic purposes in vivo) it is desirable to use a peptide analog rather than a peptide. The term "peptide analog" as used herein is intended to include molecules which mimic the chemical structure of a peptide and retain biological properties of the peptide but which are cell membrane permeable. The term "peptide analog" is also intended to include molecules which mimic the chemical structure of a peptide and retain biological properties of the peptide but which are more stable (e.g., are less susceptible to degradation either in the circulation in vivo or intracellularly) than the peptide. In the case of peptide analogs of the peptide substrates of the invention, the peptide analog retains the biological property of being able to bind to the protein kinase (i.e., occupy the catalytic site of the protein kinase). Preferably, the peptide analog is not phosphorylated by the protein kinase (i.e., the peptide analog is an analog of a pseudosubstrate), although a phosphorylatable peptide analog may also be useful. Approaches to designing peptide analogs are known in the art. For example, see Farmer, P. S. in Drug Design (E. J. Ariens, ed.) Academic Press, New York, 1980, vol. 10, pp. 119–143; Ball. J. B. and Alewood, P. F. (1990) J. Mol. Recognition 3:55; Morgan, B. A. and Gainor, J. A. (1989) Ann. Rep. Med. Chem. 24:243; and Freidinger, R. M. (1989) Trends Pharmacol. Sci. 10:270.

One approach to designing a peptide analog of the peptide substrates of the invention is to modify a protein kinase inhibitor to contain amino acid residues of the amino acid sequence motif for a particular kinase. For example, a number of small non-peptidic compounds have been shown to be competitive inhibitors of protein tyrosine kinases. For a review see Burke (1992) *Drugs Fut.* 17:119–131. Some of these compounds are competitive with respect to the ATP binding site on the kinase, whereas others are competitive with respect to the phosphoacceptor site (i.e., the substrate binding site) on the kinase. Compounds which are competitive with respect to the substrate are thought to mimic the tyrosyl-containing substrate (Levitzki (1990) *Biochem. Pharmacol.* 40:913–918; Shiraishi et al. (1989) *Cancer Res.* 49:2374–2378; and Imoto et al. (1987) *J. Antibiot.* 40:1471–1473). While some of these compounds display specificity for tyrosine kinases over serine/threonine kinases (Shiraishi et al. WO 88/07035 and Shiraishi et al. (1988) *Chem. Pharm. Bull.* 36:974–981) and some degree of selectivity among protein tyrosine kinases (Yaish et al. (1988) *Science* 242:933–935; Gazit et al. (1989) *J. Med. Chem.* 32:2344–2352; Gazit et al. (1991) *J. Med. Chem.* 34:1896–1907; Levitzki and Gilon (1991) *Trends Pharmacol. Sci.* 12:171–174; Levitzki (1990) *Biochem. Pharmacol.* 40:913–918; Shiraishi et al. (1989) *Cancer Res.* 49:2374–2378), they are not highly specific for particular protein tyrosine kinases. The specificity of compounds which are competitive with the substrate binding site on tyrosine kinases may be increased by adding to these compounds amino acids found within a preferred phosphorylation site for a particular kinase (i.e., amino acids surrounding the phosphorylation site).

For example, a class of styryl-containing compounds have been described which are competitive inhibitors of the substrate binding site of protein tyrosine kinases (see for example CA 109:210674t; CA 106:201757h; CA 106:201758j; CA 106:201762f; CA 106:201763g; CA 107:96584v; CA 107:58668t; CA 106:213937e; CA 106:213918z; CA 110:212392u; WO 88/07035; and Shiraishi et al. (1987) *Biochem. Biophys. Res. Commun.* 147:322–328). These styryl-containing compounds include erbstatin (Nakamura et al. (1986) *J. Antibiot.* 39:314–315; and Isshiki et al. (1987) *J. Antibiot.* 40:1209–1210), piceatannol (Geahlen and McLaughlin (1989) *Biochem. Biophys. Res. Commun.* 165:241–245) and tyrphostins (EP 0 322 738 A2; Yaish et al. (1988) *Science* 242:933–935; Gazit et al. (1989) *J. Med. Chem.* 32:2344–2352; Gazit et al. (1991) *J. Med. Chem.* 34:1896–1907; Levitzki and Gilon (1991) *Trends Pharmacol. Sci.* 12:171–174; Levitzki (1990) *Biochem. Pharmacol.* 40:913–918). Amino acid residues located N-terminal and C-terminal to the phosphorylated tyrosine within an amino acid sequence motif of a kinase (e.g., at the −1 and +1 positions relative to a phosphorylated tyrosine at position 0) could be added to these compounds to increase the specificity of the compound for a particular kinase.

Another type of peptide analog of the peptide substrates of the invention which can be made is a peptide which has methylated amide linkages. This modification of the peptide has been found to increase the membrane permeability of the peptide and increase its stability. Additionally, the rigidity of the peptide may be increased, which may increase the affinity of the peptide analog for the catalytic site of the kinase relative to the unmodified peptide substrate.

The peptide substrates of the invention are useful for detecting and quantitating the activity of protein kinases in vitro. For example, a solution can be contacted with a substrate of the invention to detect the presence of a particular kinase in the solution. For example, the solution can be a cell extract or a column fraction of a partially purified kinase. The peptides substrates can also be used to determine the effect of various agents (e.g, a pharmaceutical compound) on the activity of a kinase by examining what effect the agent has on the phosphorylation of the peptide substrate by the kinase. For in vitro assays, the peptide substrate can be immobilized on a solid support (e.g., a bead) to allow for easy separation of the peptide from other reaction components (e.g., [$\gamma$-$^{32}$P]-ATP). With regard to these in vitro uses pertaining to monitoring the presence and activity of kinases, it should be noted that the affinity of certain peptide substrates of the invention for particular kinases is higher than has been previously observed for any native or synthetic peptide substrate, including commercially available peptide substrates marketed for these uses (see Example 10).

The peptide substrates of the invention are also useful for raising antibodies against these peptides. Such antibodies would be specific for preferred phosphorylation sites of a protein kinases. These antibodies could then be used to identify native substrates for the protein kinase, for example by using the antibodies to immunoprecipitate proteins from cell extracts. Proteins immunoprecipitated by the antibodies would contain a preferred phosphorylation site for the kinase and therefore would be candidates for substrates of the kinase. (The ability of a protein so identified to serve as substrate for the kinase could then be tested in vitro by standard techniques). Considering that a limiting factor in identifying native substrates for certain protein kinase is their low abundance in cells, antibodies directed against preferred phosphorylation sites for a kinase may offer a means by which to purify low abundance substrates.

The peptide substrates of the invention can also be used to competitively inhibit the activity of a protein kinase. Because of their high affinity for a protein kinase (i.e., higher than the previously reported affinities of other substrates for the kinase), these peptides are likely to be very efficient competitive inhibitors. The ability of a peptide substrate of the invention to competitively inhibit the activity of a kinase is demonstrated in Example 10. The pseudosubstrates and peptide analogs of the invention can also be used to inhibit the activity of a kinase since these compounds retain the ability to bind to the catalytic site of the kinase. The invention provides a method for inhibiting phosphorylation of a native substrate by a kinase by contacting the kinase with an inhibitory amount of a peptide substrate of the invention to competitively inhibit phosphorylation of the native substrate by the kinase. Alternatively, the kinase can be contacted with an inhibitory amount of a pseudosubstrate or peptide analog of the invention.

Protein kinases play a role in virtually all signal transduction pathways, including those involved in cell cycle control, immunological responses, transcriptional activation and cell development. Moreover, protein kinases play a role in cell transformation. The ability to inhibit the activity of protein kinases thus provides a means by which to modulate a wide variety of cellular responses. Novel therapeutic agents composed of or based upon the peptide substrates, pseudosubstrates and peptide analogs of the invention may thus have applications in a wide variety of disease situations.

This invention is further illustrated by the following examples which should not be construed as limiting. The contents of all references and published patents and patent applications cited throughout the application are hereby incorporated by reference.

EXAMPLE 1

Construction of an Oriented Degenerate Peptide Library

A soluble synthetic peptide library was synthesized by N$^\alpha$-Fmoc-based synthesis conducted on a Milligen/

Biosearch 9600 synthesizer using standard (benzotriazolyloxy)tris-(dimethylamino)-phosphonium hexafluorophosophate (BOP)/1-hydroxybenzotriazole coupling protocols and protected amino acids. For degenerate positions, the resin was deprotected with 30% piperidine as usual and washed extensively with dimethylformamide. The solvent was removed and the moist resin is divided into 18 equivalent amounts by weight. Each aliquot was coupled for 18 hours with 4 equivalents each of BOP, 1-hydroxybenzotriazole, and a different $N^\alpha$-Fmoc-amino acid having the appropriate side chain protecting group. All aliquots were recombined and the procedure was repeated at each degenerate position. Peptide cleavage and side chain deprotections were with trimethylsilyl bromide as described (Domchek, S, et al. (1993) *Biochem.* 31:9865–9870). The peptide mixture was precipitated with diethyl ether (4° C.) and desalted on a column of Bio-Gel P2.

The following peptide library was constructed (SEQ ID NO:3):

Met-Ala-Xaa-Xaa-Xaa-Xaa-Ser-Xaa-Xaa-Xaa-Xaa-Ala-Lys-Lys-Lys where Xaa indicates all amino acids except Trp, Cys, Tyr, Ser, or Thr. A similar oriented degenerate peptide library was synthesized with Tyr at position 7. The Trp and Cys were omitted to eliminate problems with sequence detection and oxidation and Tyr, Ser and Thr were omitted from the degenerate positions to insure that the only potential site of phosphorylation is the residue at position 7. The total theoretical degeneracy of this library is $15^8=2,562,890,625$. The 4 degenerate residues N-terminal and C-terminal of the site of phosphorylation cover the region most likely to be involved in catalytic site recognition on the basis of the motifs that have been determined for protein kinases to date. The Met-Ala at the N-terminus provides two amino acids to verify that peptides from this mixture are being sequenced and a quantification of the peptides present. Similarly, the Ala at residue 12 provides a second quantification and an estimate of how much loss of peptide has occurred during sequencing. The poly-Lys tail prevents wash-out during sequencing and improves the solubility of the mixture (no solubility problems have occurred at neutral pH and 3 mg/ml). The peptide mixture was sequenced to insure that all 15 amino acids were present at similar amounts at all 8 degenerate positions.

EXAMPLE 2

Phosphorylation of a Peptide Library by a Protein Kinase

The degenerate peptide library constructed as described in Example 1, with either serine or tyrosine at the 7th position, was used as a substrate for several different protein kinases. Protein kinase A (bovine) was obtained commercially (Sigma). GST-cyclin B/p33$^{cdc2}$ (Atherton-Fessler et al. (1993) *Mol. Cell. Biol.* 13:1675–1685), GST-cyclinA/p33$^{CDK2}$ (Atherton-Fessler et al. (1993) *Mol. Cell. Biol.* 13:1675–1685), human EGF receptor, chicken pp60$^{v\text{-}src}$, polyoma virus middle T antigen/pp60$^{c\text{-}src}$ (Piwnica-Worms et al. (1990) *J. Virol.* 64:61–68) and pp92$^{c\text{-}fps/fes}$ were expressed by baculoviruses. The baculovirus-expressed protein kinases were immobilized on protein A beads using precipitating antibodies or on glutathione-agarose bead for kinases obtained as GST fusion proteins to minimize the problem of separating the peptides from the enzyme or impurities in the enzyme. A monoclonal antibody against pp60$^{v\text{-}src}$ (Ab-1) was commercially obtained (Oncogene Science). The EGF receptor monoclonal antibody (13A9) was previously described. The fps/fes-specific regressing-tumor antiserum was previously described (Feldman et. al, (1987) *Oncogene Res.* 1:441–458). In the case of PKA, the reaction was done in solution and the peptides were separated from the kinase through a spin column (Centricon 10).

In a typical reaction, the protein kinase was added to 300 μl of solution containing 1 mg of degenerate peptide mixture, 100 μM ATP with a trace of [γ-$^{32}$P]-ATP (roughly 6×10$^5$ cpm), 1 mM DTT, 10 mM MgCl$_2$ or MnCl$_2$ and buffered to pH 7.0 with Tris. The concentration of peptides in the reaction was approximately 1.8 mM. The reaction mixture was incubated at 25°. It is preferable that at least 0.5% to 1% of the peptides in the library are phosphorylated during the kinase reaction (for reasons discussed in Example 4) and reaction times were chosen accordingly to achieve this result. Incubation times in the range of 2½ hours were used.

EXAMPLE 3

Separation of Phosphorylated Peptides from Non-Phosphorylated Peptides and Peptide Sequencing After a kinase reaction was performed as described in Example 2, the peptide supernatant was removed and diluted with 300 μl of 30% acetic acid. This mixture was then added to a 1 ml DEAE column previously equilibrated with 30% acetic acid and the column was eluted with 30% acetic acid (Kemp et al, (1976) *Proc. Natl. Acad. Sci. USA* 73: 1038–1042). In initial experiments, the fractions from the column were analyzed for peptide, phosphopeptide, [γ-$^{32}$P]-ATP, and $^{32}$PO$_4$ by phosphocellulose paper (P81), TLC or SDS PAGE. It was determined that after the 600 μl void volume, the next 1 ml contained both phosphorylated and non-phosphorylated peptides but was free of [γ-$^{32}$P]-ATP. This fraction was collected and lyophilized. Since the peptide fraction was free of [γ-$^{32}$P]-ATP, the radioactivity in this fraction provided an initial estimate of the fraction of the total peptide mixture that was phosphorylated.

A ferric chelation column (IDA beads, Pierce) was used for separation of phosphopeptides. This column has been used in the past to separate tryptic phosphopeptides of phosphorylated proteins from the bulk of non-phosphorylated tryptic peptides (Muszynska et al., (1986) *Biochem.* 25: 6850–6853; Muszynska et al., (1992) *J. Chromatography* 604:19–28). However, we discovered that in order to accomplish a quantitative removal of the non-phosphorylated peptides from the phosphopeptides in the mixture without loss of a subfraction of phosphopeptides, it was necessary to change the loading and elution conditions from published procedures. A 1 ml column of IDA beads (Pierce) was charged with 5 ml of 20 mM ferric chloride at 1 ml/2 min, washed with 8 ml of water at 1 ml/min, washed with 6 ml of 500 mM NH$_4$CO$_3$ pH 8.0 at 1 ml/min, washed again with 6 ml of water and then equilibrated with 6 ml of buffer A (50 mM MES, 1 M NaCl, pH 5.5). The dried sample of peptide/phosphopeptide mixture was dissolved in 200 μl of buffer A and loaded onto the ferric column. The column was then eluted with 5 ml of buffer A followed by 5 ml of buffer B (2 mM MES, pH 6.0). The phosphopeptides were then eluted with 4 ml of 500 mM NH$_4$CO$_3$, pH 8.0. Finally, the Fe$^{3+}$ was eluted with 100 mM EDTA pH 8.0. All elutions were at 0.5 ml/min. and 0.5 ml fractions were collected. The amount of peptide at each fraction was estimated by absorbency at UV 280 nm (fractions 1–10) and the amount of the phosphorylated peptides present was estimated by the incorporated radioactivity. Less than 0.1% of the total non-phosphorylated peptides eluted at fraction 11–14 as judged by the presence of a non-phosphorylated residue at cycle 7 in the sequence of this mixture. Greater than 90% of the radioactivity applied eluted in fractions 11–14. A graph depicting the elution profile of peptides from the ferric column is shown in FIG. 1.

The phosphopeptides eluted from the column were dried down to a small volume and sequenced using an Applied Biosystems 477A Protein Sequencer.

EXAMPLE 4

Analysis of Amino Acid Sequence Data

In a reaction in which 1% of the peptide mixture is phosphorylated, the total quantity of phosphopeptides is (1.8 mM)×(0.3 ml)×(0.01)=5.4 nmoles. Typically, about 1–2 nmoles of phosphopeptide mixture is added to the automated sequencer. This means that in a cycle in which all 15 residues are equally abundant, the yield of each amino acid is (1 nmol)×(1/15)=60 pmoles. The abundance of each amino acid at a given cycle in the sequence of the phosphopeptide mixture was divided by the abundance of the same amino acid at the same cycle of the starting mixture to determine the relative abundance of each amino acid residue at a given cycle (i.e, corresponding to a given degenerate position in the peptide). In this way, variations in the abundance of amino acids at particular residue (i.e. position 3, the first degenerate residue) in the starting mixture or variations in yield of amino acids in the sequencer are divided out. If the kinase is insensitive to amino acid variations at a degenerate position, then the relative abundance of each amino acid at this cycle in the phosphopeptide mixture will be the same as in the starting mixture (i.e., the relative abundance of each amino acid will be 1.0). If an amino acid residue is preferred at this particular position, it will have a relative abundance greater than 1.0 whereas if the amino acid residue is selected against at this position it will have a relative abundance less than 1.0. The data can be plotted in the form of a bar graph (see FIGS. 2 and 3) to visually depict the relative abundance of each amino acid residue.

In analyzing the sequencing data, two complexities must be considered. The first problem is that contamination from non-phosphorylated peptides that may elute from the ferric column together with the phosphorylated peptides will complicate the results. This problem has been assessed in two ways. First, a mock reaction in which the same procedure is followed but the protein kinase is omitted was performed. The fractions from the ferric column that normally contain the phosphopeptides (i.e., 11–14) are pooled, lyophilized and sequenced. The yield of total peptides (judged by quantity of Ala at cycle 2) in this pool is an indication of how much contaminating non-phosphorylated peptides are present in the kinase experiment. Typically, the yield in this mock experiment is about 0.1% of the total starting peptide mixture. Upon sequencing, the column fractions containing the contaminating non-phosphorylated peptide were found to be enriched in Asp and Glu at every degenerate cycle, presumably due to interaction of these residues with the Fe3+. Because of this 0.1% of contaminating non-phosphorylated peptides, it is necessary to phosphorylate at least 0.2% of the peptide mixture in order for the phosphopeptides to be more abundant than the non-phosphorylated peptides in the mixture pooled. Preferably, at least 0.5% to 1% of the peptide mixture is phosphorylated.

The second procedure used to estimate non-phosphorylated peptides in the phosphopeptide mixture is to note the quantity of non-phosphorylated Ser at cycle 7 and compare it to the quantity of Ala at cycle 2. In the starting mixture the ratio of Ser at cycle 7 to Ala at cycle 2 is one. The actual measured ratio in the microsequencer is less than one because of the fall-off in yield with each cycle and the low recovery of Ser. However, the measured ratio for the starting material is reproducible. Since the phosphorylated peptides should have no non-phosphorylated Ser at cycle 7, the ratio of Ser at cycle 7 to Ala at cycle 2 ought to be zero. Any value above zero can be assumed to be due to contamination with non-phosphorylated peptide and using the ratio calculated for the starting material, one can estimate the amount of contamination. In most experiments, this calculation was in good agreement with the contamination estimated from the mock experiment. In those experiments where only approximately 0.2% of the mixture was phosphorylated as judged by radioactivity, the ratio of Ser at cycle 7 to Ala at cycle 2 in the phosphopeptide mixture was relatively high (about 30% of the ratio in the starting material) indicating significant contamination. When higher yields were obtained, the ratio was lower.

In some experiments where only about 0.5% of the total mixture was phosphorylated, a correction was made for the 0.1% contaminating nonphosphorylated peptides. A control mock reaction, as described above was performed and the amino acid abundance at each cycle from this control experiment was subtracted from the kinase experiment to correct for the background. To calculate the relative abundance of amino acids at each degenerate position, the corrected data were then compared to the starting mixture to create the ratios of abundance of amino acids. The sum of the abundance of each amino acid at a given cycle was normalized to 15 (the number of amino acids present) so that each amino acid would have a value of 1 in the absence of selectivity at a particular position.

Ultimately, confidence in this procedure is provided by the reproducibility of the results obtained with a given kinase and by differences observed when different kinases are used to phosphorylate the same peptide library.

EXAMPLE 5

Determination of an Amino Acid Sequence Motif for the Phosphorylation Site of Protein Kinase A Since the peptide substrate specificity of protein kinase A (PKA) has been extensively studied, the oriented degenerate peptide library was first tested with this enzyme. The peptide library described in Example 1 in which Ser was fixed a position 7 was used. The library was incubated with PKA (catalytic subunit, from Sigma) under conditions were approximately 1% of the total mixture was phosphorylated (as described in Example 2). The phosphopeptide products were then separated from the bulk of the non-phosphorylated peptides of the library using the ferric-IDA column and the mixture was sequenced (as described in Example 3).

By comparing the sequence of the phosphopeptide products to that of the complete (i.e., starting) library, it was possible to determine which residues N-terminal and C-terminal to the phosphorylated serine were preferred for substrate recognition by calculating relative abundance values for each amino acid residue at each degenerate position. The results are presented as bar graphs in FIG. 2. Box A represents the relative abundance of amino acid residues at position 3 in the mixture of phosphopeptides products. This is the first degenerate position of the library and is 4 residues N-terminal of the phosphorylation site (position 7). In general, Arg was preferred at each position N-terminal of the phosphorylated Ser (see boxes A, B, C and D) while hydrophobic residues were preferred at positions C-terminal of the Ser (see boxes E, F, G and H). The greatest selectivity was observed at residues −3 and −2 relative to the Ser (boxes B and C): more than 60% of the phosphopeptides have Arg at these positions. At the −3 position (relative to the Ser), His is the second best amino acid while at the −2 position (relative to the Ser), Lys is the second best. The least selectivity was observed at positions +2 and +3 relative to the Ser (boxes F and G).

The amino acid residues at degenerate positions having a relative abundance value greater than 1.0 are summarized below in Table 1 (the relative abundance value is in parentheses next to the amino acid residue and positions are indicated relative to the phosphorylation site at 0). More preferred amino acid residues within the motif have relative abundance values equal to or greater than 1.5 and are highlighted in bold-face type:

TABLE 1

Preferred amino acid residues at positions surrounding the phosphorylation site of protein kinase A (SEQ ID NO: 6)

| −4 | −3 | −2 | −1 | 0 | +1 | +2 | +3 | +4 |
|---|---|---|---|---|---|---|---|---|
| R (7.23) | R (9.97) | R (9.62) | R (7.09) | S | I (2.49) | I (1.81) | F (1.62) | I (3.74) |
| H (2.33) | H (1.87) | K (1.66) | H (1.62) | (T) | M (1.86) | V (1.74) | I (1.56) | L (1.43) |
| | | H (1.07) | | | F (1.85) | F (1.58) | M (1.55) | F (1.23) |
| | | | | | L (1.75) | | V (1.39) | M (1.22) |
| | | | | | V (1.70) | | L (1.30) | V (1.18) |

The preferred amino acid residues at positions surrounding the phosphorylation site of protein kinase A represent the amino acid sequence motif for the phosphorylation site as determined by the library screening. This amino acid sequence motif can be compared to known in vitro and in vivo peptide substrates and inhibitors for PKA. Such an analysis is shown below in Table 2:

TABLE 2

Comparison of the amino acid sequence motif determined by the peptide library to sequences at the same region of known substrates and inhibitors of PKA*

| Peptide/Protein | Sequence | | | | | | | | | |
|---|---|---|---|---|---|---|---|---|---|---|
| | −4 | −3 | −2 | −1 | 0 | +1 | +2 | +3 | +4 | |
| PKA substrate amino acid sequence motif (SEQ ID NO: 6) | R | R | R | R | S | I | I | F | I | |
| | H | H | K | H | T | M | V | I | L | |
| | | | H | | | F | F | M | F | |
| | | | | | | L | | V | M | |
| | | | | | | V | | L | V | |
| Walsh inhibitor sequence in pseudo-substrate domain: | G | R | R | N | A | I | H | D | I | (SEQ ID NO: 15) |
| Kemptide sequence | L | R | R | A | S | L | G | | | (SEQ ID NO: 16) |
| Optimal peptide substrate based on G R T fragment of Walsh inhibitor (40 fold lower K$_M$ than Kemptide) | G | R | R | N | S | I | | | | (SEQ ID NO: 17) |
| Phosphorylase kinase, a-subunit | F | R | R | L | S | I | S | T | E | (SEQ ID NO: 18) |
| Phosphorylase kinase, b-subunit | K | R | S | G | S | V | Y | E | P | (SEQ ID NO: 19) |
| Glycogen synthase, site 1a | P | R | R | A | S | C | T | S | S | (SEQ ID NO: 20) |
| Glycogen synthase, site 1b | K | R | S | N | S | V | D | T | S | (SEQ ID NO: 21) |
| Glycogen synthase, site 2 | S | R | T | L | S | V | S | S | L | (SEQ ID NO: 22) |
| Pyruvate kinase | L | R | R | A | S | L | A | Q | L | (SEQ ID NO: 23) |
| 6-Phosphofructo-2-kinase/fructose-2,6-bisphosphatase | R | R | R | G | S | S | I | P | Q | (SEQ ID NO: 24) |
| Protein phosphatase inhibitor I | R | R | R | P | T | P | A | T | L | (SEQ ID NO: 25) |
| pp60$^{src}$ | O | R | R | R | S | L | E | P | A | (SEQ ID NO: 26) |

*Substrate and inhibitor sequences are from Taylor et al., (1990) Ann. Rev. Biochem. 59:971–1005 and Walsh et al., (1990) Peptides and Protein Phosphorylation (B. E. Kemp, ed.) CRC Press Inc. pp. 43–84.

Two observations can be made from this analysis. First, the most optimal substrates predicted from the library is in good agreement with the sequences of known substrates and inhibitors for PKA, supporting the validity of this technique for determining the substrate specificity of a kinase. Second, differences do exist between the preferred amino acid sequences selected by peptide library screening and the amino acid sequences of known substrates and inhibitors. Amino acid residues in the substrates and inhibitors listed in Table 2 which differ from the determined amino acid sequence motif for PKA are indicated in bold type.

EXAMPLE 6

Determination of Amino Acid Sequence Motifs for Cell Cycle Control Kinases

The substrate specificities of two other protein-serine/threonine kinases were examined using the serine-containing oriented degenerate peptide library as described for PKA in Example 5. The two kinases examined, cyclin B/p33$^{cdc2}$ and cyclin A/p33$^{CDK2}$, are kinases involved in cell cycle control. The results are presented as bar graphs in FIG. 3 (for cyclin B/p33$^{cdc2}$) and FIG. 4 (for cyclin A/p33$^{CDK2}$).

The results of the library screening for these two kinases are summarized below in Tables 3 and 4, which present the amino acid residues at degenerate positions having a relative abundance value equal to or greater than 1.0. More preferred amino acid residues within the motif have relative abundance values equal to or greater than 1.5 and are highlighted in bold-face type:

TABLE 3

Preferred amino acid residues at positions surrounding the phosphorylation site of cyclin B/p34$^{cdc2}$ (SEQ ID NO: 8)

| −4 | −3 | −2 | −1 | 0 | +1 | +2 | +3 | +4 |
|---|---|---|---|---|---|---|---|---|
| R (2.72) | R (2.50) | P (2.16) | M (1.67) | S | P (11.07) | P (3.17) | K (2.55) | K (1.90) |
| H (1.31) | P (1.44) | M (1.5) | Q (1.39) | (T) | | K (1.68) | R (1.85) | I (1.86) |
| | M (1.40) | | A (1.26) | | | M (1.18) | P (1.38) | R (1.45) |
| | V (1.33) | | N (1.23) | | | A (1.07) | | |
| | I (1.32) | | R (1.18) | | | V (1.10) | | |
| | | | K (1.12) | | | | | |

TABLE 4

Preferred amino acid residues at positions surrounding the phosphorylation site of cyclin A/p34$^{CDK2}$ (SEQ ID NO: 9)

| −4 | −3 | −2 | −1 | 0 | +1 | +2 | +3 | +4 |
|---|---|---|---|---|---|---|---|---|
| R (2.89) | R (2.60) | P (1.89) | M (1.70) | S | P (11.50) | P (2.14) | K (1.88) | K (1.67) |
| H (1.66) | H (2.12) | M (1.54) | Q (1.5) | (T) | | M (1.58) | R (1.70) | N (1.30) |
| N (1.32) | V (1.18) | L (1.38) | R (1.32) | | | R (1.31) | | |
| Q (1.11) | P (1.13) | | N (1.32) | | | V (1.15) | | |
| | M (1.11) | | A (1.21) | | | K (1.11) | | |

Although these two kinases are associated with distinct cyclins and are turned on at different stages of the cell cycle, the peptide substrates that they preferred for phosphorylation were nearly identical. A composite amino acid sequence motif, combining the two motifs for the two cell cycle control kinases, can be created having the sequence (SEQ ID NO: 7):

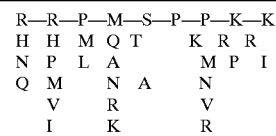

This composite amino acid sequence motif was compared to the amino acid sequences of known substrates for these cell cycle control kinases. This analysis is shown below in Table 5. Amino acid residues in known substrates of p33$^{cdc2}$ or p33$^{CDK2}$ which differ from those in the determined amino acid sequence motif are shown in bold type.

TABLE 5

Comparison of the amino acid sequence motif determined by the peptide library to sequences at the same region of known substrates of p33$^{cdc2}$ and p33$^{CDK2}$*

| Peptide/Protein | Sequence | | | | | | | | | |
|---|---|---|---|---|---|---|---|---|---|---|
| | -4 | -3 | -2 | -1 | 0 | +1 | +2 | +3 | +4 | |
| p33$^{cdc2}$ and p33$^{CDK2}$ motif | R | R | P | M | S | P | P | K | K | |
| SEQ ID NO: 7) | H | H | M | Q | | T | K | R | R | |
| | N | P | L | A | | | M | P | I | |
| | Q | M | | N | | | A | | N | |
| | | V | | R | | | V | | | |
| | | I | | K | | | R | | | |
| Known substrates | | | | | | | | | | |
| Xenopus histone H1 | V | A | A | K | S | P | A | K | A | (SEQ ID NO: 27) |
| | K | A | A | K | S | P | K | K | T | (SEQ ID NO: 28) |
| Chicken Lamin B2 | G | T | P | L | S | P | T | R | I | (SEQ ID NO: 29) |
| pp60$^{c-src}$ | D | T | H | R | T | P | S | R | S | (SEQ ID NO: 30) |
| SV40 LT Antigen | S | Q | H | S | T | P | P | K | K | (SEQ ID NO: 31) |
| Yeast SW15 | Y | T | T | N | S | P | S | K | I | (SEQ ID NO: 32) |
| | V | I | K | R | S | P | R | K | R | (SEQ ID NO: 33) |
| Predicted Sites | | | | | | | | | | |
| Protein Phosphatase (T316) | G | R | P | I | T | P | P | R | K | (SEQ ID NO: 34) |
| Strathmin | E | F | P | L | S | P | P | K | K | (SEQ ID NO: 35) |
| HIV Enhancer-Binding Protein 2 | R | R | P | V | S | P | G | K | D | (SEQ ID NO: 36) |
| S6 Kinase II Alpha (S335) | R | R | E | M | S | P | P | F | K | (SEQ ID NO: 37) |
| Elongation Factor 1-gamma (216) | D | K | P | L | S | P | P | Q | K | (SEQ ID NO: 38) |
| Histone H5 (S133) | R | K | A | R | S | P | A | K | K | (SEQ ID NO: 39) |
| Cell Division FTSZ protein (S548) | R | R | P | L | S | P | E | A | S | (SEQ ID NO: 40) |
| Ubiquitin-Conjugating Enzyme | D | Y | P | L | S | P | P | K | L | (SEQ ID NO: 41) |

*Substrate sequences are from Nigg, E. A. (1991) Seminars in Cell Biology 2:261–270.

EXAMPLE 7

Determination of Amino Acid Sequence Motifs for src Family Kinases

The version of the oriented degenerate peptide library with tyrosine at position 7 was used to evaluate the substrate specificities of two protein-tyrosine kinases which are members of the src family of protein-tyrosine kinases. The src family kinases pp60$^{v-src}$ and polyoma virus middle T/pp60$^{c-src}$ were examined and bar graphs summarizing the results of the library screening are shown in FIG. 5. The results of the library screening are also summarized below in Tables 6 and 7 and, which presents the amino acid residues at degenerate positions having a relative abundance value equal to or greater than 1.0. More preferred amino acid residues within the motif have relative abundance values equal to or greater than 1.5 and are highlighted in bold-face type:

TABLE 6

Preferred amino acid residues at positions surrounding the phosphorylation site of pp60$^{c-src}$ (SEQ ID NO: 11)

| -4 | -3 | -2 | -1 | 0 | +1 | +2 | +3 | +4 |
|---|---|---|---|---|---|---|---|---|
| D (1.45) | E (2.51) | E (1.96) | I (3.04) | Y | G (2.24) | E (1.66) | F (2.87) | F (1.53) |
| E (1.32) | D (1.88) | D (1.68) | V (2.38) | | E (2.06) | | I (1.52) | E (1.38) |
| | | G (1.5) | L (1.52) | | | | L (1.43) | |
| | | | P (1.17) | | | | M (1.02) | |

TABLE 7

Preferred amino acid residues at positions surrounding the phosphorylation site of pp60$^{v-src}$ (SEQ ID NO: 12)

| -4 | -3 | -2 | -1 | 0 | +1 | +2 | +3 | +4 |
|---|---|---|---|---|---|---|---|---|
| E (1.66) | E (3.18) | E (2.24) | I (4.16) | Y | G (2.63) | E (2.51) | F (4.00) | D (2.20) |
| D (1.5) | D (2.23) | D (1.98) | V (3.14) | | E (2.52) | D (1.40) | I (1.81) | E (2.10) |
| | | G (1.62) | L (1.63) | | D (1.58) | | L (1.70) | |
| | | N (1.43) | P (1.08) | | | | V (1.60) | |
| | | | | | | | M (1.17) | |

The peptide substrates that are preferred for phosphorylation by these two members of the src family of tyrosine kinases were nearly identical. A composite amino acid sequence motif, combining the two motifs for the src family kinases, can be created having the sequence (SEQ ID NO: 10):

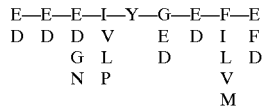

The sequences preferred by pp60$^{c\text{-}src}$ and pp60$^{v\text{-}src}$ suggest that the catalytic site and SH2 domain provide double selection for downstream signaling. The selection for Glu at positions −3 and −2 N-terminal of the phosphorylation site is in agreement with previous studies (Hunter et al. *J. Biol. Chem.* 257:4843; Patchinsky et al. *Proc. Natl. Acad. Sci.* 79:973; and Cooper et al. *J. Biol. Chem.* 259:7835). The surprising result is that Ile or Val at the −1 position is even more important than Glu at −2 or −3 in determining selectivity. An even more interesting surprise is that the preferred sequence C-terminal of the phosphotyrosine (PhosphoTyr-Gly/Glu-Glu-Phe/Ile; (SEQ ID NO: 42)) is very similar to the optimal sequence for binding to the SH2 domain of src family members (PhosphoTyr-Glu-Glu-Ile;(SEQ ID NO: 43); Songyang, Z., et al (1993) Cell 72:767–778). Thus, the active site of pp60/$^{v\text{-}src}$ prefers to phosphorylate substrates that its own SH2 domain can bind.

This composite amino acid sequence motif was compared to the amino acid sequences of known substrates for these tyrosine kinases. This analysis is shown below in Table 8. Amino acid residues in known substrates of pp60$^{c\text{-}src}$ or pp60$^{v\text{-}src}$ which differ from those in the determined amino acid sequence motif are shown in bold type.

TABLE 8

Comparison of the amino acid sequence motif determined by the peptide library to sequences at the same region of known substrates of pp60$^{c\text{-}src}$ and pp60$^{v\text{-}src}$*

| Peptide/Protein | Sequence | | | | | | | | | |
|---|---|---|---|---|---|---|---|---|---|---|
| | −4 | −3 | −2 | −1 | 0 | +1 | +2 | +3 | +4 | |
| pp60$^{c\text{-}src}$ and pp60$^{v\text{-}src}$ motif (SEQ ID NO: 10) | | E | E | I | Y | G | E | F | E | |
| | | D | D | V | | E | D | I | F | |
| | | | G | L | | D | | L | D | |
| | | | N | P | | | | V | | |
| | | | | | | | | M | | |
| some good in vitro substrates | | | | | | | | | | |
| Gastrin | | E | E | A | Y | G | W | M | D | (SEQ ID NO: 44) |
| Enolase (Y43) | | T | G | I | Y | E | A | L | E | (SEQ ID NO: 45) |
| p34$^{cdc2}$ peptide (Y15) | | E | G | T | Y | G | V | V | Y | (SEQ ID NO: 46) |
| in vivo substrates | | | | | | | | | | |
| Mouse Polyoma middle t (Y315) | | E | E | E | Y | M | P | M | E | (SEQ ID NO: 47) |
| Hamster Polyoma middle t (Y295) | | E | N | E | Y | M | P | M | A | (SEQ ID NO: 48) |
| Hamster Polyoma middle t (Y321) | | E | P | Q | Y | E | E | I | P | (SEQ ID NO: 49) |
| PtdIns 3-kinase p85 subunit (Y607) | | E | D | Q | Y | S | L | V | E | (SEQ ID NO: 50) |
| pp60v-src (Y416) Autophosphorylatio | | D | N | E | Y | T | A | R | Q | (SEQ ID NO: 51) |
| pp60v-src (Y92) Autophosphorylation | | L | Y | D | Y | E | S | W | I | (SEQ ID NO: 52) |
| p125FAK (Y373) Phos. | | T | D | D | Y | A | E | I | D | (SEQ ID NO: 53) |
| T-cell receptor ξ (Y110) | | E | G | L | Y | N | E | L | Q | (SEQ ID NO: 54) |
| T-cell receptor ξ (Y122) | | A | E | A | Y | S | E | I | G | (SEQ ID NO: 55) |

*Substrate sequences are from Cooper, J. A, (1990) Peptides and Protein Phosphorylation (B. E. Kemp,. ed.) CRC Press Inc. pp. 85–114; Geahlen, R. L. and Harrison, M. L. (1990) Peptides and Protein Phosphorylation (B. E. Kemp, ed.) CRC Press Inc. pp. 239–254; unpublished results from Cantley and Schafthausen labs and personal communication from T. Parsons; and Cheng, H. C., et al. (1991) J Biol. Chem. 266:17919–17925.

EXAMPLE 8

Determination of Amino Acid Sequence Motifs for a Growth Factor Receptor

The tyrosine-containing oriented degenerate peptide library was used to determine the substrate specificity of a growth factor receptor tyrosine kinase, the epidermal growth factor receptor (EGF receptor). Bar graphs summarizing the results of the library screening are shown in FIG. 6. The results of the library screening are summarized below in Tables 9, which presents the amino acid residues at degenerate positions having a relative abundance value equal to or greater than 1.0: More preferred amino acid residues within the motif have relative abundance values equal to or greater than 1.5 and are highlighted in bold-face type:

TABLE 9

Preferred amino acid residues at positions surrounding the phosphorylation site of the EGF receptor (SEQ ID NO: 13)

| -4 | -3 | -2 | -1 | 0 | +1 | +2 | +3 | +4 |
|---|---|---|---|---|---|---|---|---|
| E (1.61) | E (2.86) | E (2.55) | E (2.52) | Y | F (2.10) | E (1.90) | L (1.74) | V (1.59) |
| D (1.51) | D (1.81) | D (1.53) | D (2.12) |   | V (1.91) | F (1.60) | I (1.66) | F (1.43) |
| R (1.54) |   | A (1.25) | I (1.55) |   | I (1.68) | D (1.53) | F (1.63) | P (1.40) |
| A (1.5)  |   | Q (1.10) | N (1.09) |   | E (1.50) | V (1.40) | V (1.50) | E (1.31) |
|          |   | P (1.02) | V (1.02) |   | M (1.09) | I (1.27) | M (1.20) | L (1.30) |
|          |   |          |          |   | L (1.04) |          |          | I (1.28) |

Like the src family tyrosine kinases examined in Example 7, the EGF receptor preferentially phosphorylates sequences known substrates which differ from the determined amino acid sequence motif indicated in bold type.

TABLE 10

Comparison of the amino acid sequence motif determined by the peptide library to sequences at the same region of known substrates of the EGF receptor*

| Peptide/Protein | Site | | | | | | | | |
|---|---|---|---|---|---|---|---|---|---|
|  | -1 | -2 | -3 | -4 |  | +1 | +2 | +3 | +4 |
| EGF receptor amino acid sequence motif (SEQ ID NO: 13) | E | E | E | E | Y | F | E | L | V |
|  | D | D | D | D |   | V | F | I | F |
|  | R |   | A | I |   | I | D | F | P |
|  | A |   | Q | N |   | E | V | V | E |
|  |   |   | P | V |   | M | I | M | L |
|  |   |   |   |   |   | L |   |   | I |
| in vivo substrates |  |  |  |  |  |  |  |  |  |
| EGF receptor autophos. site (Y1069) | P | V | P | E | Y | I | N | Q | S | (SEQ ID NO: 58) |
| EGF receptor autophos. site (Y1086) | Q | N | P | V | Y | H | N | Q | P | (SEQ ID NO: 59) |
| EGF receptor autophos. site (Y111R) | G | N | P | E | Y | L | N | T | V | (SEQ ID NO: 60) |
| EGF receptor autophos. site (Y1148) | D | N | P | D | Y | Q | Q | D | F | (SEQ ID NO: 61) |
| EGF receptor autophos. site (Y1173) | E | N | A | E | Y | L | R | V | A | (SEQ ID NO: 62) |
| EGF receptor autophos. site (Y992)  | D | A | D | E | Y | L | I | P | Q | (SEQ ID NO: 63) |
| Lipocortin (Y21) | E | E | Q | E | Y | V | Q | T | V | (SEQ ID NO: 64) |
| Myosin light chain | V | D | E | M | Y | R | E | A | P | (SEQ ID NO: 65) |
| Myosin light chain | G | N | F | N | Y | V | E | F | T | (SEQ ID NO: 66) |
| Phospholipase C-γ (Y771) | A | E | P | D | Y | G | A | L | Y | (SEQ ID NO: 67) |
| Phospholipase C-γ (Y1254) | F | E | A | R | Y | Q | Q | P | F | (SEQ ID NO: 68) |
| in vitro substrates |  |  |  |  |  |  |  |  |  |
| Gastrin | E | E | E | A | Y | G | W | M | D | (SEQ ID NO: 69) |
| p21 ras peptide | G | Q | E | E | Y | S | A |   |   | (SEQ ID NO: 70) |

*Substrate sequences are from Geahlen, R. L. and Harrison, M. L. (1990) Peptides and Protein Phosphorylation (B. E. Kemp, ed.) CRC Press Inc. pp. 239–254; Varticovski, L., et al. (1988) Biochemistry L7:3682–3690: Wahl, M. I., et al. (1990) J. Biol. Chem. 265:3944–3948; and Kim, J. W., et al. (1990) J. Biol. Chem. 265:3940–3943.

with Glu at positions -2 and -3. The major difference between the optimal substrate for the cytosolic tyrosine kinases and the EGF receptor tyrosine kinase (a membrane-bound tyrosine kinase) is that the EGF receptor did not select strongly for peptides with Ile and Val at the -1 position and it had a broad selection for peptides with the general motif Hydrophobic-Xaa-Hydrophobic-Hydrophobic C-terminal to the phosphorylation site (SEQ ID NO: 56). Interestingly, this is the general motif recognized by Type III SH2 domains (PhosphoTyr-Hydrophobic-Xaa-Hydrophobic; (SEQ ID NO: 57) Songyang, Z., et al (1993) Cell 72:767–778).

The preferred amino acid residues at positions surrounding the phosphorylation site of the EGF receptor represent the amino acid sequence motif for the phosphorylation site determined by the library screening. This amino acid sequence motif can be compared to known in vitro and in vivo peptide substrates of the EGF receptor. This analysis is shown below in Table 10, with amino acid residues in the

EXAMPLE 9

Determination of Amino Acid Sequence Motifs for a the pp92$^{c\text{-}fps/fes}$ Tyrosine Kinase The tyrosine-containing oriented degenerate peptide library was used to determine the substrate specificity of the pp92$^{c\text{-}fps/fes}$ tyrosine kinase. Bar graphs summarizing the results of the library screening are shown in FIG. 7. The results of the library screening are summarized below in Table 11, which presents the amino acid residues at degenerate positions having a relative abundance value equal to or greater than 1.0: More preferred amino acid residues within the motif have relative abundance values equal to or greater than 1.5 and are highlighted in bold-face type:

TABLE 11

Preferred amino acid residues at positions surrounding the phosphorylation site of pp92$^{c\text{-}fps/fes}$ (SEQ ID NO: 14)

| -4 | -3 | -2 | -1 | 0 | +1 | +2 | +3 | +4 |
|---|---|---|---|---|---|---|---|---|
| E (2.01) | E (2.79) | E (2.72) | I (3.46) | Y | E (4.53) | E (2.70) | I (2.62) | E (2.68) |
| A (1.94) | A (1.60) | A (1.5) | E (1.94) |   | D (1.78) | D (2.70) | V (2.22) | I (1.77) |
| D (1.5) |   | G (1.23) | V (1.5) |   | A (1.25) | I (1.29) | E (2.06) | V (1.63) |
|   |   |   | D (1.14) |   |   | V (1.14) | M (1.29) | D (1.53) |
|   |   |   | L (1.10) |   |   |   | L (1.21) | G (1.14) |

The pp92$^{c\text{-}fps/fes}$ tyrosine kinase selected sequences similar to those selected by the src tyrosine kinases with the exception that Ile and Val instead of Phe were preferred at the +3 position. The SH2 domain of pp92$^{c\text{-}fps/fes}$, like that of pp60$^{v\text{-}src}$ is in Group I (Songyang, Z., et al (1993) *Cell* 72:767–778) and the two kinases prefer similar optimal phosphopeptides for binding. Thus, the preferred substrates of pp92$^{c\text{-}fps/fes}$ would produce products that would bind to the pp92$^{c\text{-}fps/fes}$ SH2 domain or to src-family SH2 domains.

The preferred amino acid residues at positions surrounding the phosphorylation site of pp92$^{c\text{-}fps/fes}$ represent the amino acid sequence motif for the phosphorylation site determined by the library screening. This amino acid sequence motif can be compared to known in vivo peptide substrates of pp92$^{c\text{-}fps/fes}$. This analysis is shown below in Table 12, with amino acid residues in the known substrates which differ from the determined amino acid sequence motif indicated in bold type.

TABLE 12

Comparison of the amino acid sequence motif determined by the peptide library to sequences at the same region of known substrates of c-fes/fps*

| Peptide/Protein | Sequence | | | | | | | | | |
|---|---|---|---|---|---|---|---|---|---|---|
|  | -4 | -3 | -2 | -1 | 0 | +1 | +2 | +3 | +4 | |
| c-fes/fps amino acid sequence motif (SEQ ID NO: 14) | E | E | E | I | Y | E | E | I | E | |
|  | A | A | A | E |   | D | D | V | I | |
|  | D |   | G | V |   | A | I | E | V | |
|  |   |   |   | D |   |   | V | M | D | |
|  |   |   |   | L |   |   |   | L | G | |
| Known in vivo substrates |   |   |   |   |   |   |   |   |   | |
| Chicken lactate dehydrenase (y238) | V | E | S | A | Y | E | V | I | R | (SEQ ID NO: 71) |
| Human Enolase (Y43) | S | T | G | I | Y | E | A | L | E | (SEQ ID NO: 72) |
| P140gag-fps (Y424) | E | D | G | V | Y | A | S | T | G | (SEQ ID NO: 73) |
| P110gag-fes (Y500) | A | D | G | I | Y | A | A | S | G | (SEQ ID NO: 74) |

*Substrate sequences are from Kemp, B. E. (ed.) (1990) Peptides and Protein Phosphorylation CRC Press Inc.

EXAMPLE 10

Kinetic Evaluation of Predicted Optimal Peptide Substrates

The peptide sequences predicted to be optimal substrates for the cyclin-dependent serine/threonine kinases and for pp60$^{v\text{-}src}$ tyrosine kinase were synthesized to determine whether they are indeed good substrates for these kinases. The peptide Ala-Arg-Arg-Pro-Met-Ser-Pro-Lys-Lys-Lys-Ala (SEQ ID NO: 75) was synthesized as a substrate for cyclin containing kinases. The peptide Ala-Glu-Glu-Glu-Ile-Tyr-Gly-Glu-Phe-Glu-Ala-Lys-Lys-Lys-Lys (SEQ ID NO: 76) was synthesized as a substrate for src tyrosine kinases and was also tested with the EGF receptor. The kinetic studies were carried out as follows. Purified kinases were immobilized on protein A beads (pp60$^{v\text{-}src}$ and EGF receptor) or GST beads (cyclin B/p33$^{cdc2}$ and cyclin A/p33$^{CDK2}$). Kinase reactions were performed in 20 μl of 50 mM Tris pH 7.0 buffer containing 50 mM NaCl, 10 mM MgCl$_2$ (v-src and cyclin-containing kinases) or MnCl$_2$ (EGF receptor), 10 μM ATP 5 μCi [γ-$^{32}$P]-ATP (3000 mCi/mmol, NEN) and various concentrations of peptides. For the experiment measuring the competitive inhibition of v-src activity by the src motif-containing peptide, 1 μM (final concentration) acid treated enolase was included. After 2 and a half minutes incubation, the supernatants were spotted on phosphocellulose paper (p81), washed four times with 75 mM phosphoric acid, and radioactivity counted on a scintillation counter. For phosphorylation of enolase, the reactions were stopped by adding SDS loading buffer and the proteins were resolved on 10% SDS-PAGE gels. The Km and Vmax were calculated using the Kaleidagraph computer software. The results are summarized below in Table 13.

EXAMPLE 11

Amino Acid Sequence Motifs for Additional Protein Tyrosine Kinases

The tyrosine-containing oriented degenerate peptide library was used to determine the amino acid sequence motifs for the substrates of five additional protein tyrosine kinases: lck, c-abl, PDGF receptor, FGF receptor and insulin receptor. The results of the library screening are summarized below in Tables 14–18, which presents the amino acid residues at degenerate positions having a relative abundance value equal to or greater than 1.0: More preferred amino acid residues within the motif have relative abundance values equal to or greater than 1.5 and are highlighted in bold-face

TABLE 13

Kinetics of Different Kinases Phosphorylating Synthetic Peptides

| Kinase | Peptide | Km (μM) | Ki (μM) | Vmax (μmol/min/mg) |
|---|---|---|---|---|
| cyclin B/p33$^{cdc2}$ | ARRPMSPKKKA | 2.4 | | |
| cyclin A/p33$^{CDK2}$ | ARRPMSPKKKA | 15 | | |
| pp60v-src | AEEEIYGEFEAKKKK | 32.9 | 8* | 0.8 |
|  | (Y15):IEKIGBGTYGVVYKGRHKTT | 139.4 | | 0.6 |
| EGF receptor | AEBEIYGEFEAKKKK | 34.0 | | |

*As assayed by inhibition of transphosphorylation of acid denatured enolase.

The peptide containing the predicted optimal substrate motif for the cyclin-containing kinases was phosphorylated by cyclin B/p33$^{cdc2}$ with a Km of 2.4 μM and by cyclin A/p33$^{CDK2}$ with a Km of 15 μM. These values indicate higher affinities than have previously been found with peptide substrates. The peptide containing the predicted optimal substrate motif for the src kinases was an excellent substrate for pp60$^{v-src}$, with a Km of 33 μM and Vmax of 0.8 μmol/mg/min. In comparison, a synthetic peptide based upon the site of tyrosine phosphorylation on p$_{33}$$^{cdc2}$ (Y15; SEQ ID NO: 77), the best substrate previously reported for pp60$^{v-src}$, was phosphorylated with a KM of 139 μM and Vmax of 0.6 mmol/mg/min. The src-substrate peptide was also found to be an excellent competitive inhibitor of enolase phosphorylation by pp60$^{v-src}$ (K$_{50\%}$=8 μM). In view of the similarity between optimal substrates for the various tyrosine kinases, it was not surprising that this peptide was also a good substrate for the EGF receptor (Km=34 μM).

type. "X" indicates that any amino acid is permissible at this amino acid position:

TABLE 14

Preferred amino acid residues at positions surrounding the phosphorylation site of lck (SEQ ID NO: 78)

| -4 | -3 | -2 | -1 | 0 | +1 | +2 | +3 | +4 |
|---|---|---|---|---|---|---|---|---|
| X | E (1.5) | X | I (3.4) | Y | G (2.2) | V (1.6) | L (2.3) | F (1.7) |
|  | G (1.1) |  | V (3.0) |  | A (1.6) | A (1.4) | V (2.2) | L (1.7) |
|  | P (1.1) |  | L (2.3) |  | M (1.4) | P (1.3) | F (2.2) | V (1.6) |
|  | A (1.1) |  | F (1.6) |  | E (1.3) | M (1.3) | I (2.0) | I (1.5) |
|  |  |  | M (1.3) |  | V (1.1) | I (1.3) | M (1.2) | P (1.3) |
|  |  |  |  |  |  | F (1.1) |  | M (1.3) |
|  |  |  |  |  |  | K (1.1) |  | K (1.3) |
|  |  |  |  |  |  | L (1.1) |  | G (1.1) |

TABLE 15

Preferred amino acid residues at positions surrounding the phosphorylation site of c-abl (SEQ ID NO: 79)

| -4 | -3 | -2 | -1 | 0 | +1 | +2 | +3 | +4 |
|---|---|---|---|---|---|---|---|---|
| A (1.7) | X | V (1.5) | I (3.2) | Y | A (2.2) | A (1.6) | P (2.3) | F (1.5) |
| R (1.3) |  | A (1.4) | V (1.8) |  | M (1.5) | V (1.4) | F (1.9) | L (1.4) |
| G (1.2) |  | P (1.4) | L (1.5) |  | Q (1.4) | F (1.3) | L (1.3) | I (1.3) |
| P (1.1) |  | I (1.3) | M (1.2) |  | G (1.3) | M (1.2) | I (1.2) | M (1.3) |
|  |  | G (1.2) |  |  | F (1.1) | Q (1.2) | V (1.1) | G (1.1) |
|  |  | E (1.1) |  |  |  | L (1.1) | A (1.1) | P (1.1) |
|  |  |  |  |  |  | I (1.1) |  |  |

65

TABLE 16

Preferred amino acid residues at positions surrounding the phosphorylation site of PDGF receptor (SEQ ID NO: 80)

| -4 | -3 | -2 | -1 | 0 | +1 | +2 | +3 | +4 |
|---|---|---|---|---|---|---|---|---|
| E (1.6) | E (2.0) | E (2.0) | E (2.2) | Y | V (2.0) | F (1.6) | I (1.9) | X |
| D (1.5) | D (1.5) | D (1.6) | D (1.6) |   | E (1.7) |   | V (1.7) |   |
|   |   |   |   |   | I (1.5) |   | F (1.5) |   |

TABLE 17

Preferred amino acid residues at positions surrounding the phosphorylation site of FGF receptor (SEQ ID NO: 81)

| -4 | -3 | -2 | -1 | 0 | +1 | +2 | +3 | +4 |
|---|---|---|---|---|---|---|---|---|
| A (2.1) | E (1.6) | E (1.8) | E (1.7) | Y | F (1.9) | F (2.0) | L (1.8) | F (1.7) |
| K (1.4) | A (1.5) | K (1.4) | I (1.4) |   | V (1.5) | V (1.4) | F (1.8) | L (1.4) |
| E (1.3) | F (1.4) | A (1.3) | V (1.2) |   | E (1.4) | M (1.4) | M (1.7) | M (1.4) |
| F (1.2) | K (1.4) | F (1.1) | D (1.1) |   | I (1.2) | I (1.2) | I (1.6) | V (1.4) |
| P (1.1) | M (1.1) | P (1.1) | F (1.1) |   | M (1.2) | L (1.2) | V (1.6) | E (1.3) |
| G (1.1) | G (1.1) | G (1.1) | A (1.1) |   | A (1.2) | E (1.1) | E (1.2) | I (1.3) |
|   | I (1.1) | V (1.1) | L (1.1) |   | K (1.2) | P (1.1) |   | P (1.3) |
|   | V (1.1) |   |   |   |   | K (1.1) |   |   |

TABLE 18

Preferred amino acid residues at positions surrounding the phosphorylation site of insulin receptor (SEQ ID NO: 82)

| -4 | -3 | -2 | -1 | 0 | +1 | +2 | +3 | +4 |
|---|---|---|---|---|---|---|---|---|
| X | E (1.7) | E (1.8) | E (1.6) | Y | M (2.8) | M (2.2) | M (2.2) | M (1.9) |
|   | G (1.3) | A (1.4) | N (1.5) |   | F (1.6) | F (1.6) | F (1.9) | F (1.9) |
|   | A (1.3) | G (1.3) | D (1.5) |   | A (1.4) | V (1.3) | I (1.5) | E (1.5) |
|   | F (1.2) | P (1.3) | A (1.2) |   | E (1.3) | E (1.3) | E (1.5) | V (1.4) |
|   | N (1.1) | N (1.1) | I (1.2) |   | V (1.1) | A (1.2) | V (1.4) | L (1.3) |
|   | M (1.1) |   | P (1.1) |   |   | D (1.1) |   | I (1.2) |
|   |   |   | G (1.1) |   |   | L (1.1) |   | G (1.1) |
|   |   |   |   |   |   | I (1.1) |   |   |

EXAMPLE 11

Amino Acid Sequence Motifs for Additional Protein Serine/Threonine Kinases

The serine-containing oriented degenerate peptide library was used to determine the amino acid sequence motifs for the substrates of five additional protein serine/threonine kinases: casein kinase II, NIMA, phosphorylase kinase, Cam kinase II and Erk1. The results of the library screening are summarized below in Tables 19–23, which presents the amino acid residues at degenerate positions having a relative abundance value equal to or greater than 1.0: More preferred amino acid residues within the motif have relative abundance values equal to or greater than 1.5 and are highlighted in bold-face type.

TABLE 19

Preferred amino acid residues at positions surrounding the phosphorylation site of casein kinase II (SEQ ID NO: 83)

| -4 | -3 | -2 | -1 | 0 | +1 | +2 | +3 | +4 |
|---|---|---|---|---|---|---|---|---|
| E (2.2) | D (3.2) | E (2.8) | E (2.7) | S | E (3.0) | D (3.4) | E (3.4) | E (4.1) |
| D (1.8) | E (2.2) | D (2.6) | D (2.0) | T | D (2.9) | E (2.3) | D (3.0) | D (2.1) |
| A (1.8) | G (1.4) | A (1.1) | G (1.2) |   | A (1.5) | A (1.6) | A (1.4) | I (1.3) |
| G (1.2) | A (1.3) | G (1.1) | A (1.2) |   |   |   |   |   |
|   |   |   | M (1.2) |   |   |   |   |   |

TABLE 20

Preferred amino acid residues at positions surrounding the phosphorylation site of NIMA (SEQ ID NO: 84)

| -4 | -3 | -2 | -1 | 0 | +1 | +2 | +3 | +4 |
|---|---|---|---|---|---|---|---|---|
| R (2.0) | F (7.3) | R (4.5) | R (4.6) | S | R (2.6) | R (2.0) | M (1.9) | I (2.1) |
| N (1.5) | L (2.3) | K (1.2) | K (1.6) | T | I (1.7) | I (2.0) | I (1.8) | F (1.7) |
| F (1.4) | M (1.7) | N (1.2) | M (1.4) |   | V (1.7) | M (1.9) | F (1.7) | M (1.7) |
| M (1.2) |   |   | Q (1.1) |   | M (1.7) | V (1.6) | V (1.5) | G (1.3) |
| Q (1.1) |   |   |   |   | L (1.4) | F (1.5) | L (1.2) | L (1.2) |
| G (1.1) |   |   |   |   | Q (1.2) | L (1.2) | G (1.1) | V (1.2) |

TABLE 21

Preferred amino acid residues at positions surrounding the phosphorylation site of Phosphorylase Kinase (SEQ ID NO: 85)

| -4 | -3 | -2 | -1 | 0 | +1 | +2 | +3 | +4 |
|---|---|---|---|---|---|---|---|---|
| F (1.7) | R (5.7) | M (2.0) | M (2.2) | S | F (3.9) | F (2.5) | L (2.1) | F (2.3) |
| M (1.5) | K (2.5) | R (1.8) | F (2.0) | T | I (2.4) | R (2.0) | I (2.0) | L (1.8) |
| K (1.4) |   | Q (1.7) | L (1.8) |   | M (1.7) | K (2.0) | M (1.2) | I (1.7) |
| I (1.4) |   | F (1.6) | I (1.5) |   | L (1.6) | M (1.4) | P (1.2) | V (1.4) |
| H (1.4) |   | K (1.4) | K (1.2) |   | V (1.2) | I (1.2) | V (1.1) | P (1.3) |
| V (1.1) |   | L (1.1) | V (1.1) |   |   |   |   | M (1.2) |

TABLE 22

Preferred amino acid residues at positions surrounding the phosphorylation site of Cam Kinase II (SEQ ID NO: 86)

| -4 | -3 | -2 | -1 | 0 | +1 | +2 | +3 | +4 |
|---|---|---|---|---|---|---|---|---|
| K (2.3) | R (3.9) | Q (4.5) | Q (2.1) | S | F (4.8) | D (2.5) | L (1.7) | F (1.7) |
| F (1.5) | K (2.7) | M (1.8) | M (2.0) | T | I (1.9) | E (1.7) | M (1.7) | K (1.4) |
| D (1.2) | F (1.3) | K (1.1) | K (1.9) |   | M (1.7) | I (1.5) | K (1.6) | M (1.3) |
| H (1.2) | M (1.2) | A (1.1) | L (1.8) |   | L (1.6) | M (1.3) | I (1.5) | V (1.3) |
| M (1.1) |   | F (1.1) | F (1.5) |   | V (1.3) | K (1.3) | V (1.3) | L (1.3) |
|   |   |   | A (1.1) |   |   | V (1.2) | Q (1.3) | I (1.2) |
|   |   |   |   |   |   | L (1.1) | G (1.1) | P (1.1) |

TABLE 23

Preferred amino acid residues at positions surrounding the phosphorylation site of Erk1 (SEQ ID NO: 87)

| -4 | -3 | -2 | -1 | 0 | +1 | +2 | +3 | +4 |
|---|---|---|---|---|---|---|---|---|
| T (2.0) | G (3.2) | P (6.5) | L (2.0) | S | P | G (2.1) | P (2.4) | F (2.3) |
| P (1.5) | P (1.5) | L (2.1) | M (1.9) | T |   | P (1.9) | F (1.9) | Y (1.7) |
| S (1.4) | E (1.5) | I (1.3) | P (1.7) |   |   | F (1.3) | G (1.5) | I (1.2) |
| Q (1.3) | Y (1.5) | V (1.1) | K (1.4) |   |   | T (1.2) | Y (1.5) | L (1.2) |
| I (1.2) | Q (1.2) |   | Q (1.2) |   |   | L (1.2) | L (1.1) |   |
| V (1.2) |   |   | T (1.1) |   |   |   | I (1.1) |   |
| N (1.2) |   |   |   |   |   |   |   |   |
| E (1.2) |   |   |   |   |   |   |   |   |

EXAMPLE 13

Comparison of Optimal Substrates of abl and src Kinases

Figure 8A:
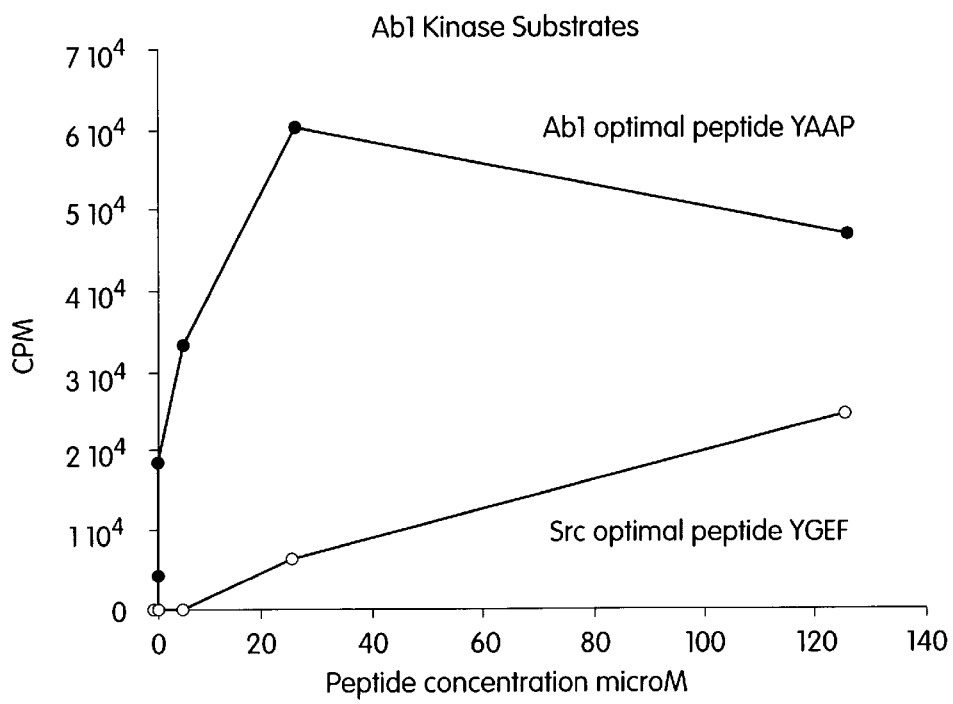
FIGS. 8A–B are graphs depicting the in vitro phosphorylation of synthetic src and abl optimal peptides by the abl protein tyrosine kinase (panel A) or the src protein tyrosine kinase (panel B).
Figure 8B:
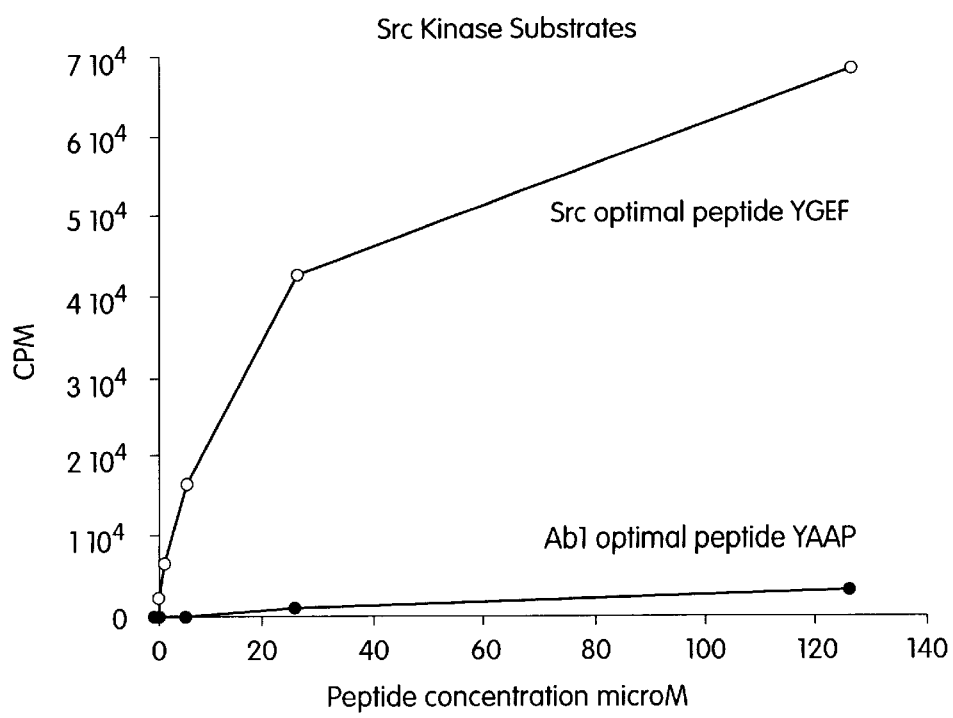

Optimal substrate peptides for the src and abl protein tyrosine kinases were synthesized based on the determined amino acid sequence motifs for each kinase. The synthetic src and able optimal peptides were compared for their ability to act as specific, high affinity substrates for src or abl. The synthetic src optimal peptide had the amino acid sequence AEEEIYGEFEAKKKK (SEQ ID NO: 76). The synthetic abl optimal peptide had the amino acid sequence EAIYAAP-FAKKK (SEQ ID NO: 88). The two peptides were phosphorylated by GST-fusion constructs of src and abl. Different concentrations of peptides were phosphorylated by the kinases in reactions containing 10 mM $MnCl_2$, 50 mM Tris pH 7.5, 2 mM DTT, 10 $\mu$M ATP and 5 $\mu$Ci [$\gamma$-$^{32}$P]-ATP for 3 minutes at 25° C. The amount of radioactivity incorporated into the peptides was determined using a phosphocellulose assay. The results of the phosphorylation experiments are illustrated graphically in FIG. 8, panels A and B. The synthetic src optimal peptide was found to be an excellent substrate for src ($K_m$=33 $\mu$M, $V_{max}$=0.8 $\mu$mol/mg/min)(see FIG. 8B), but a poor substrate for abl. Similarly, the synthetic abl optimal peptide was favorably phosphorylated by abl (Km=4 $\mu$M, Vmax=0.5 $\mu$mol/mg/min)(see FIG. 8A), but poorly phosphorylated by src.

EXAMPLE 14

Preferential Phosphorylation of Sequences that Bind to Specific SH2 Domains

A comparison of the optimal peptide substrates of protein tyrosine kinases (PTKs) to the phosphopeptide motifs selected by individual Src homology region 2 (SH2) domains (see Songyang, Z. et al. (1993) *Cell* 72:767–778; Songyang, Z. et al. (1994) *Mol. Cell. Biol.* 14:2777–2785) revealed that individual protein tyrosine kinases preferentially phosphorylate sequences that bind to specific SH2 domains. The receptor PTKs phosphorylated peptides with the general motif Tyr-hydrophobic-X-hydrophobic, characteristic of peptides recognized by Group III SH2 domains (e.g., p85, PLC-γ, SHPTP2). In contrast, the SH2-containing PTKs preferentially phosphorylated peptides with the motif Tyr-hydrophilic-hydrophilic-hydrophobic, recognized by Group I SH2 domains. Even more interesting is the finding that some of the SH2-containing PTKs selectively phosphorylate sites recognized by their own SH2 domains. For example, the optimal substrate for the fps/fes PTK contains the motif YEEI/V and the optimal substrate for the fps/fes SH2 domain is pYEEV/I. This selection is not due to the ability of the SH2 domain to protect the product from phosphatases or to present the substrate to the catalytic domain since similar motifs were found in experiments using kinase constructs lacking SH2 domains.

Figure 9:
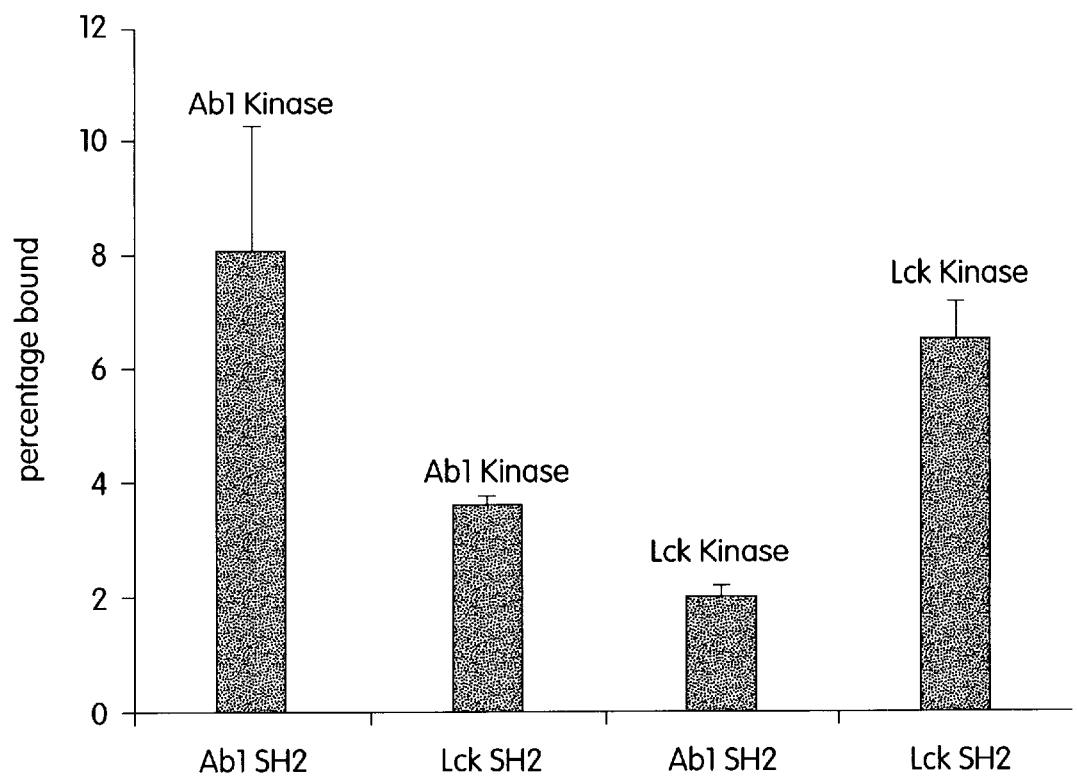
FIG. 9 is a bar graph depicting the binding of the abl and lck SH2 domains to phosphopeptides phosphorylated by either the abl protein tyrosine kinase or the lck protein tyrosine kinase.

To investigate further whether cytosolic PTKs preferentially phosphorylate sites recognized by their own or related SH2 domains, the ability of the abl or lck SH2 domain to bind peptides phosphorylated by either abl or lck was examined. In these experiments, a tyrosine-containing degenerate peptide library as described in Example 1 was phosphorylated by purified lck or GST-c-abl with [γ-$^{32}$P]-ATP such that a small fraction (0.001%) of the peptides were phosphorylated. Synthetic degenerate phosphopeptides (30 μM; as described in Songyang, Z. et al. (1993) *Cell* 72:767–778) were also added to the reaction buffer to prevent binding of the labeled peptides to endogenous SH2 domains in the kinases. The labeled phosphopeptide mixture was added to immobilized GST-SH2 domains (300 nM) with 1 μM of synthetic phosphopeptides. To correct for background binding, control experiments were performed in the same solution with 20 mM phenyl phosphate. After 2 hours of incubation, the pellets were washed quickly with 1 ml ice-cold PBS and the radioactivity associated with the pellets was measured. The results are shown graphically in FIG. 9. The plot shows the percentages of the total phosphorylated peptides that bound to SH2 domains of c-abl and lck. Error bars indicate the standard error (n=3). The data indicate that the abl SH2 domain bound a large fraction of peptides phosphorylated by the abl PTK but a smaller fraction of peptides phosphorylated by the lck PTK. In contrast, the lck SH2 domain preferentially bound peptides phosphorylated by the lck PTK.

EXAMPLE 15

Mutation of the RET Protein Tyrosine Kinase Affects Substrate Specificity

The following studies with the RET receptor protein tyrosine kinase provide evidence that catalytic site specificity of PTKs is critical for fidelity in downstream signaling. A germline mutation affecting the catalytic core of the RET receptor PTK results in an autosomal dominantly-inherited cancer syndrome referred to as multiple endocrine neoplasia type 2B (MEN 2B) (see Hofstra, R. M. et al. (1994) *Nature* 367:375–376; Eng, C. et al. (1994) *Hum. Mol. Genet.* 3:237–241; and Carlson, K. M. et al. (1994) *Proc. Natl. Acad. Sci USA* 91:1579–1583). The mutated residue is in a region of domain VIII of the enzyme that has been implicated in peptide substrate selectivity of protein Ser/Thr kinases (see Songyang, Z. et al. (1994) *Current Biology* 4:973–982; Hanks, S. K. et al. (1988) *Science* 241:42–52; and Knighton, D. R. et al. (1991) *Science* 253:414–420). The wild-type RET protein has Met at amino acid position 918, as found in most other receptor PTKs. In the mutant RET protein found in MEN 2B, this residue is mutated to Thr, making this region more similar to SH2-containing PTKs.

Figure 10:
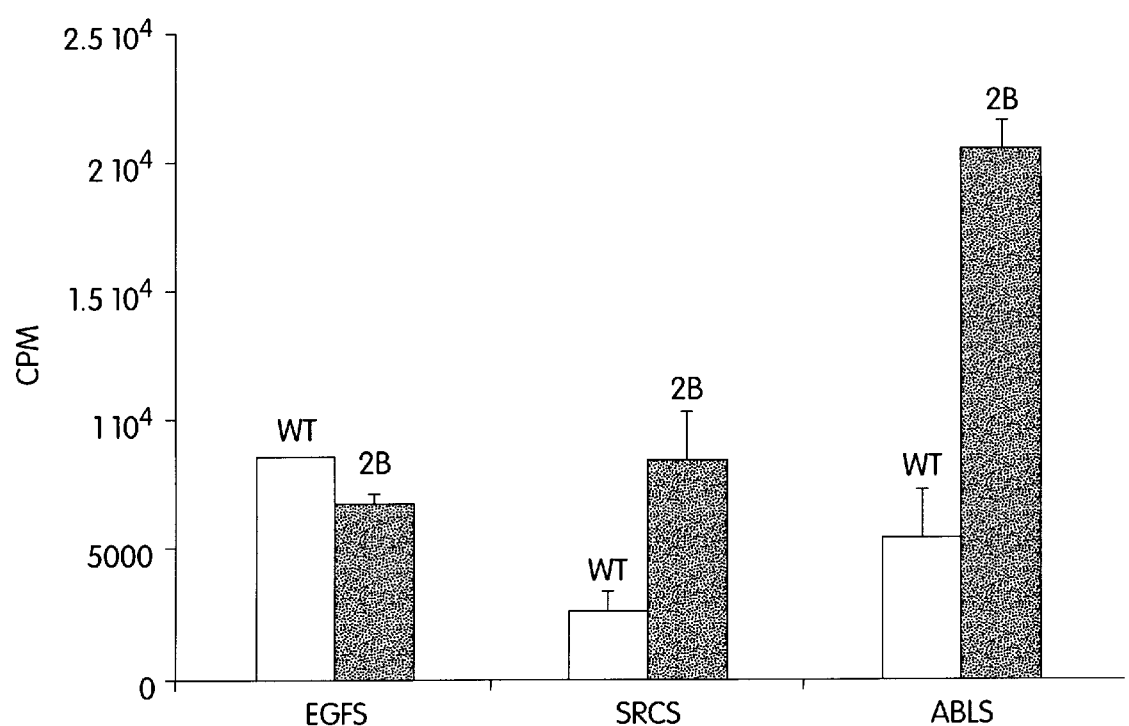
FIG. 10 is a bar graph depicting the phosphorylation of optimal peptide substrates for src, abl or EGF receptor by either wild-type RET receptor protein tyrosine kinase or mutant (MEN 2B) RET receptor protein tyrosine kinase.

The ability of baculovirus-expressed cytoplasmic domains of either wild-type (WT) or MEN 2B mutant (2B) RET to phosphorylate three different peptide substrates was examined. The RET proteins were immunoprecipitated from insect cells using phosphotyrosine-specific antibodies and used to phosphorylate either an EGF receptor optimal substrate peptide, an abl optimal substrate peptide or a src optimal substrate peptide (each at 10 μM) in the presence of [γ-32P]-ATP. The amount of radioactivity incorporated was determined using a phosphocellulose assay. The incorporated activity was normalized such that RET WT and 2B had the same autophosphorylation activity. The results are shown graphically in FIG. 10. The error bars indicate the difference between two experiments. The data indicate that the wild-type RET protein preferentially phosphorylates the optimal peptide substrate for the EGF receptor while the mutant RET protein preferentially phosphorylates the optimal peptide substrates for abl and src. These data suggest that phosphorylation of inappropriate substrates by the MEN 2B RET PTK results in the stimulation of pathways normally mediated by SH2-containing PTKs, probably involving signaling proteins with Group I SH2 domains.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A substrate for lck, which is a peptide consisting of an amino acid sequence:

$$Y_1\text{-Xaa1-Xaa2-Xaa3-Xaa4-Xaa5-Xaa6-Xaa7-Xaa8-Xaa9-}Y_2$$

wherein $Y_1$ is hydrogen, an amino-derivative group selected from the group consisting of epoxysuccinyl, cholesteryl, aryl, aralkyl and acyl groups, the amino derivative group being selected such that the peptide is a substrate for lck, or a dipeptide having an amino acid sequence Met-Ala, $Y_2$ is hydrogen, a carboxy-derivative group selected from the group consisting of alcohol, aldehyde, epoxysuccinate, acid halide, carbonyl, halomethane, and diazomethane groups, the carboxy-derivative group being selected such that the peptide is a substrate for lck, or a tetrapeptide having an amino acid sequence Ala-Lys-Lys-Lys (SEQ ID NO:89), Xaa1 is a non-phosphorylatable naturally occurring alpha-amino acid, Xaa2 is Glu, Gly, Pro or Ala, Xaa3 is a non-phosphorylatable naturally occurring alpha-amino acid, Xaa4 is Ile, Val, Leu, Phe or Met, Xaa5 is Tyr, Xaa6 is Gly, Ala, Met, Glu or Val, Xaa7 is Val, Ala, Pro, Met, Ile, Phe, Lys or Leu, Xaa8 is Leu, Val, Phe, Ile or Met, Xaa9 is Phe, Leu, Val, Ile, Pro, Met, Lys or Gly; and wherein the amino acid sequence Xaa1-Xaa2-Xaa3-Xaa4-Xaa5-Xaa6-Xaa7-Xaa8-Xaa9 consists of the amino acid sequence of SEQ ID NO:78.

2. A substrate for lck, which is a peptide having an amino acid sequence:

$$Y_1\text{-Xaa1-Xaa2-Xaa3-Xaa4-Xaa5-Xaa6-Xaa7-Xaa8-Xaa9-}Y_2$$

wherein $Y_1$ is hydrogen, an amino-derivative group selected from the group consisting of epoxysuccinyl, cholesteryl, aryl, aralkyl and acyl groups, the amino derivative group being selected such that the peptide is a substrate for lck, or a dipeptide having an amino acid sequence Met-Ala;

$Y_2$ is hydrogen, a carboxy-derivative group selected from the group consisting of alcohol, aldehyde, epoxysuccinate, acid halide, carbonyl, halomethane, and diazomethane groups, the carboxy-derivative group being selected such that the peptide is a substrate for lck, or a tetrapeptide having an amino acid sequence Ala-Lys-Lys-Lys (SEQ ID NO: 89);

Xaa1 is any alpha-amino acid;

Xaa2 is Glu, Gly, Pro, or Ala;

Xaa3 is any alpha-amino acid;

Xaa4 is Ile, Val, Leu, Phe or Met;

Xaa5 is Tyr;

Xaa6 is Gly, Ala, Met, Glu, or Val;
Xaa7 is Val, Ala, Pro, Met, Ile, Phe, Lys, or Leu;
Xaa8 is Leu, Val, Phe, Ile or Met; and
Xaa9 is Phe, Leu, Val, Ile, Pro, Met, Lys or Gly;
wherein Xaa2 is Glu, Xaa4 is Ile, Val, Leu or Phe, Xaa6 is Gly or Ala, Xaa7 is Val, Xaa8 is Leu, Val, Phe or Ile, and Xaa9 is Phe, Leu, Val or Ile; and
wherein Xaa1-Xaa2-Xaa3-Xaa4-Xaa5-Xaa6-Xaa7-Xaa8-Xaa9 is SEQ ID NO:90.

3. A method for inhibiting kinase activity of lck comprising contacting lck in vitro with an inhibitory amount of the substrate for lck as claimed in claim 2, such that kinase activity of lck toward another lck substrate is inhibited.

4. A pseudosubstrate for lck, which is a peptide consisting of an amino acid sequence:

$Y_1$-Xaa1-Xaa2-Xaa3-Xaa4-Xaa5-Xaa6-Xaa7-Xaa8-Xaa9-$Y_2$ wherein $Y_1$ is hydrogen, an amino-derivative group selected from the group consisting of epoxysuccinyl, cholesteryl, aryl, aralkyl and acyl groups, the amino derivative group being selected such that the peptide is a pseudo substrate for lck, or a dipeptide having an amino acid sequence Met-Ala, $Y_2$ is hydrogen, a carboxy-derivative group selected from the group consisting of alcohol, aldehyde, epoxysuccinate, acid halide, carbonyl, halomethane, and diazomethane groups, the carboxy-derivative group being selected such that the peptide is a substrate for lck, or a tetrapeptide having an amino acid sequence Ala-Lys-Lys-Lys (SEQ ID NO:89), Xaa1 is a non-phosphorylatable naturally occurring alpha-amino acid, Xaa2 is Glu, Gly, Pro or Ala, Xaa3 is a non-phosphorylatable naturally occurring alpha-amino acid, Xaa4 is Ile, Val, Leu, Phe or Met, Xaa5 is Phe, Xaa6 is Gly, Ala, Met, Glu or Val, Xaa7 is Val, Ala, Pro, Met, Ile, Phe, Lys or Leu, Xaa8 is Leu, Val, Phe, Ile or Met, Xaa9 is Phe, Leu, Val, Ile, Pro, Met, Lys or Gly; and wherein the amino acid sequence Xaa1-Xaa2-Xaa3-Xaa4-Xaa5-Xaa6-Xaa7-Xaa8-Xaa9 is selected from the group consisting of the amino acid sequence of SEQ ID NO:90 and the amino acid sequence of SEQ ID NO:91.

5. The pseudosubstrate of claim 4, wherein the amino acid sequence Xaa1-Xaa2-Xaa3-Xaa4-Xaa5-Xaa6-Xaa7-Xaa8-Xaa9 consists of the amino acid sequence of SEQ ID NO:92; and wherein Xaa5 is Phe or His.

6. A method for inhibiting kinase activity of lck comprising contacting lck in vitro with an inhibitory amount of the pseudosubstrate for lck as claimed in claim 4, such that kinase activity of lck toward an lck substrate is inhibited.

* * * * *

SEQUENCE LISTING

```
<160> NUMBER OF SEQ ID NOS: 92

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence:peptide
<220> FEATURE:
<221> NAME/KEY: SITE
<222> LOCATION: (1)..(9)
<223> OTHER INFORMATION: Xaa, if present, is any amino acid
<220> FEATURE:
<221> NAME/KEY: SITE
<222> LOCATION: (10)
```

<223> OTHER INFORMATION: Xaa is any amino acid
<220> FEATURE:
<221> NAME/KEY: SITE
<222> LOCATION: (11)
<223> OTHER INFORMATION: Xaa is Ser, Thr, or Tyr
<220> FEATURE:
<221> NAME/KEY: SITE
<222> LOCATION: (12)
<223> OTHER INFORMATION: Xaa is any amino acid
<220> FEATURE:
<221> NAME/KEY: SITE
<222> LOCATION: (13)..(21)
<223> OTHER INFORMATION: Xaa, if present, is any amino acid

<400> SEQUENCE: 1

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
            20

<210> SEQ ID NO 2
<211> LENGTH: 51
<212> TYPE: PRT
<213> ORGANISM: Artificial Sequence
<220> FEATURE:
<223> OTHER INFORMATION: Description of Artificial Sequence:peptide
<220> FEATURE:
<221> NAME/KEY: SITE
<222> LOCATION: (1)..(24)
<223> OTHER INFORMATION: Xaa, if present, is any amino acid
<220> FEATURE:
<221> NAME/KEY: SITE
<222> LOCATION: (25)
<223> OTHER INFORMATION: Xaa is any amino acid
<220> FEATURE:
<221> NAME/KEY: SITE
<222> LOCATION: (26)
<223> OTHER INFORMATION: Xaa is Ser, Thr, or Tyr
<220> FEATURE:
<221> NAME/KEY: SITE
<222> LOCATION: (27)
<223> OTHER INFORMATION: Xaa is any amino acid
<220> FEATURE:
<221> NAME/KEY: SITE
<222> LOCATION: (28)..(51)
<223> OTHER INFORMATION: Xaa, if present, is any amino acid

<400> SEQUENCE: 2

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa
    50

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:peptide
<220> FEATURE:
<221> NAME/KEY: SITE
<222> LOCATION: (3)..(6)
<223> OTHER INFORMATION: Xaa is any amino acid
<220> FEATURE:
<221> NAME/KEY: SITE
<222> LOCATION: (7)
<223> OTHER INFORMATION: Xaa is Ser, Thr, or Tyr
<220> FEATURE:

```
<221> NAME/KEY: SITE
<222> LOCATION: (8)..(11)
<223> OTHER INFORMATION: Xaa is any amino acid

<400> SEQUENCE: 3

Met Ala Xaa Xaa Xaa Xaa Xaa Xaa Xaa Xaa Xaa Ala Lys Lys Lys
 1               5                  10                  15

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:Peptide
      substrate for a protein kinase comprising this
      amino acid sequence
<220> FEATURE:
<221> NAME/KEY: SITE
<222> LOCATION: (1)..(4)
<223> OTHER INFORMATION: Xaa is any amino acid
<220> FEATURE:
<221> NAME/KEY: SITE
<222> LOCATION: (5)
<223> OTHER INFORMATION: Xaa is Ser, Thr, or Tyr
<220> FEATURE:
<221> NAME/KEY: SITE
<222> LOCATION: (6)..(9)
<223> OTHER INFORMATION: Xaa is any amino acid

<400> SEQUENCE: 4

Xaa Xaa Xaa Xaa Xaa Xaa Xaa Xaa Xaa
 1               5

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence:substrate
<220> FEATURE:
<221> NAME/KEY: SITE
<222> LOCATION: (1)..(18)
<223> OTHER INFORMATION: Xaa, if present, is any amino acid
<220> FEATURE:
<221> NAME/KEY: SITE
<222> LOCATION: (19)
<223> OTHER INFORMATION: Xaa is any amino acid
<220> FEATURE:
<221> NAME/KEY: SITE
<222> LOCATION: (20)
<223> OTHER INFORMATION: Xaa is Ser, Thr, or Tyr
<220> FEATURE:
<221> NAME/KEY: SITE
<222> LOCATION: (21)
<223> OTHER INFORMATION: Xaa is any amino acid
<220> FEATURE:
<221> NAME/KEY: SITE
<222> LOCATION: (22)..(39)
<223> OTHER INFORMATION: Xaa, if present, is any amino acid

<400> SEQUENCE: 5

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa
        35

<210> SEQ ID NO 6
<211> LENGTH: 9
<212> TYPE: PRT
<213> ORGANISM: Artificial Sequence
```

```
<220> FEATURE:
<223> OTHER INFORMATION: Description of Artificial Sequence:Preferred
      phosphorylation site of protein kinase A
<220> FEATURE:
<221> NAME/KEY: SITE
<222> LOCATION: (1)
<223> OTHER INFORMATION: Xaa is Arg or His
<220> FEATURE:
<221> NAME/KEY: SITE
<222> LOCATION: (2)
<223> OTHER INFORMATION: Xaa is Arg or His
<220> FEATURE:
<221> NAME/KEY: SITE
<222> LOCATION: (3)
<223> OTHER INFORMATION: Xaa is Arg, Lys, or His
<220> FEATURE:
<221> NAME/KEY: SITE
<222> LOCATION: (4)
<223> OTHER INFORMATION: Xaa is Arg or His
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (6)
<223> OTHER INFORMATION: Xaa is Ile, Met, Phe, Leu, or Val
<220> FEATURE:
<221> NAME/KEY: SITE
<222> LOCATION: (7)
<223> OTHER INFORMATION: Xaa is Ile, Val, or Phe
<220> FEATURE:
<221> NAME/KEY: SITE
<222> LOCATION: (8)
<223> OTHER INFORMATION: Xaa is Phe, Ile, Met, Val, or Leu
<220> FEATURE:
<221> NAME/KEY: SITE
<222> LOCATION: (9)
<223> OTHER INFORMATION: Xaa is Ile, Leu, Phe, Met, or Val

<400> SEQUENCE: 6

Xaa Xaa Xaa Xaa Xaa Xaa Xaa Xaa Xaa
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:composite
      sequence motif
<220> FEATURE:
<221> NAME/KEY: SITE
<222> LOCATION: (1)
<223> OTHER INFORMATION: Xaa is Arg, His, Asn, or Gln
<220> FEATURE:
<221> NAME/KEY: SITE
<222> LOCATION: (2)
<223> OTHER INFORMATION: Xaa is Arg, His, Pro, Met, Val, or Ile
<220> FEATURE:
<221> NAME/KEY: SITE
<222> LOCATION: (3)
<223> OTHER INFORMATION: Xaa is Pro, Met, or Leu
<220> FEATURE:
<221> NAME/KEY: SITE
<222> LOCATION: (4)
<223> OTHER INFORMATION: Xaa is Met, Gln, Ala, Asn, Arg, or Lys
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (7)
<223> OTHER INFORMATION: Xaa is Pro, Lys, Met, Ala, Val, or Arg
<220> FEATURE:
<221> NAME/KEY: SITE
<222> LOCATION: (8)
```

-continued

```
<223> OTHER INFORMATION: Xaa is Lys, Arg, or Pro
<220> FEATURE:
<221> NAME/KEY: SITE
<222> LOCATION: (9)
<223> OTHER INFORMATION: Xaa is Lys, Ile, Arg, or Asn

<400> SEQUENCE: 7

Xaa Xaa Xaa Xaa Xaa Pro Xaa Xaa Xaa
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:Preferred
      phosphorylation site of cyclinB/p34cdc2
<220> FEATURE:
<221> NAME/KEY: SITE
<222> LOCATION: (1)
<223> OTHER INFORMATION: Xaa is Arg or His
<220> FEATURE:
<221> NAME/KEY: SITE
<222> LOCATION: (2)
<223> OTHER INFORMATION: Xaa is Arg, Pro, Met, Val, or Ile
<220> FEATURE:
<221> NAME/KEY: SITE
<222> LOCATION: (3)
<223> OTHER INFORMATION: Xaa is Pro or Met
<220> FEATURE:
<221> NAME/KEY: SITE
<222> LOCATION: (4)
<223> OTHER INFORMATION: Xaa is Met, Gln, Ala, Asn, Arg, or Lys
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (7)
<223> OTHER INFORMATION: Xaa is Pro, Lys, Met, Ala, or Val
<220> FEATURE:
<221> NAME/KEY: SITE
<222> LOCATION: (8)
<223> OTHER INFORMATION: Xaa is Lys, Arg, or Pro
<220> FEATURE:
<221> NAME/KEY: SITE
<222> LOCATION: (9)
<223> OTHER INFORMATION: Xaa is Lys, Ile, or Arg

<400> SEQUENCE: 8

Xaa Xaa Xaa Xaa Xaa Pro Xaa Xaa Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:Preferred
      phosphorylation site of cyclinA/p34cdk2
<220> FEATURE:
<221> NAME/KEY: SITE
<222> LOCATION: (1)
<223> OTHER INFORMATION: Xaa is Arg, His, Asn, or Gln
<220> FEATURE:
<221> NAME/KEY: SITE
<222> LOCATION: (2)
<223> OTHER INFORMATION: Xaa is Arg, His, Val, Pro, or Met
<220> FEATURE:
<221> NAME/KEY: SITE
<222> LOCATION: (3)
<223> OTHER INFORMATION: Xaa is Pro, Met, or Leu
<220> FEATURE:
<221> NAME/KEY: SITE
<222> LOCATION: (4)
```

<223> OTHER INFORMATION: Xaa is Met, Gln, Arg, Asn, or Ala
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (7)
<223> OTHER INFORMATION: Xaa is Pro, Met, Arg, Val, or Lys
<220> FEATURE:
<221> NAME/KEY: SITE
<222> LOCATION: (8)
<223> OTHER INFORMATION: Xaa is Lys or Arg
<220> FEATURE:
<221> NAME/KEY: SITE
<222> LOCATION: (9)
<223> OTHER INFORMATION: Xaa is Lys or Asn

<400> SEQUENCE: 9

Xaa Xaa Xaa Xaa Xaa Pro Xaa Xaa Xaa
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:composite
      sequence motif
<220> FEATURE:
<221> NAME/KEY: SITE
<222> LOCATION: (1)..(2)
<223> OTHER INFORMATION: Xaa is Glu or Asp
<220> FEATURE:
<221> NAME/KEY: SITE
<222> LOCATION: (3)
<223> OTHER INFORMATION: Xaa is Glu, Asp, Gly, or Asn
<220> FEATURE:
<221> NAME/KEY: SITE
<222> LOCATION: (4)
<223> OTHER INFORMATION: Xaa is Ile, Val, Leu, or Pro
<220> FEATURE:
<221> NAME/KEY: SITE
<222> LOCATION: (6)
<223> OTHER INFORMATION: Xaa is Gly, Glu, or Asp
<220> FEATURE:
<221> NAME/KEY: SITE
<222> LOCATION: (7)
<223> OTHER INFORMATION: Xaa is Glu or Asp
<220> FEATURE:
<221> NAME/KEY: SITE
<222> LOCATION: (8)
<223> OTHER INFORMATION: Xaa is Phe, Ile, Leu, Val, or Met
<220> FEATURE:
<221> NAME/KEY: SITE
<222> LOCATION: (9)
<223> OTHER INFORMATION: Xaa is Glu, Phe, or Asp

<400> SEQUENCE: 10

Xaa Xaa Xaa Xaa Tyr Xaa Xaa Xaa Xaa
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:Preferred
      phosphorylation site of pp60c-src
<220> FEATURE:
<221> NAME/KEY: SITE
<222> LOCATION: (1)..(2)
<223> OTHER INFORMATION: Xaa is Glu or Asp
<220> FEATURE:
<221> NAME/KEY: SITE
<222> LOCATION: (3)

```
<223> OTHER INFORMATION: Xaa is Glu, Asp, or Gly
<220> FEATURE:
<221> NAME/KEY: SITE
<222> LOCATION: (4)
<223> OTHER INFORMATION: Xaa is Ile, Val, Leu, or Pro
<220> FEATURE:
<221> NAME/KEY: SITE
<222> LOCATION: (6)
<223> OTHER INFORMATION: Xaa is Gly or Glu
<220> FEATURE:
<221> NAME/KEY: SITE
<222> LOCATION: (8)
<223> OTHER INFORMATION: Xaa is Phe, Ile, Leu, or Met
<220> FEATURE:
<221> NAME/KEY: SITE
<222> LOCATION: (9)
<223> OTHER INFORMATION: Xaa is Phe or Glu

<400> SEQUENCE: 11

Xaa Xaa Xaa Xaa Tyr Xaa Glu Xaa Xaa
  1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:Preferred
      phosphorylation site of pp60v-src
<220> FEATURE:
<221> NAME/KEY: SITE
<222> LOCATION: (1)..(2)
<223> OTHER INFORMATION: Xaa is Glu or Asp
<220> FEATURE:
<221> NAME/KEY: SITE
<222> LOCATION: (3)
<223> OTHER INFORMATION: Xaa is Glu, Asp, Gly, or Asn
<220> FEATURE:
<221> NAME/KEY: SITE
<222> LOCATION: (4)
<223> OTHER INFORMATION: Xaa is Ile, Val, Leu, or Pro
<220> FEATURE:
<221> NAME/KEY: SITE
<222> LOCATION: (6)
<223> OTHER INFORMATION: Xaa is Gly, Glu, or Asp
<220> FEATURE:
<221> NAME/KEY: SITE
<222> LOCATION: (7)
<223> OTHER INFORMATION: Xaa is Glu or Asp
<220> FEATURE:
<221> NAME/KEY: SITE
<222> LOCATION: (8)
<223> OTHER INFORMATION: Xaa is Phe, Ile, Leu, Val, or Met
<220> FEATURE:
<221> NAME/KEY: SITE
<222> LOCATION: (9)
<223> OTHER INFORMATION: Xaa is Glu or Asp

<400> SEQUENCE: 12

Xaa Xaa Xaa Xaa Tyr Xaa Xaa Xaa Xaa
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:Preferred
      phosphorylation site of the EGF receptor
<220> FEATURE:
<221> NAME/KEY: SITE
<222> LOCATION: (1)
<223> OTHER INFORMATION: Xaa is Glu, Asp, Arg, or Ala
<220> FEATURE:
<221> NAME/KEY: SITE
<222> LOCATION: (2)
```

```
<223> OTHER INFORMATION: Xaa is Glu or Asp
<220> FEATURE:
<221> NAME/KEY: SITE
<222> LOCATION: (3)
<223> OTHER INFORMATION: Xaa is Glu, Asp, Ala, Gln, or Pro
<220> FEATURE:
<221> NAME/KEY: SITE
<222> LOCATION: (4)
<223> OTHER INFORMATION: Xaa is Glu, Asp, Ile, Asn, or Val
<220> FEATURE:
<221> NAME/KEY: SITE
<222> LOCATION: (6)
<223> OTHER INFORMATION: Xaa is Phe, Val, Ile, Glu, Met, or Leu
<220> FEATURE:
<221> NAME/KEY: SITE
<222> LOCATION: (7)
<223> OTHER INFORMATION: Xaa is Glu, Phe, Asp, Val, or Ile
<220> FEATURE:
<221> NAME/KEY: SITE
<222> LOCATION: (8)
<223> OTHER INFORMATION: Xaa is Leu, Ile, Phe, Val, or Met
<220> FEATURE:
<221> NAME/KEY: SITE
<222> LOCATION: (9)
<223> OTHER INFORMATION: Xaa is Val, Phe, Pro, Glu, Leu, or Ile

<400> SEQUENCE: 13

Xaa Xaa Xaa Xaa Tyr Xaa Xaa Xaa Xaa
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:Preferred
      phosphorylation site of pp92c-fps/fes
<220> FEATURE:
<221> NAME/KEY: SITE
<222> LOCATION: (1)
<223> OTHER INFORMATION: Xaa is Glu, Ala, or Asp
<220> FEATURE:
<221> NAME/KEY: SITE
<222> LOCATION: (2)
<223> OTHER INFORMATION: Xaa is Glu or Ala
<220> FEATURE:
<221> NAME/KEY: SITE
<222> LOCATION: (3)
<223> OTHER INFORMATION: Xaa is Glu, Ala, or Gly
<220> FEATURE:
<221> NAME/KEY: SITE
<222> LOCATION: (4)
<223> OTHER INFORMATION: Xaa is Ile, Glu, Val, Asp, or Leu
<220> FEATURE:
<221> NAME/KEY: SITE
<222> LOCATION: (6)
<223> OTHER INFORMATION: Xaa is Glu, Asp, or Ala
<220> FEATURE:
<221> NAME/KEY: SITE
<222> LOCATION: (7)
<223> OTHER INFORMATION: Xaa is Glu, Asp, Ile, or Val
<220> FEATURE:
<221> NAME/KEY: SITE
<222> LOCATION: (8)
<223> OTHER INFORMATION: Xaa is Ile, Val, Glu, Met, or Leu
<220> FEATURE:
<221> NAME/KEY: SITE
<222> LOCATION: (9)
<223> OTHER INFORMATION: Xaa is Glu, Ile, Val, Asp, or Gly

<400> SEQUENCE: 14

Xaa Xaa Xaa Xaa Tyr Xaa Xaa Xaa Xaa
 1               5

<210> SEQ ID NO 15
<211> LENGTH: 9
```

```
<212> TYPE: PRT
<213> ORGANISM: Artificial Sequence
<220> FEATURE:
<223> OTHER INFORMATION: Description of Artificial Sequence:Walsh
      inhibitor sequence in pseudo-substrate domain

<400> SEQUENCE: 15

Gly Arg Arg Asn Ala Ile His Asp Ile
       1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:Kemptide
      sequence

<400> SEQUENCE: 16

Leu Arg Arg Ala Ser Leu Gly
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:Optimal
      peptide substrate based on fragment of Walsh inhibitor

<400> SEQUENCE: 17

Gly Arg Thr Gly Arg Arg Asn Ser Ile
  1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial
      Sequence:Phosphorylase kinase, a subunit

<400> SEQUENCE: 18

Phe Arg Arg Leu Ser Ile Ser Thr Glu
  1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial
      Sequence:Phosphorylase kinase, b subunit

<400> SEQUENCE: 19

Lys Arg Ser Gly Ser Val Tyr Glu Pro
  1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence:Glycogen
      synthase, site 1a

<400> SEQUENCE: 20

Pro Arg Arg Ala Ser Cys Thr Ser Ser
  1               5
```

```
<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:Glycogen
      synthase, site 1b

<400> SEQUENCE: 21

Lys Arg Ser Asn Ser Val Asp Thr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:Glycogen
      synthase, site 2

<400> SEQUENCE: 22

Ser Arg Thr Leu Ser Val Ser Ser Leu
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:Pyruvate
      kinase

<400> SEQUENCE: 23

Leu Arg Arg Ala Ser Leu Ala Gln Leu
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:
      6-phosphofructo-2-kinase/fructose-2,6-bisphosphata
      se

<400> SEQUENCE: 24

Arg Arg Arg Gly Ser Ser Ile Pro Gln
 1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:Protein
      phosphatase inhibitor I

<400> SEQUENCE: 25

Arg Arg Arg Pro Thr Pro Ala Thr Leu
 1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:pp60src
```

```
<400> SEQUENCE: 26

Gln Arg Arg Arg Ser Leu Glu Pro Ala
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence:Xenopus
      histone HI

<400> SEQUENCE: 27

Val Ala Ala Lys Ser Pro Ala Lys Ala
  1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:Xenopus
      histone HI

<400> SEQUENCE: 28

Lys Ala Ala Lys Ser Pro Lys Lys Thr
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:Chicken
      lamin B2

<400> SEQUENCE: 29

Gly Thr Pro Leu Ser Pro Thr Arg Ile
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:pp60c-src

<400> SEQUENCE: 30

Asp Thr His Arg Thr Pro Ser Arg Ser
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:SV40 LT
      antigen

<400> SEQUENCE: 31

Ser Gln His Ser Thr Pro Pro Lys Lys
  1               5

<210> SEQ ID NO 32
<211> LENGTH: 9
<212> TYPE: PRT
<213> ORGANISM: Artificial Sequence
<220> FEATURE:
```

```
<223> OTHER INFORMATION: Description of Artificial Sequence:Yeast SWI5

<400> SEQUENCE: 32

Tyr Thr Thr Asn Ser Pro Ser Lys Ile
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:Yeast SWI5

<400> SEQUENCE: 33

Val Ile Lys Arg Ser Pro Arg Lys Arg
 1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence:Protein
      phosphatase (T316)

<400> SEQUENCE: 34

Gly Arg Pro Ile Thr Pro Pro Arg Lys
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:Strathmin

<400> SEQUENCE: 35

Glu Phe Pro Leu Ser Pro Pro Lys Lys
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence:HIV Enhancer
      Binding Protein 2

<400> SEQUENCE: 36

Arg Arg Pro Val Ser Pro Gly Lys Asp
 1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:S6 Kinase II
      alpha (S335)

<400> SEQUENCE: 37

Arg Arg Glu Met Ser Pro Pro Phe Lys
 1               5

<210> SEQ ID NO 38
<211> LENGTH: 9
<212> TYPE: PRT
<213> ORGANISM: Artificial Sequence
```

-continued

```
<220> FEATURE:
<223> OTHER INFORMATION: Description of Artificial Sequence:Elongation
      factor I gamma (216)

<400> SEQUENCE: 38

Asp Lys Pro Leu Ser Pro Pro Gln Lys
 1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence:Histone H5
      (S133)

<400> SEQUENCE: 39

Arg Lys Ala Arg Ser Pro Ala Lys Lys
 1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence:Cell
      Division FTSZ protein (S548)

<400> SEQUENCE: 40

Arg Arg Pro Leu Ser Pro Glu Ala Ser
 1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial
      Sequence:Ubiquitin-Conjugating Enzyme

<400> SEQUENCE: 41

Asp Tyr Pro Leu Ser Pro Pro Lys Leu
 1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:Preferred
      sequence
<220> FEATURE:
<221> NAME/KEY: MOD_RES
<222> LOCATION: (1)
<223> OTHER INFORMATION: PHOSPHORYLATION
<220> FEATURE:
<221> NAME/KEY: SITE
<222> LOCATION: (2)
<223> OTHER INFORMATION: Xaa is Gly or Glu
<220> FEATURE:
<221> NAME/KEY: SITE
<222> LOCATION: (4)
<223> OTHER INFORMATION: Xaa is Phe or Ile

<400> SEQUENCE: 42

Tyr Xaa Glu Xaa
 1

<210> SEQ ID NO 43
<211> LENGTH: 4
```

```
<212> TYPE: PRT
<213> ORGANISM: Artificial Sequence
<220> FEATURE:
<223> OTHER INFORMATION: Description of Artificial Sequence:optimal
      sequence
<220> FEATURE:
<221> NAME/KEY: MOD_RES
<222> LOCATION: (1)
<223> OTHER INFORMATION: PHOSPHORYLATION

<400> SEQUENCE: 43

Tyr Glu Glu Ile
  1

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence:gastrin

<400> SEQUENCE: 44

Glu Glu Ala Tyr Gly Trp Met Asp
  1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:Enolase
      (Y43)

<400> SEQUENCE: 45

Thr Gly Ile Tyr Glu Ala Leu Glu
  1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:p34cdc2
      peptide (Y15)

<400> SEQUENCE: 46

Glu Gly Thr Tyr Gly Val Val Tyr
  1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:Mouse
      polyoma middle T (Y315)

<400> SEQUENCE: 47

Glu Glu Glu Tyr Met Pro Met Glu
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Hamster
      polyoma middle T (Y295)

<400> SEQUENCE: 48
```

Glu Asn Glu Tyr Met Pro Met Ala
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Hamster
      polyoma middle T (Y321)

<400> SEQUENCE: 49

Glu Pro Gln Tyr Glu Glu Ile Pro
 1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: PtdIns
      3-kinase p85 subunit (Y607)

<400> SEQUENCE: 50

Glu Asp Gln Tyr Ser Leu Val Glu
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:pp60v-src
      (Y416) autophosphorylation

<400> SEQUENCE: 51

Asp Asn Glu Tyr Thr Ala Arg Gln
 1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence:pp60v-src
      (Y92) autophosphorylation

<400> SEQUENCE: 52

Leu Tyr Asp Tyr Glu Ser Trp Ile
 1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: p125FAK
      (Y373) Phos.

<400> SEQUENCE: 53

Thr Asp Asp Tyr Ala Glu Ile Asp
 1               5

<210> SEQ ID NO 54
<211> LENGTH: 8
<212> TYPE: PRT
<213> ORGANISM: Artificial Sequence
<220> FEATURE:

```
<223> OTHER INFORMATION: Description of Artificial Sequence: T cell
      receptor (Y110)

<400> SEQUENCE: 54

Glu Gly Leu Tyr Asn Glu Leu Gln
  1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: T cell
      receptor (Y122)

<400> SEQUENCE: 55

Ala Glu Ala Tyr Ser Glu Ile Gly
  1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:optimal
      substrate
<220> FEATURE:
<221> NAME/KEY: SITE
<222> LOCATION: (1)
<223> OTHER INFORMATION: Xaa is any hydrophobic amino acid
<220> FEATURE:
<221> NAME/KEY: SITE
<222> LOCATION: (2)
<223> OTHER INFORMATION: Xaa is any amino acid
<220> FEATURE:
<221> NAME/KEY: SITE
<222> LOCATION: (3)..(4)
<223> OTHER INFORMATION: Xaa is any hydrophobic amino acid

<400> SEQUENCE: 56

Xaa Xaa Xaa Xaa
  1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence:motif
      recognized by type III SH2 domains
<220> FEATURE:
<221> NAME/KEY: MOD_RES
<222> LOCATION: (1)
<223> OTHER INFORMATION: PHOSPHORYLATION
<220> FEATURE:
<221> NAME/KEY: SITE
<222> LOCATION: (2)
<223> OTHER INFORMATION: Xaa is any hydrophobic amino acid
<220> FEATURE:
<221> NAME/KEY: SITE
<222> LOCATION: (3)
<223> OTHER INFORMATION: Xaa is any amino acid
<220> FEATURE:
<221> NAME/KEY: SITE
<222> LOCATION: (4)
<223> OTHER INFORMATION: Xaa is any hydrophobic amino acid

<400> SEQUENCE: 57

Tyr Xaa Xaa Xaa
  1

<210> SEQ ID NO 58
```

-continued

```
<211> LENGTH: 9
<212> TYPE: PRT
<213> ORGANISM: Artificial Sequence
<220> FEATURE:
<223> OTHER INFORMATION: Description of Artificial Sequence:EGF Receptor
      Autophos. site (Y1069)

<400> SEQUENCE: 58

Pro Val Pro Glu Tyr Ile Asn Gln Ser
  1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:EGF receptor
      autophos. site (Y1086)

<400> SEQUENCE: 59

Gln Asn Pro Val Tyr His Asn Gln Pro
  1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence:EGF receptor
      autophos. site (Y111R)

<400> SEQUENCE: 60

Gly Asn Pro Glu Tyr Leu Asn Thr Val
  1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence:EGF receptor
      autophos. site (Y1148)

<400> SEQUENCE: 61

Asp Asn Pro Asp Tyr Gln Gln Asp Phe
  1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence:EGF receptor
      autophos. site (Y1173)

<400> SEQUENCE: 62

Glu Asn Ala Glu Tyr Leu Arg Val Ala
  1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence:EGF receptor
      autophos. site (Y992)

<400> SEQUENCE: 63
```

-continued

Asp Ala Asp Glu Tyr Leu Ile Pro Gln
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence:Lipocortin
      (Y21)

<400> SEQUENCE: 64

Glu Glu Gln Glu Tyr Val Gln Thr Val
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:myosin light
      chain

<400> SEQUENCE: 65

Val Asp Glu Met Tyr Arg Glu Ala Pro
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence:myosin light
      chain

<400> SEQUENCE: 66

Gly Asn Phe Asn Tyr Val Glu Phe Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial
      Sequence:Phospholipase C-gamma (Y771)

<400> SEQUENCE: 67

Ala Glu Pro Asp Tyr Gly Ala Leu Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial
      Sequence:Phospholipase C-gamma (Y1254)

<400> SEQUENCE: 68

Phe Glu Ala Arg Tyr Gln Gln Pro Phe
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence:Gastrin -continued

<400> SEQUENCE: 69

Glu Glu Glu Ala Tyr Gly Trp Met Asp
 1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence:p21ras
      peptide

<400> SEQUENCE: 70

Gly Gln Glu Glu Tyr Ser Ala
 1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:Chicken
      lactate dehydrenase (y238)

<400> SEQUENCE: 71

Val Glu Ser Ala Tyr Glu Val Ile Arg
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:Human
      enolase (Y43)

<400> SEQUENCE: 72

Ser Thr Gly Ile Tyr Glu Ala Leu Glu
 1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence:P140gag-fps
      (Y424)

<400> SEQUENCE: 73

Glu Asp Gly Val Tyr Ala Ser Thr Gly
 1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence:P110gag-fes
      (Y500)

<400> SEQUENCE: 74

Ala Asp Gly Ile Tyr Ala Ala Ser Gly
 1               5

<210> SEQ ID NO 75
<211> LENGTH: 11
<212> TYPE: PRT

<213> ORGANISM: Artificial Sequence
<220> FEATURE:
<223> OTHER INFORMATION: Description of Artificial Sequence:peptide
      synthesized as a substrate for cyclin containing
      kinases

<400> SEQUENCE: 75

Ala Arg Arg Pro Met Ser Pro Lys Lys Lys Ala
 1               5                  10

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence:peptide
      synthesized as a substrate for src tyrosine
      kinases

<400> SEQUENCE: 76

Ala Glu Glu Glu Ile Tyr Gly Glu Phe Glu Ala Lys Lys Lys Lys
 1               5                  10                  15

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence:peptide
      based upon the site of tyrosine phosphorylation on p33cdc2

<400> SEQUENCE: 77

Ile Glu Lys Ile Gly Glu Gly Thr Tyr Gly Val Val Tyr Lys Gly Arg
 1               5                  10                  15

His Lys Thr Thr
            20

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence:preferred
      residues at positions surrounding phosphorylation
      site of lck
<220> FEATURE:
<221> NAME/KEY: SITE
<222> LOCATION: (1)
<223> OTHER INFORMATION: Xaa is any amino acid
<220> FEATURE:
<221> NAME/KEY: SITE
<222> LOCATION: (2)
<223> OTHER INFORMATION: Xaa is Glu, Gly, Pro or Ala
<220> FEATURE:
<221> NAME/KEY: SITE
<222> LOCATION: (3)
<223> OTHER INFORMATION: Xaa is any amino acid
<220> FEATURE:
<221> NAME/KEY: SITE
<222> LOCATION: (4)
<223> OTHER INFORMATION: Xaa is Ile, Val, Leu, Phe, or Met
<220> FEATURE:
<221> NAME/KEY: SITE
<222> LOCATION: (6)
<223> OTHER INFORMATION: Xaa is Gly, Ala, Met, Glu or Val
<220> FEATURE:
<221> NAME/KEY: SITE
<222> LOCATION: (7)
<223> OTHER INFORMATION: Xaa is Val, Ala, Pro, Met, Ile, Phe, Lys, or
      Leu
<220> FEATURE:
<221> NAME/KEY: SITE
<222> LOCATION: (8)

```
<223> OTHER INFORMATION: Xaa is Leu, Val, Phe, Ile, or Met
<220> FEATURE:
<221> NAME/KEY: SITE
<222> LOCATION: (9)
<223> OTHER INFORMATION: Xaa is Phe, Leu, Val, Ile, Pro, Met, Lys, or
      Gly

<400> SEQUENCE: 78

Xaa Xaa Xaa Xaa Tyr Xaa Xaa Xaa Xaa
 1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence:preferred
      residues surrounding phosphorylation site of c-abl
<220> FEATURE:
<221> NAME/KEY: SITE
<222> LOCATION: (1)
<223> OTHER INFORMATION: Xaa is Ala, Arg, Gly, or Pro
<220> FEATURE:
<221> NAME/KEY: SITE
<222> LOCATION: (2)
<223> OTHER INFORMATION: Xaa is any amino acid
<220> FEATURE:
<221> NAME/KEY: SITE
<222> LOCATION: (3)
<223> OTHER INFORMATION: Xaa is Val, Ala, Pro, Ile, Gly, or Glu
<220> FEATURE:
<221> NAME/KEY: SITE
<222> LOCATION: (4)
<223> OTHER INFORMATION: Xaa is Ile, Val, Leu, or Met
<220> FEATURE:
<221> NAME/KEY: SITE
<222> LOCATION: (6)
<223> OTHER INFORMATION: Xaa is Ala, Met, Gln, Gly, or Phe
<220> FEATURE:
<221> NAME/KEY: SITE
<222> LOCATION: (7)
<223> OTHER INFORMATION: Xaa is Ala, Val, Phe, Met, Gln, Leu, or Ile
<220> FEATURE:
<221> NAME/KEY: SITE
<222> LOCATION: (8)
<223> OTHER INFORMATION: Xaa is Pro, Phe, Leu, Ile, Val, or Ala
<220> FEATURE:
<221> NAME/KEY: SITE
<222> LOCATION: (9)
<223> OTHER INFORMATION: Xaa is Phe, Leu, Ile, Met, Gly, or Pro

<400> SEQUENCE: 79

Xaa Xaa Xaa Xaa Tyr Xaa Xaa Xaa Xaa
 1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence:preferred
      residues surrounding phosphorylation site of PDGF
      receptor
<220> FEATURE:
<221> NAME/KEY: SITE
<222> LOCATION: (1)..(4)
<223> OTHER INFORMATION: Xaa is Glu or Asp
<220> FEATURE:
<221> NAME/KEY: SITE
<222> LOCATION: (6)
<223> OTHER INFORMATION: Xaa is Val, Glu, or Ile
<220> FEATURE:
<221> NAME/KEY: SITE
<222> LOCATION: (8)
<223> OTHER INFORMATION: Xaa is Ile, Val, or Phe
<220> FEATURE:
```

```
<221> NAME/KEY: SITE
<222> LOCATION: (9)
<223> OTHER INFORMATION: Xaa is any amino acid

<400> SEQUENCE: 80

Xaa Xaa Xaa Xaa Tyr Xaa Phe Xaa Xaa
 1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence:preferred
      residues surrounding phosphorylation site of FGF
      receptor
<220> FEATURE:
<221> NAME/KEY: SITE
<222> LOCATION: (1)
<223> OTHER INFORMATION: Xaa is Ala, Lys, Glu, Phe, Pro, or Gly
<220> FEATURE:
<221> NAME/KEY: SITE
<222> LOCATION: (2)
<223> OTHER INFORMATION: Xaa is Glu, Ala, Phe, Lys, Met, Gly, Ile, or
      Val
<220> FEATURE:
<221> NAME/KEY: SITE
<222> LOCATION: (3)
<223> OTHER INFORMATION: Xaa is Glu, Lys, Ala, Phe, Pro, Gly, or Val
<220> FEATURE:
<221> NAME/KEY: SITE
<222> LOCATION: (4)
<223> OTHER INFORMATION: Xaa is Glu, Ile, Val, Asp, Phe, Ala, or Leu
<220> FEATURE:
<221> NAME/KEY: SITE
<222> LOCATION: (6)
<223> OTHER INFORMATION: Xaa is Phe, Val, Glu, Ile, Met, Ala, or Lys
<220> FEATURE:
<221> NAME/KEY: SITE
<222> LOCATION: (7)
<223> OTHER INFORMATION: Xaa is Phe, Val, Met, Ile, Leu, Glu, Pro, or
      Lys
<220> FEATURE:
<221> NAME/KEY: SITE
<222> LOCATION: (8)
<223> OTHER INFORMATION: Xaa is Leu, Phe, Met, Ile, Val or Glu
<220> FEATURE:
<221> NAME/KEY: SITE
<222> LOCATION: (9)
<223> OTHER INFORMATION: Xaa is Phe, Leu, Met, Val, Glu, Ile, or Pro

<400> SEQUENCE: 81

Xaa Xaa Xaa Xaa Tyr Xaa Xaa Xaa Xaa
 1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence:preferred
      residues surrounding phosphorylation site of
      insulin receptor
<220> FEATURE:
<221> NAME/KEY: SITE
<222> LOCATION: (1)
<223> OTHER INFORMATION: Xaa is any amino acid
<220> FEATURE:
<221> NAME/KEY: SITE
<222> LOCATION: (2)
<223> OTHER INFORMATION: Xaa is Glu, Gly, Ala, Phe, Asn, or Met
<220> FEATURE:
<221> NAME/KEY: SITE
<222> LOCATION: (3)
<223> OTHER INFORMATION: Xaa is Glu, Ala, Gly, Pro, or Asn
<220> FEATURE:
```

```
<221> NAME/KEY: SITE
<222> LOCATION: (4)
<223> OTHER INFORMATION: Xaa is Glu, Asn, Asp, Ala, Ile, Pro, or Gly
<220> FEATURE:
<221> NAME/KEY: SITE
<222> LOCATION: (6)
<223> OTHER INFORMATION: Xaa is Met, Phe, Ala, Glu, or Val
<220> FEATURE:
<221> NAME/KEY: SITE
<222> LOCATION: (7)
<223> OTHER INFORMATION: Xaa is Met, Phe, Val, Glu, Ala, Asp, Leu or Ile
<220> FEATURE:
<221> NAME/KEY: SITE
<222> LOCATION: (8)
<223> OTHER INFORMATION: Xaa is Met, Phe, Ile, Glu, or Val
<220> FEATURE:
<221> NAME/KEY: SITE
<222> LOCATION: (9)
<223> OTHER INFORMATION: Xaa is Met, Phe, Glu, Val, Leu, Ile, or Gly

<400> SEQUENCE: 82

Xaa Xaa Xaa Xaa Tyr Xaa Xaa Xaa Xaa
 1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence:preferred
      residues surrounding phosphorylation site of
      casein kinase II
<220> FEATURE:
<221> NAME/KEY: SITE
<222> LOCATION: (1)
<223> OTHER INFORMATION: Xaa is Glu, Asp, Ala, or Gly
<220> FEATURE:
<221> NAME/KEY: SITE
<222> LOCATION: (2)
<223> OTHER INFORMATION: Xaa is Asp, Glu, Gly, or Ala
<220> FEATURE:
<221> NAME/KEY: SITE
<222> LOCATION: (3)
<223> OTHER INFORMATION: Xaa is Glu, Asp, Ala, or Gly
<220> FEATURE:
<221> NAME/KEY: SITE
<222> LOCATION: (4)
<223> OTHER INFORMATION: Xaa is Glu, Asp, Gly, Ala, or Met
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (6)
<223> OTHER INFORMATION: Xaa is Glu, Asp, or Ala
<220> FEATURE:
<221> NAME/KEY: SITE
<222> LOCATION: (7)
<223> OTHER INFORMATION: Xaa is Asp, Glu, or Ala
<220> FEATURE:
<221> NAME/KEY: SITE
<222> LOCATION: (8)
<223> OTHER INFORMATION: Xaa is Glu, Asp, or Ala
<220> FEATURE:
<221> NAME/KEY: SITE
<222> LOCATION: (9)
<223> OTHER INFORMATION: Xaa is Glu, Asp, or Ile

<400> SEQUENCE: 83

Xaa Xaa Xaa Xaa Xaa Xaa Xaa Xaa Xaa
 1               5

<210> SEQ ID NO 84
<211> LENGTH: 9
<212> TYPE: PRT
```

-continued

```
<213> ORGANISM: Artificial Sequence
<220> FEATURE:
<223> OTHER INFORMATION: Description of Artificial Sequence:preferred
      residues surrounding phosphorylation site of NIMA
<220> FEATURE:
<221> NAME/KEY: SITE
<222> LOCATION: (1)
<223> OTHER INFORMATION: Xaa is Arg, Asn, Phe, Met, Gln, or Gly
<220> FEATURE:
<221> NAME/KEY: SITE
<222> LOCATION: (2)
<223> OTHER INFORMATION: Xaa is Phe, Leu, or Met
<220> FEATURE:
<221> NAME/KEY: SITE
<222> LOCATION: (3)
<223> OTHER INFORMATION: Xaa is Arg, Lys, or Asn
<220> FEATURE:
<221> NAME/KEY: SITE
<222> LOCATION: (4)
<223> OTHER INFORMATION: Xaa is Arg, Lys, Met, or Gln
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (6)
<223> OTHER INFORMATION: Xaa is Arg, Ile, Val, Met, Leu, or Gln
<220> FEATURE:
<221> NAME/KEY: SITE
<222> LOCATION: (7)
<223> OTHER INFORMATION: Xaa is Arg, Ile, Met, Val, Phe, or Leu
<220> FEATURE:
<221> NAME/KEY: SITE
<222> LOCATION: (8)
<223> OTHER INFORMATION: Xaa is Met, Ile, Phe, Val, Leu, or Gly
<220> FEATURE:
<221> NAME/KEY: SITE
<222> LOCATION: (9)
<223> OTHER INFORMATION: Xaa is Ile, Phe, Met, Gly, Leu, or Val

<400> SEQUENCE: 84

Xaa Xaa Xaa Xaa Xaa Xaa Xaa Xaa Xaa
  1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence:Preferred
      residues near phosphorylation site of
      phosphorylase kinase
<220> FEATURE:
<221> NAME/KEY: SITE
<222> LOCATION: (1)
<223> OTHER INFORMATION: Xaa is Phe, Met, Lys, Ile, His, or Val
<220> FEATURE:
<221> NAME/KEY: SITE
<222> LOCATION: (2)
<223> OTHER INFORMATION: Xaa is Arg or Lys
<220> FEATURE:
<221> NAME/KEY: SITE
<222> LOCATION: (3)
<223> OTHER INFORMATION: Xaa is Met, Arg, Gln, Phe, Lys, or Leu
<220> FEATURE:
<221> NAME/KEY: SITE
<222> LOCATION: (4)
<223> OTHER INFORMATION: Xaa is Met, Phe, Leu, Ile, Lys, or Val
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (6)
<223> OTHER INFORMATION: Xaa is Phe, Ile, Met, Leu, or Val
<220> FEATURE:
```

```
<221> NAME/KEY: SITE
<222> LOCATION: (7)
<223> OTHER INFORMATION: Xaa is Phe, Arg, Lys, Met or Ile
<220> FEATURE:
<221> NAME/KEY: SITE
<222> LOCATION: (8)
<223> OTHER INFORMATION: Xaa is Leu, Ile, Met, Pro or Val
<220> FEATURE:
<221> NAME/KEY: SITE
<222> LOCATION: (9)
<223> OTHER INFORMATION: Xaa is Phe, Leu, Ile, Val, Pro, or Met

<400> SEQUENCE: 85

Xaa Xaa Xaa Xaa Xaa Xaa Xaa Xaa Xaa
  1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence:preferred
      residues surrounding phosphorylation site of Cam
      Kinase II
<220> FEATURE:
<221> NAME/KEY: SITE
<222> LOCATION: (1)
<223> OTHER INFORMATION: Xaa is Lys, Phe, Asp, His, or Met
<220> FEATURE:
<221> NAME/KEY: SITE
<222> LOCATION: (2)
<223> OTHER INFORMATION: Xaa is Arg, Lys, Phe, or Met
<220> FEATURE:
<221> NAME/KEY: SITE
<222> LOCATION: (3)
<223> OTHER INFORMATION: Xaa is Gln, Met, Lys, Ala, or Phe
<220> FEATURE:
<221> NAME/KEY: SITE
<222> LOCATION: (4)
<223> OTHER INFORMATION: Xaa is Gln, Met, Lys, Leu, Phe, or Ala
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (6)
<223> OTHER INFORMATION: Xaa is Phe, Ile, Met, Leu, or Val
<220> FEATURE:
<221> NAME/KEY: SITE
<222> LOCATION: (7)
<223> OTHER INFORMATION: Xaa is Asp, Glu, Ile, Met, Lys, Val, or Leu
<220> FEATURE:
<221> NAME/KEY: SITE
<222> LOCATION: (8)
<223> OTHER INFORMATION: Xaa is Leu, Met, Lys, Ile, Val, Gln, or Gly
<220> FEATURE:
<221> NAME/KEY: SITE
<222> LOCATION: (9)
<223> OTHER INFORMATION: Xaa is Phe, Lys, Met, Val, Leu, Ile, or Pro

<400> SEQUENCE: 86

Xaa Xaa Xaa Xaa Xaa Xaa Xaa Xaa Xaa
  1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence:Preferred
      residues surrounding phosphorylation site of Erk1
<220> FEATURE:
<221> NAME/KEY: SITE
<222> LOCATION: (1)
```

```
<223> OTHER INFORMATION: Xaa is Thr, Pro, Ser, Gln, Ile, Val, Asn, or
      Glu
<220> FEATURE:
<221> NAME/KEY: SITE
<222> LOCATION: (2)
<223> OTHER INFORMATION: Xaa is Gly, Pro, Glu, Tyr, or Gln
<220> FEATURE:
<221> NAME/KEY: SITE
<222> LOCATION: (3)
<223> OTHER INFORMATION: Xaa is Pro, Leu, Ile, or Val
<220> FEATURE:
<221> NAME/KEY: SITE
<222> LOCATION: (4)
<223> OTHER INFORMATION: Xaa is Leu, Met, Pro, Lys, Gln, or Thr
<220> FEATURE:
<221> NAME/KEY: SITE
<222> LOCATION: (5)
<223> OTHER INFORMATION: Xaa is Ser or Thr
<220> FEATURE:
<221> NAME/KEY: SITE
<222> LOCATION: (7)
<223> OTHER INFORMATION: Xaa is Gly, Pro, Phe, Thr, or Leu
<220> FEATURE:
<221> NAME/KEY: SITE
<222> LOCATION: (8)
<223> OTHER INFORMATION: Xaa is Pro, Phe, Gly, Tyr, Leu, or Ile
<220> FEATURE:
<221> NAME/KEY: SITE
<222> LOCATION: (9)
<223> OTHER INFORMATION: Xaa is Phe, Tyr, Ile, or Leu

<400> SEQUENCE: 87

Xaa Xaa Xaa Xaa Xaa Pro Xaa Xaa Xaa
  1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence:synthetic
      abl optimal peptide

<400> SEQUENCE: 88

Glu Ala Ile Tyr Ala Ala Pro Phe Ala Lys Lys Lys
  1               5                  10

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence:tetrapeptide

<400> SEQUENCE: 89

Ala Lys Lys Lys
  1

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence:substrate
<220> FEATURE:
<221> NAME/KEY: SITE
<222> LOCATION: (1)
<223> OTHER INFORMATION: Xaa is any amino acid
<220> FEATURE:
<221> NAME/KEY: SITE
<222> LOCATION: (3)
<223> OTHER INFORMATION: Xaa is any amino acid
<220> FEATURE:
<221> NAME/KEY: SITE
```

```
<222> LOCATION: (4)
<223> OTHER INFORMATION: Xaa is Ile, Val, Leu, or Phe
<220> FEATURE:
<221> NAME/KEY: SITE
<222> LOCATION: (6)
<223> OTHER INFORMATION: Xaa is Gly or Ala
<220> FEATURE:
<221> NAME/KEY: SITE
<222> LOCATION: (8)
<223> OTHER INFORMATION: Xaa is Leu, Val, Phe, or Ile
<220> FEATURE:
<221> NAME/KEY: SITE
<222> LOCATION: (9)
<223> OTHER INFORMATION: Xaa is Phe, Leu, Val, or Ile

<400> SEQUENCE: 90

Xaa Glu Xaa Xaa Tyr Xaa Val Xaa Xaa
 1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial
      Sequence:pseudosubstrate for lck
<220> FEATURE:
<221> NAME/KEY: SITE
<222> LOCATION: (1)
<223> OTHER INFORMATION: Xaa is any amino acid
<220> FEATURE:
<221> NAME/KEY: SITE
<222> LOCATION: (2)
<223> OTHER INFORMATION: Xaa is Glu, Gly, Pro, or Ala
<220> FEATURE:
<221> NAME/KEY: SITE
<222> LOCATION: (3)
<223> OTHER INFORMATION: Xaa is any amino acid
<220> FEATURE:
<221> NAME/KEY: SITE
<222> LOCATION: (4)
<223> OTHER INFORMATION: Xaa is Ile, Val, Leu, Phe, or Met
<220> FEATURE:
<221> NAME/KEY: SITE
<222> LOCATION: (5)
<223> OTHER INFORMATION: Xaa is any amino acid except Tyr
<220> FEATURE:
<221> NAME/KEY: SITE
<222> LOCATION: (6)
<223> OTHER INFORMATION: Xaa is Gly, Ala, Met, Glu, or Val
<220> FEATURE:
<221> NAME/KEY: SITE
<222> LOCATION: (7)
<223> OTHER INFORMATION: Xaa is Val, Ala, Pro, Met, Ile, Phe, Lys, or
      Leu
<220> FEATURE:
<221> NAME/KEY: SITE
<222> LOCATION: (8)
<223> OTHER INFORMATION: Xaa is Leu, Val, Phe, Ile, or Met
<220> FEATURE:
<221> NAME/KEY: SITE
<222> LOCATION: (9)
<223> OTHER INFORMATION: Xaa is Phe, Leu, Val, Ile, Pro, Met, Lys, or
      Gly

<400> SEQUENCE: 91

Xaa Xaa Xaa Xaa Xaa Xaa Xaa Xaa Xaa
 1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial
      Sequence:pseudosubstrate for lck
```

```
<220> FEATURE:
<221> NAME/KEY: SITE
<222> LOCATION: (1)
<223> OTHER INFORMATION: Xaa is any amino acid
<220> FEATURE:
<221> NAME/KEY: SITE
<222> LOCATION: (2)
<223> OTHER INFORMATION: Xaa is Glu, Gly, Pro, or Ala
<220> FEATURE:
<221> NAME/KEY: SITE
<222> LOCATION: (3)
<223> OTHER INFORMATION: Xaa is any amino acid
<220> FEATURE:
<221> NAME/KEY: SITE
<222> LOCATION: (4)
<223> OTHER INFORMATION: Xaa is Ile, Val, Leu, Phe, or Met
<220> FEATURE:
<221> NAME/KEY: SITE
<222> LOCATION: (5)
<223> OTHER INFORMATION: Xaa is Phe or His
<220> FEATURE:
<221> NAME/KEY: SITE
<222> LOCATION: (6)
<223> OTHER INFORMATION: Xaa is Gly, Ala, Met, Glu, or Val
<220> FEATURE:
<221> NAME/KEY: SITE
<222> LOCATION: (7)
<223> OTHER INFORMATION: Xaa is Val, Ala, Pro, Met, Ile, Phe, Lys, or
     Leu
<220> FEATURE:
<221> NAME/KEY: SITE
<222> LOCATION: (8)
<223> OTHER INFORMATION: Xaa is Leu, Val, Phe, Ile, of Met
<220> FEATURE:
<221> NAME/KEY: SITE
<222> LOCATION: (9)
<223> OTHER INFORMATION: Xaa is Phe, Leu, Val, Ile, Pro, Met, Lys, or
     Gly

<400> SEQUENCE: 92

Xaa Xaa Xaa Xaa Xaa Xaa Xaa Xaa Xaa
 1               5
```